(12) United States Patent
Aspnes et al.

(10) Patent No.: US 6,441,015 B2
(45) Date of Patent: Aug. 27, 2002

(54) TETRAZOLE COMPOUNDS AS THYROID RECEPTOR LIGANDS

(75) Inventors: Gary E. Aspnes, Rockville, RI (US); Yuan-Ching P. Chiang, East Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/767,771

(22) Filed: Jan. 23, 2001

Related U.S. Application Data

(60) Provisional application No. 60/177,987, filed on Jan. 25, 2000.

(51) Int. Cl.[7] .................. A61F 31/41; C07D 257/04
(52) U.S. Cl. .................. 514/381; 548/250; 548/251; 548/253; 548/254; 514/382
(58) Field of Search .................. 548/250, 251, 548/253, 254; 514/381, 382

(56) References Cited

U.S. PATENT DOCUMENTS

| | | |
|---|---|---|
| 4,766,121 A | 8/1988 | Ellis et al. |
| 4,992,576 A | 2/1991 | Gapinski |
| 5,284,971 A | 2/1994 | Walker et al. |
| 5,347,036 A | 9/1994 | Scherrer |
| 5,399,471 A * | 3/1995 | Murai et al. .......... 430/544 |
| 5,569,674 A | 10/1996 | Yokoyama et al. |

FOREIGN PATENT DOCUMENTS

| | | |
|---|---|---|
| EP | 0212848 | 7/1986 |
| EP | 0276064 | 1/1988 |
| EP | 0380331 | 8/1990 |
| WO | WO9831227 | 7/1998 |
| WO | WO9842650 | 10/1998 |
| WO | WO9900353 | 1/1999 |
| WO | WO0039077 | 7/2000 |

OTHER PUBLICATIONS

M. Ebisawa, et al. Thiazolidinediones with Thyroid Hormone Receptor Agonistic Activity. *Chem. Pharm. Bull.* 1999. vol. 47(9). pp. 1348–1350.
European Patent Office search report.

* cited by examiner

*Primary Examiner*—Floyd Higel
*Assistant Examiner*—Kamal Saeed
(74) *Attorney, Agent, or Firm*—Peter C. Richardson; Gregg C. Benson; Todd M. Crissey

(57) ABSTRACT

The present invention relates to tetrazole compounds of Formula I, stereoisomers, pharmaceutically acceptable salts and prodrugs thereof, and pharmaceutically acceptable salts of the prodrugs.

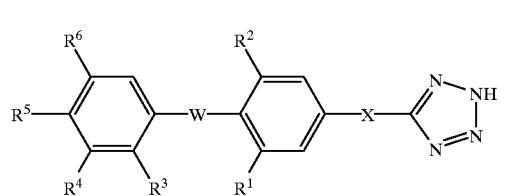

The invention also relates to compositions comprising the tetrazole compounds and to methods of treating obesity, diabetes, atherosclerosis, hypertension, coronary heart disease, hypercholesterolemia, hyperlipidemia, thyroid disease, thyroid cancer, hypothyroidism, depression, glaucoma, cardiac arrhythmias, congestive heart failure, and osteoporosis using the tetrazole compounds.

31 Claims, No Drawings

TETRAZOLE COMPOUNDS AS THYROID RECEPTOR LIGANDS

CROSS REFERENCE TO RELATED APPLICATION

This application claims priority of U.S. provisional application No. 60/177,987, filed Jan. 25, 2000.

FIELD OF THE INVENTION

The present invention relates to tetrazole compounds that are thyroid receptor ligands. The invention also relates to compositions and kits comprising the tetrazole compounds and to methods of treatment of obesity, diabetes, atherosclerosis, hypertension, coronary heart disease, hypercholesterolemia, hyperlipidemia, thyroid disease, thyroid cancer, hypothyroidism, depression, glaucoma, cardiac arrhythmias, congestive heart failure, and osteoporosis using the tetrazole compounds.

BACKGROUND OF THE INVENTION

Thyroid hormones are important in normal development and in maintaining metabolic homeostasis. For example, thyroid hormones stimulate the metabolism of cholesterol to bile acids and enhance the lipolytic responses of fat cells to other hormones.

Thyroid hormones also affect cardiac function both directly and indirectly, e.g., by increasing the metabolic rate. For example, tachycardia, increased stroke volume, increased cardiac index, cardiac hypertrophy, decreased peripheral vascular resistance and increased pulse pressure are observed in patients with hyperthyroidism.

Disorders of the thyroid gland are generally treated by administering either naturally occurring thyroid hormones or analogues that mimic the effects of thyroid hormones. Such analogues are called thyromimetics or thyroid receptor ligands.

Two naturally occurring thyroid hormones, 3,5,3',5'-tetraiodo-L-thyronine (also referred to as "$T_4$" or thyroxine) and 3,5,3'-triiodo-L-thyronine (also referred to as "$T_3$"), are shown below:

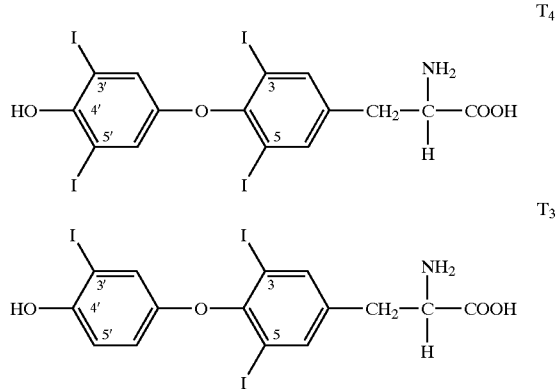

$T_3$ is more biologically active than $T_4$, and differs from $T_4$ by the absence of the 5' iodine. $T_3$ may be produced directly in the thyroid gland, or in peripheral tissues, by the removal of the 5' iodine of $T_4$ by deiodinase enzymes. Thyroid receptor ligands can be designed to be structurally similar to $T_3$. In addition, naturally occurring metabolites of $T_3$ are known.

As discussed above, thyroid hormones affect cardiac functioning, for example, by causing an increase in heart rate, and accordingly, an increase in oxygen consumption. While the increase in oxygen consumption can result in certain desired metabolic effects, nonetheless, it does place an extra burden on the heart, which in some situations, may give rise to damaging side effects. Consequently, efforts have been made to synthesize thyroid hormone analogs that function to lower lipids and serum cholesterol, but which have reduced adverse cardiac effects.

U.S. Pat. Nos. 4,766,121; 4,826,876; 4,910,305; and 5,061,798 disclose thyroid hormone mimetics, namely, 3,5-dibromo-3'-[6-oxo-3(1H)-pyridazinylmethyl]-thyronines.

U.S. Pat. No. 5,284,971 discloses thyromimetic cholesterol lowering agents, namely, 4-(3-cyclohexyl-4-hydroxy or -methoxy phenylsulfonyl)-3,5 dibromo-phenylacetic compounds.

U.S. Pat. Nos. 5,654,468 and 5,569,674 disclose certain lipid lowering agents, namely, heteroacetic acid derivatives, which compete with radiolabeled $T_3$ in binding assays using rat liver nuclei and plasma membrane preparations.

Certain oxamic acids and derivatives thereof are known in the art, e.g., U.S. Pat. No. 4,069,343 describes the use of certain oxamic acids to prevent immediate type hypersensitivity reactions; U.S. Pat. No. 4,554,290 describes the use of certain oxamic acids to control pests on animals and plants; U.S. Pat. No. 5,232,947 describes the use of certain oxamic acids to improve damaged cerebral functions of the brain; and European Patent Specification published as EP 580,550 (also U.S. Pat. No. 5,401,772) discloses certain oxamic acid derivatives as hypocholesterolemic agents.

In addition, certain oxamic acid derivatives of thyroid hormones are known in the art. For example, N. Yokoyama et al. in an article published in the *Journal of Medicinal Chemistry*, 38 (4): 695–707 (1995) describe replacing a —$CH_2$ group in a naturally occurring metabolite of $T_3$ with an —NH group resulting in —$HNCOCO_2H$. Likewise, R. E. Steele et al. in an article published in International Congressional Service (*Atherosclerosis* X) 106: 321–324 (1995) and Z. F. Stephan et al. in an article published in *Atherosclerosis*, 126: 53–63 (1996), describe certain oxamic acid derivatives useful as lipid-lowering thyromimetic agents that have reduced adverse cardiac activities.

European Patent Application EP 276,064 discloses some tetrazole compounds that are leukotriene antagonists as anti-inflammatory agents. Similarly, U.S. Pat. No. 5,347,036 discloses some tetrazole compounds that are leukotriene inhibitors. The tetrazole compounds disclosed in EP 276,064 and U.S. Pat. No. 5,347,036 are structurally different from the compounds of the present invention.

Obesity is a devastating disease. In addition to harming physical health, obesity can wreak havoc on mental health because obesity affects self-esteem, which ultimately can affect a person's ability to interact socially with others. Unfortunately, obesity is not well understood, and societal stereotypes and presumptions regarding obesity only tend to exacerbate the psychological effects of the disease. Because of the impact of obesity on individuals and society, much effort has been expended to find ways to treat obesity, but little success has been achieved in the long-term treatment and/or prevention of obesity. The present invention provides methods of treating obesity by administering to an obese patient or a patient at risk of becoming obese a therapeutically effective amount of a thyromimetic of the present invention. It is believed that the thyromimetics of the present invention act to treat obesity by increasing energy expenditure, and thus promoting weight loss.

The thyromimetics of the present invention can also be used to treat diabetes, atherosclerosis, hypertension, coronary heart disease, hypercholesterolemia, hyperlipidemia, thyroid disease, thyroid cancer, hypothyroidism, depression, glaucoma, cardiac arrhythmias, congestive heart failure, and osteoporosis.

In spite of the early discovery of insulin and its subsequent widespread use in the treatment of diabetes, and the later discovery of and use of sulfonylureas, biguanides and thiazolidenediones, such as troglitazone, rosiglitazone or pioglitazone, as oral hypoglycemic agents, the treatment of diabetes remains less than satisfactory.

The use of insulin currently requires multiple daily doses, usually by self-injection. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of non-insulin dependent diabetes mellitus (Type II diabetes, NIDDM) usually consists of a combination of diet, exercise, oral hypoglycemic agents, e.g., thiazolidenediones, and, in more severe cases, insulin. However, the clinically available hypoglycemic agents can have side effects that limit their use, or an agent may not be effective with a particular patient. In the case of insulin dependent diabetes mellitus (Type I), insulin is usually the primary course of therapy. Hypoglycemic agents that have fewer side effects or succeed where others fail are needed.

Atherosclerosis, a disease of the arteries, is recognized to be a leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, give rise to development of "fibrous plaques," which consist of accumulated intimal smooth muscle cells laden with lipid and are surrounded by extra-cellular lipid, collagen, elastin and proteoglycans. The cells plus matrix form a fibrous cap that covers a deeper deposit of cell debris and more extra-cellular lipid. The lipid is primarily free and esterified cholesterol. A fibrous plaque forms slowly, and is likely in time to become calcified and necrotic, advancing to a "complicated lesion," which accounts for arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particularly high risk. Such independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition that occurs in the human population as a secondary symptom to various other disorders such as renal artery stenosis, pheochromocytoma or endocrine disorders. However, hypertension is also evidenced in many patients in whom the causative agent or disorder is unknown. While such "essential" hypertension is often associated with disorders such as obesity, diabetes and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure and stroke (brain hemorrhaging). These conditions are capable of causing death in a patient. Hypertension can also contribute to the development of atherosclerosis and coronary disease. These conditions gradually weaken a patient and can lead to death.

The exact cause of essential hypertension is unknown, though a number of factors are believed to contribute to the onset of the disease. Among such factors are stress, uncontrolled emotions, unregulated hormone release (the renin, angiotensin, aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus, a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure and brain hemorrhaging.

Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries while sodium retention increases blood volume. Thus, the lowering of insulin levels in hyperinsulinemics can prevent abnormal vascular growth and renal sodium retention caused by high insulin levels and thereby alleviate hypertension.

SUMMARY OF THE INVENTION

The present invention provides compounds of Formula I

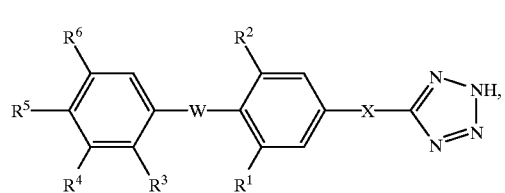

stereoisomers, pharmaceutically acceptable salts and prodrugs thereof, and pharmaceutically acceptable salts of the prodrugs, wherein:

W is O, S, SO, $SO_2$, $CH_2$, $CF_2$, CHF, C(=O), CH(OH), $NR^a$, or

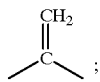

X is O, CH$_2$, CH$_2$CH$_2$, S, SO, SO$_2$, CH$_2$NR$^a$, NR$^a$, or a bond;

each R$^a$ is independently hydrogen, C$_1$–C$_6$alkyl, or C$_1$–C$_6$alkyl substituted with one substituent selected from C$_3$–C$_6$cycloalkyl or methoxy;

R$^1$, R$^2$, R$^3$ and R$^6$ are independently hydrogen, halogen, C$_1$–C$_8$alkyl, —CF$_3$, —OCF$_3$, —OC$_1$–C$_8$alkyl, or —CN;

R$^4$ is hydrogen, C$_1$–C$_{12}$alkyl, [C$_1$–C$_{12}$alkyl that is substituted with from one to three substituents independently selected from Group V], C$_2$–C$_{12}$ alkenyl, C$_2$–C$_{12}$ alkynyl, halogen, —CN, —OR$^b$, —SR$^c$, —S(=O)R$^c$, —S(=O)$_2$R$^c$, aryl, heteroaryl, C$_3$–C$_{10}$ cycloalkyl, heterocycloalkyl, —S(=O)$_2$NR$^c$R$^d$, —C(=O)NR$^c$R$^d$, —C(=O)OR$^c$, —NR$^a$C(=O)R$^d$, —NR$^a$C(=O)NR$^c$R$^d$, —NR$^a$S(=O)$_2$R$^d$, —NR$^a$R$^d$, —C(=O)R$^c$, or R$^3$ and R$^4$ may be taken together with the carbon atoms to which they are attached to form an unsubstituted or substituted carbocyclic ring of formula —(CH$_2$)$_i$— or an unsubstituted or substituted heterocyclic ring selected from the group consisting of —Q—(CH$_2$)$_j$— and —(CH$_2$)$_k$—Q—(CH$_2$)$_l$— wherein Q is O, S or NR$^a$; i is 3, 4, 5, 6 or 7; j is 2, 3, 4, 5, or 6; k and l are each independently 1, 2, 3, 4, or 5, and any substituents up to four are selected from C$_1$–C$_4$alkyl, —OR$^b$, oxo, —CN, phenyl, or —NR$^a$R$^g$;

R$^b$ is hydrogen, C$_1$–C$_{12}$alkyl, [C$_1$–C$_{12}$alkyl substituted with one to three substituents independently selected from Group V], aryl, heteroaryl, C$_3$–C$_{10}$ cycloalkyl, heterocycloalkyl, —C(=O)NR$^c$R$^d$, or R$^c$ and R$^d$ are each independently selected from hydrogen, C$_1$–C$_{12}$alkyl, [C$_1$–C$_{12}$alkyl substituted with one to three substituents independently selected from Group VI], C$_2$–C$_{12}$alkenyl, C$_2$–C$_{12}$alkynyl, aryl, heteroaryl, C$_3$–C$_{10}$ cycloalkyl, heterocycloalkyl, or R$^c$ and R$^d$ may together along with the atom(s) to which they are attached form a 3–10 membered unsubstituted or substituted heterocyclic ring, which may contain a second heterogroup selected from O, NR$^e$, or S, wherein any substituents up to four are selected from C$_1$–C$_4$alkyl, —OR$^b$, oxo, —CN, phenyl, or —C(=O)OR$^C$.

R$^5$ is —OH, —OC$_1$–C$_6$alkyl, —OC(=O)R$^f$, —F, —C(=O)OR$^c$, or R$^4$ and R$^5$ may together with the atom(s) to which they are attached form a heterocyclic ring selected from the group consisting of —CR$^c$=CR$^a$—NH—, —N=CR$^a$—NH—, —CR$^c$=CR$^a$—O—, —CR$^c$=CR$^a$—S—, —CR$^c$=N—NH—, or —CR$^a$=CR$^a$—CR$^a$=N—;

Group V is halogen, —CF$_3$, —OCF$_3$, hydroxy, oxo, C$_1$–C$_6$alkoxy, —CN, aryl, heteroaryl, C$_3$–C$_{10}$cycloalkyl, heterocycloalkyl, —SR$^f$, —S(=O)R$^f$, —S(=O)$_2$R$^f$, [—S(=O)$_2$NR$^a$R$^f$, wherein R$^a$ and R$^f$ may together along with the atom(s) to which they are attached form a 3–8 membered heterocyclic ring, which may contain a second heterogroup selected from O, NR$^e$ or S], —NR$^a$R$^g$, or [—C(=O)NR$^a$R$^f$, wherein R$^a$ and R$^f$ may together along with the atom(s) to which they are attached form a 3–8 membered heterocyclic ring, which may contain a second heterogroup selected from O, NR$^e$ or S];

Group VI is halogen, hydroxy, oxo, C$_1$–C$_6$alkoxy, aryl, heteroaryl, C$_3$–C$_8$cycloalkyl, heterocycloalkyl, —CN, or —OCF$_3$;

R$^e$ is hydrogen, —CN, C$_1$–C$_{10}$alkyl, [C$_1$–C$_{10}$alkyl substituted with one to three substituents independently selected from Group V], C$_2$–C$_{10}$alkenyl, C$_2$–C$_{10}$alkoxy, C$_3$–C$_{10}$cycloalkyl, aryl, heteroaryl, —C(=O)R$^f$, —C(=O)OR$^f$, —C(=O)NR$^a$R$^f$, —S(=O)$_2$NR$^a$R$^f$, or —S(=O)$_2$R$^f$;

R$^f$ is hydrogen, C$_1$–C$_{10}$alkyl, [C$_1$–C$_{10}$alkyl substituted with from one to three substituents selected from Group VI], C$_2$–C$_{10}$alkenyl, C$_2$–C$_{10}$alkoxy, C$_3$–C$_{10}$cycloalkyl, heterocycloalkyl, aryl, or heteroaryl; and R$^g$ is hydrogen, C$_1$–C$_6$alkyl, C$_3$–C$_8$cycloalkyl, C$_2$–C$_6$ alkenyl, aryl, —C(=O)R$^f$, —C(=O)OR$^f$, —C(=O) NR$^a$R$^f$, or —S(=O)$_2$R$^f$, provided that R$^1$ and R$^2$ are not both hydrogen, further provided that when X is CH$_2$, W is NR$^a$, R$^3$ is hydrogen and R$^5$ is —OH, then R$^6$ and R$^4$ are not both —C(CH$_3$)$_3$, further provided that when X is CH$_2$ or CH$_2$CH$_2$, W is O, and R$^3$ and R$^6$ are hydrogen, then R$^4$ is not halogen, —CF$_3$, C$_1$–C$_6$alkyl or C$_3$–C$_7$cycloalkyl, and further provided that when R$^3$ and R$^4$ are hydrogen and W is O then R$^6$ is not halogen, —CF$_3$, C$_1$–C$_6$alkyl or C$_3$–C$_7$cycloalkyl.

In a preferred embodiment of the compounds of Formula I, W is O.

In another preferred embodiment of the compounds of Formula I, X is a bond, NH, or CH$_2$.

In another preferred embodiment of the compounds of Formula I, R$^1$ and R$^2$ are independently C$_1$–C$_8$alkyl, halogen, or —CN.

In a more preferred embodiment of the compounds of Formula I, when R$^1$ and R$^2$ are independently C$_1$–C$_8$alkyl or halogen, the C$_1$–C$_8$alkyl group is —CH$_3$ and halogen group is chlorine, bromine, or iodine.

In another preferred embodiment of the compounds of Formula I, R$^6$ is hydrogen.

In another preferred embodiment of the compounds of Formula I, R$^5$ is —OH, —OC(=O)R$^f$, or —F.

In another preferred embodiment of the compounds of Formula I

W is O;

X is a bond, NH or CH$_2$;

R$^1$ and R$^2$ are independently —CH$_3$, Cl, Br, or I;

R$^6$ is hydrogen;

R$^5$ is —OH;

R$^3$ is hydrogen, halogen, C$_1$–C$_6$alkyl, —CF$_3$, —OCF$_3$, —OC$_1$–C$_6$alkyl, or —CN; and R$^4$ is hydrogen, C$_1$–C$_{12}$alkyl, [C$_1$–C$_{12}$alkyl that is substituted with from one to three substituents independently selected from Group V], C$_2$–C$_{12}$ alkenyl, C$_2$–C$_{12}$alkynyl, halogen, —CN, —OR$^b$, —SR$^c$, —S(=O)R$^c$, —S(=O)$_2$R$^c$, aryl, heteroaryl, C$_3$–C$_{10}$ cycloalkyl, heterocycloalkyl, —S(=O)$_2$NR$^c$R$^d$, —C(=O)NR$^c$R$^d$, —C(=O)OR$^c$, —NR$^a$C(=O)R$^d$, —NR$^a$C(=O)NR$^c$R$^d$, —NR$^a$S(=O)$_2$R$^d$, —NR$^a$R$^d$, wherein aryl is phenyl or naphthyl either unsubstituted or substituted with from one to four substituents selected from halogen, C$_1$–C$_4$alkyl, C$_1$–C$_4$alkoxy, —OCF$_3$, —CN, —SR$^f$, —S(=O)R$^f$, —S(=O)$_2$R$^f$, C$_3$–C$_6$cycloalkyl, —S(=O)$_2$NR$^a$R$^f$, —NR$^a$R$^g$, —C(=O)NR$^a$R$^f$, —OH, or C$_1$–C$_4$perfluoroalkyl; wherein heteroaryl is an unsubstituted, monosubstituted or disubstituted five or six membered aromatic ring having from 1 to 3 heteroatoms independently selected from O, N, or S, and wherein any substituents are selected from halogen, C$_1$–C$_4$alkyl, C$_1$–C$_4$alkoxy, —CF$_3$, —OH, —NR$^a$R$^g$, —CO$_2$R$^f$, or form a fused benzo group; and heterocycloalkyl is either unsubstituted or substituted with from one to four substituents selected from C$_1$–C$_4$ alkyl, —OH, oxo, C$_1$–C$_4$alkoxy, —CN, phenyl, or NR$^a$R$^e$, or R$^3$ and R$^4$ may be taken together with the carbon atoms to which they are attached to form a carbocyclic ring of formula —(CH$_2$)$_i$— or a heterocyclic ring selected from the group consisting of —Q—(CH$_2$)$_j$— and —(CH$_2$)$_k$—Q—(CH$_2$)$_l$— wherein Q is O, S or NR$^a$; i is 3, 4, 5, 6 or 7; j is 2, 3, 4, 5, or 6; k, and l are each independently 1, 2, 3, 4, or 5.

The present invention provides compounds of Formula I

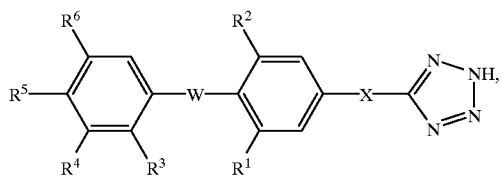

stereoisomers, pharmaceutically acceptable salts and prodrugs thereof, and pharmaceutically acceptable salts of the prodrugs, wherein:

W is O;

X is a bond or NH;

R$^1$ and R$^2$ are independently halogen or C$_1$–C$_8$alkyl;

R$^3$ and R$^6$ are hydrogen;

R$^5$ is —OH;

R$^4$ is C$_1$–C$_8$ alkyl, —S(=O)$_2$NR$^c$R$^d$, —C(=O)NR$^c$R$^d$ or —S(=O)$_2$R$^c$; and R$^c$ and R$^d$ are independently hydrogen, C$_1$–C$_{12}$alkyl, C$_3$–C$_{10}$cycloalkyl, —S(=O)$_2$R$^c$, or substituted cycloalkyl, heterocycloalkyl, aryl, or heteroaryl, or R$^c$ and R$^d$ taken together with the nitrogen atom to which they are attached form a heterocycloalkyl ring or a substituted heterocycloalkyl ring.

The present invention provides the compounds:
4-[2,6-dimethyl-4-(2H-tetrazol-5-yl)-phenoxy]-2-isopropyl-phenol;
4-[2,6-dichloro-4-(1H-tetrazol-5-yl)-phenoxy]-2-isopropyl-phenol;
4-[2,6-dichloro-4-(2H-tetrazol-5-yl)-phenoxy]-2-(pyrrolidine-1-sulfonyl)-phenol;
4-[2,6-dichloro-4-(2H-tetrazol-5-yl)-phenoxy]-2-(piperidine-1-sulfonyl)-phenol;
4-[2,6-dichloro-4-(2H-tetrazol-5-yl)-phenoxy]-2-(3,3-dimethyl-piperidine-1-sulfonyl)-phenol;
N-cyclopropyl-5-[2,6-dichloro-4-(2H-tetrazol-5-yl)-phenoxy]-2-hydroxy-benzenesulfonamide;
5-[2,6-dichloro-4-(2H-tetrazol-5-yl)-phenoxy]-2-hydroxy-N,N-dimethyl-benzenesulfonamide;
{5-[2,6-dichloro-4-(1H-tetrazol-5-yl)-phenoxy]-2-hydroxy-phenyl}-piperidin-1-yl-methanone;
N-cyclobutyl-5-[2,6-dichloro-4-(1H-tetrazol-5-yl)-phenoxy]-2-hydroxy-benzamide;
N-cyclohexyl-5-[2,6-dichloro-4-(1H-tetrazol-5-yl)-phenoxy]-2-hydroxy-benzamide;
{5-[2,6-dichloro-4-(1H-tetrazol-5-yl)-phenoxy]-2-hydroxy-phenyl}-pyrrolidin-1-yl-methanone;
N-bicyclo[2.2.1]hept-2-yl-5-[2,6-dichloro-4-(1H-tetrazol-5-yl)-phenoxy]-2-hydroxy-benzamide;
4-[2,6-dimethyl-4-(1H-tetrazol-5-ylamino)-phenoxy]-2-isopropyl-phenol;
5-[2-chloro-6-methyl-4-(1H-tetrazol-5-ylamino)-phenoxy]-N-cyclopropyl-2-hydroxy-benzenesulfonamide;
N-cyclopropyl-5-[2,6-dichloro-4-(1H-tetrazol-5-ylamino)-phenoxy]-2-hydroxy-benzenesulfonamide;
N-cyclobutyl-5-[2,6-dimethyl-4-(1H-tetrazol-5-ylamino)-phenoxy]-2-hydroxy-N-methyl-benzamide;
2-cyclopropylmethanesulfonyl-4-[2,6-dimethyl-4-(1H-tetrazol-5-ylamino)-phenoxy]-phenol; and stereoisomers, pharmaceutically acceptable salts and prodrugs thereof, and pharmaceutically acceptable salts of the prodrugs.

The present invention also provides the compounds:
2-cyclobutylmethanesulfonyl-4-[2,6-dimethyl-4-(2H-tetrazol-5-ylamino)-phenoxy]-phenol;
2-cyclobutylmethanesulfonyl-4-[2,6-dichlorol-4-(2H-tetrazol-5-ylamino)-phenoxy]-phenol;
4-[2-chloro-6-methyl-4-(2H-tetrazol-5-ylamino)-phenoxy]-2-cyclobutylmethanesulfonyl-phenol;
2-cyclopentylmethanesulfonyl-4-[2,6-dimethyl-4-(2H-tetrazol-5-ylamino)-phenoxy]-phenol;
2-cyclopentylmethanesulfonyl-4-[2,6-dichlorol-4-(2H-tetrazol-5-ylamino)-phenoxy]-phenol;
4-[2-chloro-6-methyl-4-(2H-tetrazol-5-ylamino)-phenoxy]-2-cyclopentylmethanesulfonyl-phenol;
2-cyclohexylmethanesulfonyl-4-[2,6-dimethyl-4-(2H-tetrazol-5-ylamino)-phenoxy]-phenol;
2-cyclohexylmethanesulfonyl-4-[2,6-dichlorol-4-(2H-tetrazol-5-ylamino)-phenoxy]-phenol;
4-[2-chloro-6-methyl-4-(2H-tetrazol-5-ylamino)-phenoxy]-2-cyclohexylmethanesulfonyl-phenol;
4-[2,6-dimethyl-4-(2H-tetrazol-5-ylamino)-phenoxy]-2-(4-fluorobenzenesulfonyl)-phenol;
4-[2,6-dichloro-4-(2H-tetrazol-5-ylamino)-phenoxy]-2-(4-fluorobenzenesulfonyl)-phenol;
4-[2-chloro-6-methyl-4-(2H-tetrazol-5-ylamino)-phenoxy]-2-(4-fluorobenzenesulfonyl)-phenol;
5-[2,6-dichloro-4-(2H-tetrazol-5-ylamino)-phenoxyl]-2-hydroxy-N-methyl-benzamide;
N-butyl-5-[2,6-dichloro-4-(2H-tetrazol-5-ylamino)-phenoxy]-2-hydroxy-benzamide;
5-[2,6-dichloro-4-(2H-tetrazol-5-ylamino)-phenoxy]-2-hydroxy-N-isopropyl-benzamide;
5-[2,6-dichloro-4-(2H-tetrazol-5-ylamino)-phenoxy]-N-heptyl-2-hydroxy-benzamide;
5-[2,6-dichloro-4-(2H-tetrazol-5-ylamino)-phenoxy]-2-hydroxy-N-nonylbenzamide;
5-[2,6-dichloro-4-(2H-tetrazol-5-ylamino)-phenoxy]-N-(4-fluoro-phenyl)-2-hydroxy-benzamide;
N-cyclopentyl-5-[2,6-dichloro-4-(2H-tetrazol-5-ylamino)-phenoxy]-2-hydroxy-benzamide;
N-cyclohexyl-5-[2,6-dichloro-4-(2H-tetraol-5-ylamino)-phenoxy]-2-hydroxy-benzamide;
N-cycloheptyl-5-[2,6-dichloro-4-(2H-tetrazol-5-ylamino)-phenoxy]-2-hydroxy-benzamide;
N-cyclooctyl-5-[2,6-dichloro-4-(2H-tetrazol-5-ylamino)-phenoxy]-2-hydroxy-benzamide;
5-[2,6-dichloro-4-(2H-tetrazol-5-ylamino)-phenoxy]-2-hydroxy-N-(1-isopropyl-2-methyl-propyl)-benzamide;
N-cyclohexylmethyl-5-[2,6-dichloro-4-(2H-tetrazol-5-ylamino)-phenoxy]-2-hydroxy-benzamide;
N-(R-1-cyclohexyl-ethyl)-5-[2,6-dichloro-4-(2H-tetrazol-5-ylamino)-phenoxy]-2-hydroxy-benzamide;

N-(S-1-cyclohexyl-ethyl)-5-[2,6-dichloro-4-(1H-tetrazol-5-ylamino)-phenoxy]-2-hydroxy-benzamide;
N-cyclopentyl-5-[2,6-dichloro-4-(2H-tetrazol-5-ylamino)-phenoxy]-2-hydroxy-N-methyl-benzamide;
N-cyclohexyl-5-[2,6-dichloro-4-(2H-tetrazol-5-ylamino)-phenoxy-2-hydroxy-N-methyl-benzamide;
N-cycloheptyl-5-[2,6-dichloro-4-(2H-tetrazol-5-ylamino)-phenoxy]-2-hydroxy-N-methyl-benzamide;
N-cyclooctyl-5-[2,6-dichloro-4-(2H-tetrazol-5-ylamino)-phenoxy]-2-hydroxy-N-methyl-benzamide;
5-[2,6-dichloro-4-(2H-tetrazol-5-ylamino)-phenoxy]-2-hydroxy-N-(1-isopropyl-2-methyl-propyl)-N-methyl-benzamide;
N-cyclohexylmethyl-5-[2,6-dichloro-4-(2H-tetrazol-5-ylamino)-phenoxy]-2-hydroxy-N-methyl-benzamide;
N-(R-1-cyclohexyl-ethyl)-5-[2,6-dichloro-4-(2H-tetrazol-5-ylamino)-phenoxy]-2-hydroxy-N-methyl-benzamide;
N-(S-1-cyclohexyl-ethyl)-5-[2,6-dichloro-4-(1H-tetrazol-5-ylamino)-phenoxy]-2-hydroxy-N-methyl-benzamide; and stereoisomers, pharmaceutically acceptable salts and prodrugs thereof, and pharmaceutically acceptable salts of the prodrugs.

Also provided are methods of treating diabetes, the methods comprising the step of administering to a patient having or at risk of having diabetes, a therapeutically effective amount of a compound of Formula I, stereoisomers, pharmaceutically acceptable salts and prodrug thereof, and pharmaceutically acceptable salts of the prodrugs.

In a preferred embodiment of the method of treating diabetes, the diabetes is Type I diabetes.

In a preferred embodiment of the method of treating diabetes, the diabetes is Type II diabetes.

Also provided are methods of treating atherosclerosis, the methods comprising the step of administering to a patient having or at risk of having atherosclerosis, a therapeutically effective amount of a compound of Formula I, stereoisomers, pharmaceutically acceptable salts and prodrugs thereof, and pharmaceutically acceptable salts of the prodrugs.

Also provided are methods of treating hypertension, the methods comprising the step of administering to a patient having or at risk of having hypertension, a therapeutically effective amount of a compound of Formula I, stereoisomers, pharmaceutically acceptable salts and prodrugs thereof, and pharmaceutically acceptable salts of the prodrugs.

Also provided are methods of treating coronary heart disease, the methods comprising the step of administering to a patient having or at risk of having coronary heart disease, a therapeutically effective amount of a compound of Formula I, stereoisomers, pharmaceutically acceptable salts and prodrugs thereof, and pharmaceutically acceptable salts of the prodrugs.

Also provided are methods of treating hypercholesterolemia, the method comprising the step of administering to a patient having or at risk of having hypercholesterolemia, a therapeutically effective amount of a compound of Formula I, stereoisomers, pharmaceutically acceptable salts or prodrugs thereof, and pharmaceutically acceptable salts of the prodrugs.

Also provided are methods of treating hyperlipidemia, the methods comprising the step of administering to a patient having or at risk of having hyperlipidemia, a therapeutically effective amount of a compound of Formula I, stereoisomers, pharmaceutically acceptable salts and prodrugs thereof, and pharmaceutically acceptable salts of the prodrugs.

Also provided are methods of treating thyroid disease, the methods comprising the step of administering to a patient having or at risk of having thyroid disease, a therapeutically effective amount of a compound of Formula I, stereoisomers, pharmaceutically acceptable salts and prodrugs thereof, and pharmaceutically acceptable salts of the prodrugs.

Also provided are methods of treating hypothyroidism, the methods comprising the step of administering to a patient having or at risk of having hypothyroidism, a therapeutically effective amount of a compound of Formula I, stereoisomers, pharmaceutically acceptable salts and prodrugs thereof, and pharmaceutically acceptable salts of the prodrugs.

Also provided are methods of treating depression, the methods comprising the step of administering to a patient having or at risk of having depression, a therapeutically effective amount of a compound of Formula I, stereoisomers, pharmaceutically acceptable salts and prodrugs thereof, and pharmaceutically acceptable salts of the prodrugs.

Also provided are methods of treating obesity, the methods comprising the step of administering to an obese patient or a patient at risk of becoming obese, a therapeutically effective amount of a compound of Formula I, stereoisomers, pharmaceutically acceptable salts and prodrugs thereof, and pharmaceutically acceptable salts of the prodrugs.

Also provided are methods of treating osteoporosis, the methods comprising the step of administering to a patient having or at risk of having osteoporosis, a therapeutically effective amount of a compound of Formula I, stereoisomers, pharmaceutically acceptable salts and prodrugs thereof, and pharmaceutically acceptable salts of the prodrugs.

Also provided are methods of treating thyroid cancer, the method comprising the step of administering to a patient having or at risk of having thyroid cancer, a therapeutically effective amount of a compound of Formula I, stereoisomers, pharmaceutically acceptable salts and prodrugs thereof, and pharmaceutically acceptable salts of the prodrugs.

Also provided are methods of treating glaucoma, the methods comprising the step of administering to a patient having or at risk of having glaucoma, a therapeutically effective amount of a compound of Formula I, stereoisomers, pharmaceutically acceptable salts and prodrugs thereof, and pharmaceutically acceptable salts of the prodrugs.

Also provided are methods of treating cardiac arrhythmias, the methods comprising the step of administering to a patient having or at risk of having cardiac arrhythmias, a therapeutically effective amount of a compound of Formula I, stereoisomers, pharmaceutically acceptable salts and prodrugs thereof, and pharmaceutically acceptable salts of the prodrugs.

Also provided are methods of treating congestive heart failure, the methods comprising the step of administering to a patient having or at risk of having congestive heart failure, a therapeutically effective amount of a compound of Formula I, stereoisomers, pharmaceutically acceptable salts and prodrugs thereof, and pharmaceutically acceptable salts of the prodrugs.

Also provided are methods of increasing energy expenditure, the methods comprising the step of administering to a patient who needs an energy expenditure increase a therapeutically effective amount of a compound of Formula I, or a stereoisomer, pharmaceutically acceptable salt or prodrug thereof, or a pharmaceutically acceptable salt of the prodrug.

Also provided are pharmaceutical compositions comprising a compound of Formula I, stereoisomers, pharmaceutically acceptable salts and prodrugs thereof, and pharmaceutically acceptable salts of the prodrugs.

Also provided are kits for the treatment of obesity, diabetes, atherosclerosis, hypertension, coronary heart disease, hypercholesterolemia, hyperlipidemia, thyroid disease, thyroid cancer, hypothyroidism, depression, glaucoma, cardiac arrhythmias, congestive heart failure, or osteoporosis, the kits comprising:

a) a first pharmaceutical composition comprising a compound of Formula I, stereoisomers, pharmaceutically acceptable salts and prodrugs thereof, and pharmaceutically acceptable salts of the prodrugs;

b) a second pharmaceutical composition comprising an additional compound useful for the treatment of obesity, diabetes, atherosclerosis, hypertension, coronary heart disease, hypercholesterolemia, hyperlipidemia, thyroid disease, thyroid cancer, hypothyroidism, depression, glaucoma, cardiac arrhythmias, congestive heart failure, or osteoporosis; and c) a container for containing the first and second compositions.

Also provided are methods of treating obesity, diabetes, atherosclerosis, hypertension, coronary heart disease, hypercholesterolemia, hyperlipidemia, thyroid disease, thyroid cancer, hypothyroidism, depression, glaucoma, cardiac arrhythmias, congestive heart failure, or osteoporosis, the methods comprising the step of administering to an obese patient, a patient at risk of becoming obese, or a patient having or at risk of having diabetes, atherosclerosis, hypertension, coronary heart disease, hypercholesterolemia, hyperlipidemia, thyroid disease, thyroid cancer, hypothyroidism, depression, glaucoma, cardiac arrhythmias, congestive heart failure, or osteoporosis a therapeutically effective amount of 1) a compound of Formula I, stereoisomers, pharmaceutically acceptable salts or prodrugs thereof, and pharmaceutically acceptable salts of the prodrugs and 2) an additional compound useful for treating obesity, diabetes, atherosclerosis, hypertension, coronary heart disease, hypercholesterolemia, hyperlipidemia, thyroid disease, thyroid cancer, hypothyroidism, depression, glaucoma, cardiac arrhythmias, congestive heart failure, or osteoporosis.

Also provided are pharmaceutical compositions comprising a compound of Formula I, stereoisomers, pharmaceutically acceptable salts and prodrugs thereof, and pharmaceutically acceptable salts of the prodrugs, and an additional compound useful to treat obesity, diabetes, atherosclerosis, hypertension, coronary heart disease, hypercholesterolemia, hyperlipidemia, thyroid disease, thyroid cancer, hypothyroidism, depression, glaucoma, cardiac arrhythmias, congestive heart failure, or osteoporosis.

DETAILED DESCRIPTION OF THE INVENTION

The present invention relates to compounds of Formula I, pharmaceutically acceptable salts of the compounds of Formula I, prodrugs of the compounds of Formula I, and pharmaceutically acceptable salts of the prodrugs of compounds of Formula I. This invention also relates to methods of treating of obesity, diabetes, atherosclerosis, hypertension, coronary heart disease, hypercholesterolemia, hyperlipidemia, thyroid disease, thyroid cancer, hypothyroidism, depression, glaucoma, cardiac arrhythmias (including atrial and ventricular arrhythmias), congestive heart failure, and osteoporosis. This invention also relates to pharmaceutical compositions and kits.

The term "alkyl" means a straight or branched chain hydrocarbon. Representative examples of alkyl groups include methyl, ethyl, propyl, isopropyl, butyl, isobutyl, tert-butyl, sec-butyl, pentyl, and hexyl. Preferred alkyl groups are $C_1$–$C_{12}$alkyl.

The term "alkoxy" means an alkyl group bonded to an oxygen atom. Representative examples of alkoxy groups include methoxy, ethoxy, tert-butoxy, propoxy, and isobutoxy. Preferred alkoxy groups are $C_1$–$C_{12}$alkoxy.

The term "halogen" means chlorine, fluorine, bromine, or iodine.

The term "alkenyl" means a branched or straight chain hydrocarbon having one or more carbon-carbon double bonds.

The term "alkynyl" means a branched or straight chain hydrocarbon having one or more carbon-carbon triple bonds.

The term "cycloalkyl" means a cyclic hydrocarbon. Examples of cycloalkyl groups include cyclopropyl, cyclobutyl, cyclopentyl, cyclohexyl, and cycloheptyl. Preferred cycloalkyl groups are $C_3$–$C_{10}$cyloalkyl. It is also possible for the cycloalkyl group to have one or more double bonds or triple bonds, or a combination of double bonds and triple bonds, but is not aromatic. Examples of cycloalkyl groups having a double or triple bond include cyclopentenyl, cyclohexenyl, cyclohexadienyl, cyclobutadienyl, and the like. It is also noted that the term cycloalkyl includes polycyclic compounds such as bicyclic or tricyclic compounds. The cycloalkyl groups may be substituted or unsubsituted with from one to four substitutents. Examples of substitutents that are suitable are recited below under the definitions of aryl, heteroaryl and substituents.

The term "perfluoroalkyl" means an alkyl group in which all of the hydrogen atoms have been replaced with fluorine atoms.

The term "acyl" means a group derived from an organic acid (—COOH) by removal of the hydroxy group (—OH).

The term "aryl" means a cyclic, aromatic hydrocarbon. Examples of aryl groups include phenyl and naphthyl. The aryl group can be unsubstituted or substituted. Examples of preferred substituents include halogen, $C_1$–$C_4$alkyl, $C_1$–$C_4$alkoxy, —OCF$_3$, —CN, —SR$^f$, —S(=O)R$^f$, —S(=O)$_2$R$^f$, $C_3$–$C_6$cycloalkyl, —S(=O$_2$)NR$^a$R$^f$, —NR$^a$R$^g$, —C(=O)NR$^a$R$^f$, —OH, or $C_1$–$C_4$perfluoroalkyl, where R$^a$, R$^f$, and R$^g$ are as defined herein.

The term "heteroatom" includes oxygen, nitrogen, sulfur, and phosphorous.

The term "heteroaryl" means a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b] thienyl. Preferred heteroaryl groups are five and six membered rings and contain from one to three heteroatoms selected from O, N, and S. The heteroaryl group can be unsubstituted or substituted with from 1 to 4 substituents. Examples of preferred substituents include halogen, $C_1$–$C_4$alkyl, $C_1$–$C_4$alkoxy, —$CF_3$, —OH, —$NR^aR^e$, —$CO_2R^f$ or a fused benzo group, where $R^a$, $R^c$, and $R^f$ are as defined herein.

The term "heterocycloalkyl" mean a cycloalkyl group in which one or more of the carbon atoms has been replaced with heteroatoms. If the heterocycloalkyl group contains more than one heteroatom, the heteroatoms may be the same or different. Examples of heterocycloalkyl groups include tetrahydrofuryl, morpholinyl, piperazinyl, piperidyl, and pyrrolidinyl. Preferred heterocycloalkyl groups are five and six membered rings and contain from one to three heteroatoms. It is also possible for the heterocycloalkyl group to have one or more double bonds or triple bonds or a combination of double bonds and triple bonds, but is not aromatic. Examples of heterocycloalkyl groups containing double or triple bonds include dihydrofuran, and the like. A heterocycloalkyl group can be unsubstituted or substituted with from 1 to 4 substituents. Examples of preferred substituents include $C_1$–$C_4$alkyl, —OH, oxo, $C_1$–$C_4$alkoxy, —CN, phenyl, or —$NR^aR^e$, where $R^a$ and $R^e$ are as defined herein.

It is also noted that the cyclic ring groups, i.e., aryl, heteroaryl, cycloalkyl, heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4-oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, taken independently, optionally having one to four heteroatoms are indolizinyl, indolyl, isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule has been replaced with a different atom or molecule. The atom or molecule replacing the hydrogen atom is called a substituent. Examples of suitable substituents include, halogens, —$OC_1$–$C_8$alkyl, —$C_1$–$C_8$alkyl, —$C_2$–$C_6$alkenyl, —$C_3$–$C_8$cycloalkyl, heterocycloalkyl, —$CF_3$, —$OCF_3$, —$NH_2$, —$NHC_1$–$C_8$alkyl, —$N(C_1$–$C_8$alkyl$)_2$, —$NO_2$, —CN, —$CO_2H$, —$CO_2C_1$–$C_8$alkyl, and the like.

The symbol "—" represents a covalent bond.

The phrase "therapeutically effective amount" means an amount of a compound or combination of compounds that ameliorates, attenuates, or eliminates one or more symptoms of a particular disease or condition or prevents or delays the onset of one of more symptoms of a particular disease or condition.

The term "patient" means animals, such as dogs, cats, cows, horses, sheep, and humans. Particularly preferred patients are mammals, including both males and females.

The phrase "pharmaceutically acceptable" means that the substance or composition must be compatible with the other ingredients of a formulation, and not deleterious to the patient.

The phrases "a compound of the present invention, a compound of Formula I, or a compound in accordance with Formula I" and the like, include the pharmaceutically acceptable salts of the compounds, prodrugs of the compounds, and pharmaceutically acceptable salts of the prodrugs.

The phrase "reaction-inert solvent" or "inert solvent" refer to a solvent or mixture of solvents that does not interact with starting materials, reagents, intermediates or products in a manner that adversely affects the desired product.

The terms "treating", "treat" or "treatment" include preventative (e.g., prophylactic) and palliative treatment.

The characteristics of patients at risk of having atherosclerosis are well known to those in the art and include patients who have a family history of cardiovascular disease, including hypertension and atherosclerosis, obese patients, patients who exercise infrequently, patients with hypercholesterolemia, hyperlipidemia and/or hypertriglyceridemia, patients having high levels of LDL or Lp(a), patients having low levels of HDL, and the like.

In one aspect, the present invention concerns the treatment of diabetes, including impaired glucose tolerance, insulin resistance, insulin dependent diabetes mellitus (Type I) and non-insulin dependent diabetes mellitus (NIDDM or Type II). Also included in the treatment of diabetes are the diabetic complications, such as neuropathy, nephropathy, retinopathy or cataracts.

The preferred type of diabetes to be treated by the compounds of the present invention is non-insulin dependent diabetes mellitus, also known as Type II diabetes or NIDDM.

Diabetes can be treated by administering to a patient having diabetes (Type I or Type II), insulin resistance, impaired glucose tolerance, or any of the diabetic complications such as neuropathy, nephropathy, retinopathy or cataracts, a therapeutically effective amount of a compound of the present invention. It is also contemplated that diabetes be treated by administering a compound of the present invention along with other agents that can be used to treat diabetes.

Representative agents that can be used to treat diabetes in combination with a compound of the present invention include insulin and insulin analogs (e.g. LysPro insulin); GLP-1 (7-37) (insulinotropin) and GLP-1 (7-36)—$NH_2$; sulfonylureas and analogs: chlorpropamide, glibenclamide, tolbutamide, tolazamide, acetohexamide, glypizide, glimepiride, repaglinide, meglitinide; biguanides: metformin, phenformin, buformin; α2-antagonists and imidazolines: midaglizole, isaglidole, deriglidole, idazoxan, efaroxan, fluparoxan; other insulin secretagogues: linogliride, A-4166; glitazones: ciglitazone, pioglitazone, englitazone, troglitazone, darglitazone, BRL49653; fatty acid oxidation inhibitors: clomoxir, etomoxir; α-glucosidase inhibitors: acarbose, miglitol, emiglitate, voglibose, MDL-25,637, camiglibose, MDL-73,945; β-agonists: BRL 35135, BRL 37344, RO 16-8714, ICI D7114, CL 316,243; phosphodiesterase inhibitors: L-386,398; lipid-lowering agents: benfluorex; antiobesity agents: fenfluramine; vanadate and vanadium complexes (e.g. Naglivan®) and peroxovanadium complexes; amylin antagonists; glucagon antagonists; gluconeogenesis inhibitors; somatostatin analogs; antilipolytic agents: nicotinic acid, acipimox, WAG 994. Also contemplated to be used in combination with a compound of the present invention are pramlintide (symlin™), AC 2993 and nateglinide. Any agent or combination of agents can be administered as described above.

In addition, the compounds of the present invention can be used in combination with one or more aldose reductase inhibitors, glycogen phosphorylase inhibitors, sorbitol dehydrogenase inhibitors, NHE-1 inhibitors and/or glucocorticoid receptor antagonists.

The compounds of the present invention can be used in combination with an aldose reductase inhibitor. Aldose reductase inhibitors constitute a class of compounds that have become widely known for their utility in preventing and treating conditions arising from complications of diabetes, such as diabetic neuropathy and nephropathy. Such compounds are well known to those skilled in the art and are readily identified by standard biological tests. For example, the aldose reductase inhibitor zopolrestat, 1-phthalazineacetic acid, 3,4-dihydro-4-oxo-3-[[5-(trifluoromethyl)-2-benzothiazolyl]methyl]-, and related compounds are described in U.S. Pat. No. 4,939,140 to Larson et al.

Aldose reductase inhibitors have been taught for use in lowering lipid levels in mammals. See, for example, U.S. Pat. No. 4,492,706 to Kallai-sanfacon and EP 0 310 931 A2 (Ethyl Corporation).

U.S. Pat. No. 5,064,830 to Going discloses the use of certain oxophthalazinyl acetic acid aldose reductase inhibitors, including zopolrestat, for lowering of blood uric acid levels.

Commonly assigned U.S. Pat. No. 5,391,551 discloses the use of certain aldose reductase inhibitors, including zopolrestat, for lowering blood lipid levels in humans. The disclosure teaches that therapeutic utilities derive from the treatment of diseases caused by an increased level of triglycerides in the blood, such diseases include cardiovascular disorders such as thrombosis, arteriosclerosis, myocardial infarction, and angina pectoris. A preferred aldose reductase inhibitor is zopolrestat.

The term aldose reductase inhibitor refers to compounds that inhibit the bioconversion of glucose to sorbitol, which is catalyzed by the enzyme aldose reductase.

Any aldose reductase inhibitor may be used in a combination with a compound of the present invention. Aldose reductase inhibition is readily determined by those skilled in the art according to standard assays (J. Malone, *Diabetes*, 29:861–864 (1980) "Red Cell Sorbitol, an Indicator of Diabetic Control"). A variety of aldose reductase inhibitors are described herein; however, other aldose reductase inhibitors useful in the compositions and methods of this invention will be known to those skilled in the art.

The activity of an aldose reductase inhibitor in a tissue can be determined by testing the amount of aldose reductase inhibitor that is required to lower tissue sorbitol (i.e., by inhibiting the further production of sorbitol consequent to blocking aldose reductase) or lower tissue fructose (by inhibiting the production of sorbitol consequent to blocking aldose reductase and consequently the production of fructose).

Accordingly, additional examples of aldose reductase inhibitors useful in the compositions, combinations and methods of the present invention include:

1. 3-(4-bromo-2-fluorobenzyl)-3,4-dihydro-4-oxo-1-phthalazineacetic acid (ponalrestat, U.S. Pat. No. 4,251,528);
2. N[[(5-trifluoromethyl)-6-methoxy-1-naphthalenyl]thioxomethyl]-N-methylglycine (tolrestat, U.S. Pat. No. 4,600,724);
3. 5-[(Z,E)-β-methylcinnamylidene]-4-oxo-2-thioxo-3-thiazolideneacetic acid (epalrestat, U.S. Pat. No. 4,464,382, U.S. Pat. No. 4,791,126, U.S. Pat. No. 4,831,045);
4. 3-(4-bromo-2-fluorobenzyl)-7-chloro-3,4-dihydro-2,4-dioxo-1(2H)-quinazolineacetic acid (zenarestat, U.S. Pat. Nos. 4,734,419, and 4,883,800);
5. 2R,4R-6,7-dichloro-4-hydroxy-2-methylchroman-4-acetic acid (U.S. Pat. No. 4,883,410);
6. 2R,4R-6,7-dichloro-6-fluoro-4-hydroxy-2-methylchroman-4-acetic acid (U.S. Pat. No. 4,883,410);
7. 3,4-dihydro-2,8-diisopropyl-3-oxo-2H-1,4-benzoxazine-4-acetic acid (U.S. Pat. No. 4,771,050);
8. 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572);
9. N-[3,5-dimethyl-4-[(nitromethyl)sulfonyl]phenyl]-2-methyl-benzeneacetamide (ZD5522, U.S. Pat. No. 5,270,342 and U.S. Pat. No. 5,430,060);
10. (S)-6-fluorospiro[chroman-4,4'-imidazolidine]-2,5'-dione (sorbinil, U.S. Pat. No. 4,130,714);
11. d-2-methyl-6-fluoro-spiro(chroman-4',4'-imidazolidine)-2',5'-dione (U.S. Pat. No. 4,540,704);
12. 2-fluoro-spiro(9H-fluorene-9,4'-imidazolidine)2',5'-dione (U.S. Pat. No. 4,438,272);
13. 2,7-di-fluoro-spiro(9H-fluorene-9,4'-imidazolidine)2',5'-dione (U.S. Pat. No. 4,436,745, U.S. Pat. No. 4,438,272);
14. 2,7-di-fluoro-5-methoxy-spiro(9H-fluorene-9,4'-imidazolidine)2',5'-dione (U.S. Pat. No. 4,436,745, U.S. Pat. No. 4,438,272);

15. 7-fluoro-spiro(5H-indenol[1,2-b]pyridine-5,3'-pyrrolidine)2,5'-dione (U.S. Pat. No. 4,436,745, U.S. Pat. No. 4,438,272);
16. d-cis-6'-chloro-2',3'-dihydro-2'-methyl-spiro-(imidazolidine-4,4'-4'-H-pyrano(2,3-b)pyridine)-2,5-dione (U.S. Pat. No. 4,980,357);
17. spiro[imidazolidine-4,5'(6H)-quinoline]2,5-dione-3'-chloro-7,'8'-dihydro-7'-methyl-(5'-cis)(U.S. Pat. No. 5,066,659);
18. (2S,4S)-6-fluoro-2',5'-dioxospiro(chroman-4,4'-imidazolidine)-2-carboxamide (U.S. Pat. No. 5,447,946); and
19. 2-[(4-bromo-2-fluorophenyl)methyl]-6-fluorospiro[isoquinoline-4(1H),3'-pyrrolidine]-1,2',3,5'(2H)-tetrone (ARI-509, U.S. Pat. No. 5,037,831).

Other aldose reductase inhibitors include compounds having formula Ia below

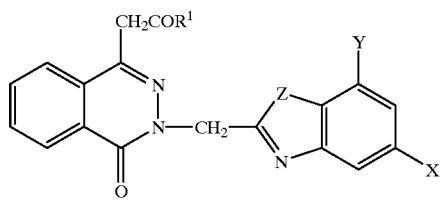

and pharmaceutically acceptable salts and prodrugs thereof, wherein

Z is O or S;

$R^1$ is hydroxy or a group capable of being removed in vivo to produce a compound of formula I wherein $R^1$ is OH; and X and Y are the same or different and are selected from hydrogen, trifluoromethyl, fluoro, and chloro.

A preferred subgroup within the above group of aldose reductase inhibitors includes numbered compounds 1, 2, 3, 4, 5, 6, 9, 10, and 17, and the following compounds of Formula Ia:

20. 3,4-dihydro-3-(5-fluorobenzothiazol-2-ylmethyl)-4-oxophthalazin-1-yl-acetic acid [$R^1$=hydroxy; X=F; Y=H];
21. 3-(5,7-difluorobenzothiazol-2-ylmethyl)-3,4-dihydro-4-oxophthalazin-1-ylacetic acid [$R^1$=hydroxy; X=Y=F];
22. 3-(5-chlorobenzothiazol-2-ylmethyl)-3,4-dihydro-4-oxophthalazin-1-ylacetic acid [$R^1$=hydroxy; X=Cl; Y=H];
23. 3-(5,7-dichlorobenzothiazol-2-ylmethyl)-3,4-dihydro-4-oxophthalazin-1-ylacetic acid [$R^1$=hydroxy; X=Y=Cl];
24. 3,4-dihydro-4-oxo-3-(5-trifluoromethylbenzoxazol-2-ylmethyl)phthalazin-1-ylacetic acid [$R^1$=hydroxy; X=CF_3; Y=H];
25. 3,4-dihydro-3-(5-fluorobenzoxazol-2-ylmethyl)-4-oxophthalazin-1-yl-acetic acid [$R^1$=hydroxy; X=F; Y=H];
26. 3-(5,7-difluorobenzoxazol-2-ylmethyl)-3,4-dihydro-4-oxophthalazin-1-ylacetic acid [$R^1$=hydroxy; X=Y=F];
27. 3-(5-chlorobenzoxazol-2-ylmethyl)-3,4-dihydro-4-oxophthalazin-1-ylacetic acid [$R^1$=hydroxy; X=Cl; Y=H];
28. 3-(5,7-dichlorobenzoxazol-2-ylmethyl)-3,4-dihydro-4-oxophthalazin-1-ylacetic acid [$R^1$=hydroxy; X=Y=Cl]; and
29. zopolrestat; 1-phthalazineacetic acid, 3,4-dihydro-4-oxo-3-[[5-(trifluoromethyl)-2-benzothiazolyl]methyl]-[$R^1$=hydroxy; X=trifluoromethyl; Y=H].

In compounds 20–23, and 29 Z is S. In compounds 24–28, Z is O.

Of the above subgroup, compounds 20–29 are more preferred with 29 especially preferred. Procedures for making the aldose reducatase inhibitors of formula Ia can be found in PCT publication number WO 99/26659.

The compounds of the present invention can also be used in combination with a glucocorticoid receptor antagonist. The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and $NF_\kappa$-β. Such interactions result in inhibition of API- and $NF_\kappa$-β-mediated transcription and are believed to be responsible for the anti-inflammatory activity of endogenously administered glucocorticoids. In addition, glucocorticoids may also exert physiologic effects independent of nuclear transcription. Biologically relevant glucocorticoid receptor agonists include cortisol and corticosterone. Many synthetic glucocorticoid receptor agonists exist including dexamethasone, prednisone and prednisilone. By definition, glucocorticoid receptor antagonists bind to the receptor and prevent glucocorticoid receptor agonists from binding and eliciting GR mediated events, including transcription. RU486 is an example of a non-selective glucocorticoid receptor antagonist. GR antagonists can be used in the treatment of diseases associated with an excess or a deficiency of glucocorticoids in the body. As such, they may be used to treat the following: obesity, diabetes, cardiovascular disease, hypertension, Syndrome X, depression, anxiety, glaucoma, human immunodeficiency virus (HIV) or acquired immunodeficiency syndrome (AIDS), neurodegeneration (for example, Alzheimer's and Parkinson's), cognition enhancement, Cushing's Syndrome, Addison's Disease, osteoporosis, frailty, inflammatory diseases (such as osteoarthritis, rheumatoid arthritis, asthma and rhinitis), tests of adrenal function, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism and prevention of muscle frailty. Examples or GR antagonists that can be used in combination with a compound of the present invention include compounds of formula Ib below:

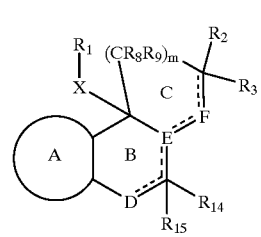

isomers thereof, prodrugs of said compounds and isomers, and pharmaceutically acceptable salts of said compounds, isomers and prodrugs;

wherein m is 1 or 2;

——— represents an optional bond;

A is selected from the group consisting of

A-1
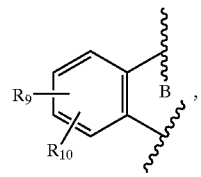

A-2
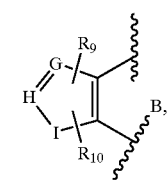

A-3
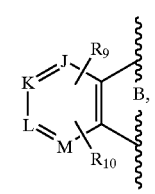

A-4
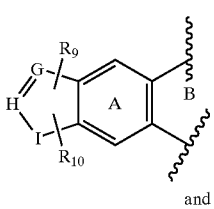

and

A-5
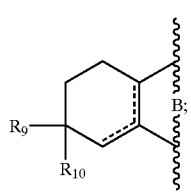

D is $CR_7$, $CR_7R_{16}$, N, $NR_7$ or O;

E is C, $CR_6$ or N;

F is $CR_4$, $CR_4R_5$ or O;

G, H and I together with 2 carbon atoms from the A-ring or 2 carbon atoms from the B-ring form a 5-membered heterocyclic ring comprising one or more N, O or S atoms; provided that there is at most one of O and S per ring;

J, K, L and M together with 2 carbon atoms from the B-ring forms a 6-membered heterocyclic ring comprising 1 or more N atoms;

X is a) absent, b) —$CH_2$—, c) —CH(OH)— or d) —C(O)—;

$R_1$ is a) —H, b) —Z—$CF_3$, c) —($C_1$-$C_6$)alkyl, d) —($C_2$-$C_6$)alkenyl, e) —($C_2$-$C_6$)alkynyl, f) —CHO, g) —CH=N—$OR_{12}$, h) —Z—C(O)$OR_{12}$, i) —Z—C (O)—$NR_{12}R_{13}$, j) —Z—C(O)—$NR_{12}$—Z-het, k) —Z—$NR_{12}R_{13}$, l) —Z—$NR_{12}$het, m) —Z-het, n) —Z—O-het, o) —Z-aryl', p) —Z—O-aryl', q) —CHOH-aryl' or r) —C(O)-aryl' wherein aryl' in substituents o) to r) is substituted independently with 0, 1 or 2 of the following: —Z—OH, —Z—$NR_{12}R_{13}$, —Z—$NR_{12}$-het, —C(O)$NR_{12}R_{13}$, —C(O)O($C_1$-$C_6$) alkyl, —C(O)OH, —C(O)-het, —$NR_{12}$—C(O)—($C_1$-$C_6$)alkyl, —$NR_{12}$—C(O)—($C_2$-$C_6$)alkenyl, —$NR_{12}$—C(O)—($C_2$-$C_6$)alkynyl, —$NR_{12}$—C(O)—Z-het, —CN, —Z-het, —O—($C_1$-$C_3$)alkyl—C(O)—$NR_{12}R_{13}$, —O—($C_1$-$C_3$)alkyl—C(O)O($C_1$-$C_6$)alkyl, —$NR_{12}$—Z—C(O)O($C_1$-$C_6$)alkyl, —N (Z—C(O)O ($C_1$-$C_6$)alkyl)$_2$, —$NR_{12}$—Z—C(O)—$NR_{12}R_{13}$, —Z—$NR_{12}$—$SO_2$—$R_{13}$, —$NR_{12}$—$SO_2$-het, —C(O) H, —Z—$NR_{12}$—Z—O($C_1$-$C_6$)alkyl, —Z—$NR_{12}$—Z—$NR_{12}R_{13}$, —Z—$NR_{12}$—($C_3$-$C_6$)cycloalkyl, —Z—N(Z—O($C_1$-$C_6$)alkyl)$_2$, —$SO_2R_{12}$, —$SOR_{12}$, —$SR_{12}$, —$SO_2NR_{12}R_{13}$, —O—C(O)—($C_1$-$C_4$)alkyl, —O—$SO_2$—($C_1$-$C_4$)alkyl, -halo or —$CF_3$;

Z for each occurrence is independently a) —($C_0$-$C_6$)alkyl, b) —($C_2$-$C_6$)alkenyl or c) —($C_2$-$C_6$)alkynyl;

$R_2$ is a) —H, b) -halo, c) —OH, d) —($C_1$-$C_6$)alkyl substituted with 0 or 1 —OH, e) —$NR_{12}R_{13}$, f) —Z—C(O)O($C_1$-$C_6$)alkyl, g) —Z—C(O)$NR_{12}R_{13}$, h) —O—($C_1$-$C_6$)alkyl, i) —Z—O—C(O)—($C_1$-$C_6$) alkyl, j) —Z—O—($C_1$-$C_3$)alkyl—C(O)—$NR_{12}R_{13}$, k) —Z—O—($C_1$-$C_3$)alkyl—C(O)—O($C_1$-$C_6$)alkyl, l) —O—($C_2$-$C_6$)alkenyl, m) —O—($C_2$-$C_6$)alkynyl, n) —O—Z-het, o) —COOH, p) —C(OH)$R_{12}R_{13}$ or q) —Z—CN;

$R_3$ is a) —H, b) —($C_1$-$C_{10}$)alkyl wherein 1 or 2 carbon atoms, other than the connecting carbon atom, may optionally be replaced with 1 or 2 heteroatoms independently selected from S, O and N and wherein each carbon atom is substituted with 0, 1 or 2 $R_y$, c) —($C_2$-$C_{10}$)alkenyl substituted with 0, 1 or 2 $R_y$, d) —($C_2$-$C_{10}$)alkynyl wherein 1 carbon atom, other than the connecting carbon atom, may optionally be replaced with 1 oxygen atom and wherein each carbon atom is substituted with 0, 1 or 2 $R_y$, e) —CH=C=$CH_2$, f) —CN, g) —($C_3$-$C_6$)cycloalkyl, h) —Z-aryl, i) —Z-het, j) —C(O)O($C_1$-$C_6$)alkyl, k) —O($C_1$-$C_6$)alkyl, l) —Z—S—$R_{12}$, m) —Z—S(O)—$R_{12}$, n) —Z—S(O)$_2$—$R_{12}$, o) —$CF_3$ p) —$NR_{12}$O—($C_1$-$C_6$)alkyl or q) —$CH_2OR_y$;

provided that one of $R_2$ and $R_3$ is absent when there is a double bond between $CR_2R_3$ (the 7 position) and the F moiety (the 8 position) of the C-ring;

$R_y$ for each occurrence is independently a) —OH, b) -halo, c) —Z—$CF_3$, d) —Z—CF($C_1$-$C_3$ alkyl)$_2$, e) —CN, f) —$NR_{12}R_{13}$, g) —($C_3$-$C_6$)cycloalkyl, h) —($C_3$-$C_6$) cycloalkenyl, i) —($C_0$-$C_3$)alkyl-aryl, j) -het or k) —$N_3$;

or $R_2$ and $R_3$ are taken together to form a) =$CHR_{11}$, b) =$NOR_{11}$, c) =O, d) =N—$NR_{12}$, e) =N—$NR_{12}$—C (O)—$R_{12}$, f) oxiranyl or g) 1,3-dioxolan-4-yl;

$R_4$ and $R_5$ for each occurrence are independently a) —H, b) —CN, c) —($C_1$-$C_6$)alkyl substituted with 0 to 3 halo, d) —($C_2$-$C_6$)alkenyl substituted with 0 to 3 halo, e) —($C_2$-$C_6$)alkynyl substituted with 0 to 3 halo, f) —O—($C_1$-$C_6$)alkyl substituted with 0 to 3 halo, g) —O—($C_2$-$C_6$)alkenyl substituted with 0 to 3 halo, h) —O—($C_2$-$C_6$)alkynyl substituted with 0 to 3 halo, i) halo, j) —OH, k) ($C_3$-$C_6$)cycloalkyl or l) ($C_3$-$C_6$) cycloalkenyl;

or $R_4$ and $R_5$ are taken together to form =O;

$R_6$ is a) —H, b) —CN, c) —($C_1$-$C_6$)alkyl substituted with 0 to 3 halo, d) —($C_2$-$C_6$)alkenyl substituted with 0 to 3 halo, e) —($C_2$-$C_6$)alkynyl substituted with 0 to 3 halo or f) —OH;

$R_7$ and $R_{16}$ for each occurrence are independently a) —H, b) -halo, c) —CN, d) —($C_1$-$C_6$)alkyl substituted with 0 to 3 halo, e) —($C_2$-$C_6$)alkenyl substituted with 0 to 3 halo or f) —($C_2$–$C_6$)alkynyl substituted with 0 to 3 halo; provided that $R_7$ is other than —CN or -halo when D is $NR_7$;

or $R_7$ and $R_{16}$ are taken together to form =O;

$R_8$, $R_9$, $R_{14}$ and $R_{15}$ for each occurrence are independently a) —H, b) -halo, c) ($C_1$–$C_6$)alkyl substituted with 0 to 3 halo, d) —($C_2$–$C_6$)alkenyl substituted with 0 to 3 halo, e) —($C_2$–$C_6$)alkynyl substituted with 0 to 3 halo, f) —CN, g) —($C_3$–$C_6$)cycloalkyl, h) —($C_3$–$C_6$)cycloalkenyl, i) —OH, j) —O—($C_1$–$C_6$)alkyl, k) —O—($C_1$–$C_6$)alkenyl, l) —O—($C_1$–$C_6$)alkynyl, m) —$NR_{12}R_{13}$, n) —C(O)$OR_{12}$ or o) —C(O)$NR_{12}R_{13}$;

or $R_8$ and $R_9$ are taken together on the C-ring to form =O; provided that when m is 2, only one set of $R_8$ and $R_9$ are taken together to form =O;

or $R_{14}$ and $R_{15}$ are taken together to form =O; provided that when $R_{14}$ and $R_{15}$ are taken together to form =O, D is other than $CR_7$ and E is other than C;

$R_{10}$ is a) —($C_1$–$C_{10}$)alkyl substituted with 0 to 3 substituents independently selected from -halo, —OH and —$N_3$, b) —($C_2$–$C_{10}$)alkenyl substituted with 0 to 3 substituents independently selected from -halo, —OH and —$N_3$, c) —($C_2$–$C_{10}$)alkynyl substituted with 0 to 3 substituents independently selected from -halo, —OH and —$N_3$, d) -halo, e) —Z—CN, f) —OH, g) —Z-het, h) —Z—$NR_{12}R_{13}$, i) —Z—C(O)-het, j) —Z—C(O)—($C_1$–$C_6$)alkyl, k) —Z—C(O)—$NR_{12}R_{13}$, l) —Z—C(O)—$NR_{12}$—Z—CN, m) —Z—C(O)—$NR_{12}$—Z-het, n) —Z—C(O)—$NR_{12}$—Z-aryl, o) —Z—C(O)—$NR_{12}$—Z—$NR_{12}R_{13}$, p) —Z—C(O)—$NR_{12}$—Z—O ($C_1$–$C_6$)alkyl, q) —($C_1$–$C_6$)alkyl—C(O)OH, r) —Z—C(O)O($C_1$–$C_6$)alkyl, s) —Z—O—($C_0$–$C_6$)alkyl-het, t) —Z—O—($C_0$–$C_6$)alkyl-aryl, u) —Z—O—($C_1$–$C_6$)alkyl substituted with 0 to 2 $R_x$, v) —Z—O—($C_1$–$C_6$)alkyl—CH(O), w) —Z—O—($C_1$–$C_6$)alkyl—$NR_{12}$-het, x) —Z—O—Z-het—Z-het, y) —Z—O—Z-het—Z—$NR_{12}R_{13}$, z) —Z—O—Z-het—C(O)-het, a1) —Z—O—Z—C(O)-het, b1) —Z—O—Z—C(O)-het-het, c1) —Z—O—Z—C(O)—($C_1$–$C_6$)alkyl, d1) —Z—O—Z—C(S)—$NR_{12}R_{13}$, e1) —Z—O—Z—C(O)—$NR_{12}R_{13}$, f1) —Z—O—Z—($C_1$–$C_3$)alkyl—C(O)—$NR_{12}R_{13}$, g1) —Z—O—Z—C(O)—O($C_1$–$C_6$)alkyl, h1) —Z—O—Z—C(O)—OH, i1) —Z—O—Z—C(O)—$NR_{12}$—O($C_1$–$C_6$)alkyl, j1) —Z—O—Z—C(O)—$NR_{12}$—OH, k1) —Z—O—Z—C(O)—$NR_{12}$—Z—$NR_{12}R_{13}$, l1) —Z—O—Z—C(O)—$NR_{12}$—Z-het, m1) —Z—O—Z—C(O)—$NR_{12}$—$SO_2$—($C_1$–$C_6$)alkyl, n1) —Z—O—Z—C(=$NR_{12}$)($NR_{12}R_{13}$), o1) —Z—O—Z—C(=$NOR_{12}$)($NR_{12}R_{13}$), p1) —Z—$NR_{12}$—C(O)—O—Z—$NR_{12}R_{13}$, q1) —Z—S—C(O)—$NR_{12}R_{13}$, r1) —Z—O—$SO_2$—($C_1$–$C_6$)alkyl, s1) —Z—O—$SO_2$-aryl, t1) —Z—O—$SO_2$—$NR_{12}R_{13}$, u1) —Z—O—$SO_2$—$CF_3$, v1) —Z—$NR_{12}$C(O)$OR_{13}$ or w1) —Z—$NR_{12}$C(O)$R_{13}$;

or $R_9$ and $R_{10}$ are taken together on the moiety of formula A-5 to form a)=O or b)=$NOR_{12}$;

$R_{11}$ is a) —H, b) —($C_1$–$C_5$)alkyl, c) —($C_3$–$C_6$)cycloalkyl or d) —($C_0$–$C_3$)alkyl-aryl;

$R_{12}$ and $R_{13}$ for each occurrence are each independently a) —H, b) —($C_1$–$C_6$)alkyl wherein 1 or 2 carbon atoms, other than the connecting carbon atom, may optionally be replaced with 1 or 2 heteroatoms independently selected from S, O and N and wherein each carbon atom is substituted with 0 to 6 halo, c) —($C_2$–$C_6$)alkenyl substituted with 0 to 6 halo or d) —($C_1$–$C_6$)alkynyl wherein 1 carbon atom, other than the connecting carbon atom, may optionally be replaced with 1 oxygen atom and wherein each carbon atom is substituted with 0 to 6 halo;

or $R_{12}$ and $R_{13}$ are taken together with N to form het;

or $R_6$ and $R_{14}$ or $R_{15}$ are taken together to form 1,3-dioxolanyl;

aryl is a) phenyl substituted with 0 to 3 $R_x$, b) naphthyl substituted with 0 to 3 $R_x$ or c) biphenyl substituted with 0 to 3 $R_x$;

het is a 5-, 6- or 7-membered saturated, partially saturated or unsaturated ring containing from one (1) to three (3) heteroatoms independently selected from the group consisting of nitrogen, oxygen and sulfur; and including any bicyclic group in which any of the above heterocyclic rings is fused to a benzene ring or another heterocycle; and the nitrogen may be in the oxidized state giving the N-oxide form; and substituted with 0 to 3 $R_x$;

$R_x$ for each occurrence is independently a) -halo, b) —OH, c) —($C_1$–$C_6$)alkyl, d) —($C_2$–$C_6$)alkenyl, e) —($C_2$–$C_6$)alkynyl, f) —O($C_1$–$C_6$)alkyl, g) —O($C_2$–$C_6$)alkenyl, h) —O($C_2$–$C_6$)alkynyl, i) —($C_0$–$C_6$)alkyl—$NR_{12}R_{13}$, j) —C(O)—$NR_{12}R_{13}$, k) —Z—$SO_2R_{12}$, l) —Z—$SOR_{12}$, m) —Z—$SR_{12}$, n) —$NR_{12}$—$SO_2R_{13}$, o) —$NR_{12}$—C(O)—$R_{13}$, p) —$NR_{12}$—$OR_{13}$, q) —$SO_2$—$NR_{12}R_{13}$, r) —CN, s) —$CF_3$, t) —C(O)($C_1$–$C_6$)alkyl, u) =O, v) —Z—$SO_2$-phenyl or w) —Z—$SO_2$-het';

aryl' is phenyl, naphthyl or biphenyl;

het' is a 5-, 6- or 7-membered saturated, partially saturated or unsaturated ring containing from one (1) to three (3) heteroatoms independently selected from the group consisting of nitrogen, oxygen and sulfur; and including any bicyclic group in which any of the above heterocyclic rings is fused to a benzene ring or another heterocycle;

provided that:
1) X—$R_1$ is other than hydrogen or methyl;
2) when $R_9$ and $R_{10}$ are substituents on the A-ring, they are other than mono- or di-methoxy;
3) when $R_2$ and $R_3$ are taken together to form =$CHR_{11}$ or =O wherein $R_{11}$ is —O($C_1$–$C_6$)alkyl, then —X—$R_1$ is other than ($C_1$–$C_4$)alkyl;
4) when $R_2$ and $R_3$ taken together are C=O and $R_9$ is hydrogen on the A-ring; or when $R_2$ is hydroxy, $R_3$ is hydrogen and $R_9$ is hydrogen on the A-ring, then $R_{10}$ is other than —O—($C_1$–$C_6$)alkyl or —O—$CH_2$-phenyl at the 2-position of the A-ring;
5) when X—$R_1$ is ($C_1$–$C_4$)alkyl, ($C_2$–$C_4$)alkenyl or ($C_2$–$C_4$)alkynyl, $R_9$ and $R_{10}$ are other than mono-hydroxy or =O, including the diol form thereof, when taken together; and
6) when X is absent, $R_1$ is other than a moiety containing a heteroatom independently selected from N, O or S directly attached to the juncture of the B-ring and the C-ring. (See U.S. Provisional Patent Application No. 60/132,130.)

The compounds of the present invention can also be used in combination with a sorbitol dehydrogenase inhibitor. Sorbitol dehydrogenase inhibitors lower fructose levels and have been used to treat or prevent diabetic complications such as neuropathy, retinopathy, nephropathy, cardiomyopathy, microangiopathy, and macroangiopathy. U.S. Pat. Nos. 5,728,704 and 5,866,578 disclose compounds and a method for treating or preventing diabetic complications by inhibiting the enzyme sorbitol dehydrogenase.

A compound of the present invention can also be used in combination with a sodium-hydrogen exchanger type 1 (NHE-1) inhibitor. Examples of NHE-1 inhibitors include a compound having the Formula Ic

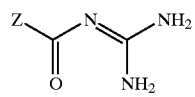

Formula Ic a prodrug thereof or a pharmaceutically acceptable salt of said compound or of said prodrug, wherein Z is carbon connected and is a five-membered, diaza, diunsaturated ring having two contiguous nitrogens, said ring optionally mono-, di-, or tri-substituted with up to three substituents independently selected from $R^1$, $R^2$ and $R^3$;

or

Z is carbon connected and is a five-membered, triaza, diunsaturated ring, said ring optionally mono- or di-substituted with up to two substituents independently selected from $R^4$ and $R^5$;

wherein $R^1$, $R^2$, $R^3$, $R^4$ and $R^5$ are each independently hydrogen, hydroxy($C_1$–$C_4$)alkyl, ($C_1$–$C_4$)alkyl, ($C_1$–$C_4$)alkylthio, ($C_3$–$C_4$)cycloalkyl, ($C_3$–$C_7$)cycloalkyl($C_1$–$C_4$)alkyl, ($C_1$–$C_4$)alkoxy, ($C_1$–$C_4$)alkoxy($C_1$–$C_4$)alkyl, mono-N- or di-N,N-($C_1$–$C_4$)alkylcarbamoyl, M or M($C_1$–$C_4$)alkyl, any of said previous ($C_1$–$C_4$)alkyl moieties optionally having from one to nine fluorines; said ($C_1$–$C_4$)alkyl or ($C_3$–$C_4$)cycloalkyl optionally mono-or di-substituted independently with hydroxy, ($C_1$–$C_4$)alkoxy, ($C_1$–$C_4$)alkylthio, ($C_1$–$C_4$)alkylsulfinyl, ($C_1$–$C_4$)alkylsulfonyl, ($C_1$–$C_4$) alkyl, mono-N- or di-N,N-($C_1$–$C_4$)alkylcarbamoyl or mono-N- or di-N,N-($C_1$–$C_4$)alkylaminosulfonyl; and said ($C_3$–$C_4$)cycloalkyl optionally having from one to seven fluorines;

wherein M is a partially saturated, fully saturated or fully unsaturated five to eight membered ring optionally having one to three heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

said M is optionally substituted, on one ring if the moiety is monocyclic, or one or both rings if the moiety is bicyclic, on carbon or nitrogen with up to three substituents independently selected from $R^6$, $R^7$ and $R^8$, wherein one of $R^6$, $R^7$ and $R^8$ is optionally a partially saturated, fully saturated, or fully unsaturated three to seven membered ring optionally having one to three heteroatoms selected independently from oxygen, sulfur and nitrogen optionally substituted with ($C_1$–$C_4$) alkyl and additionally $R^6$, $R^7$ and $R^8$ are optionally hydroxy, nitro, halo, ($C_1$–$C_4$)alkoxy, ($C_1$–$C_4$) alkoxycarbonyl, ($C_1$-$C_4$)alkyl, formyl, ($C_1$–$C_4$) alkanoyl, ($C_1$–$C_4$)alkanoyloxy, ($C_1$–$C_4$)alkanoylamino, ($C_1$–$C_4$)alkoxycarbonylamino, sulfonamido, ($C_1$–$C_4$) alkylsulfonamido, amino, mono-N- or di-N,N-($C_1$–$C_4$) alkylamino, carbamoyl, mono-N- or di-N,N-($C_1$–$C_4$) alkylcarbamoyl, cyano, thiol, ($C_1$–$C_4$)alkylthio, ($C_1$–$C_4$)alkylsulfinyl, ($C_1$-$C_4$)alkylsulfonyl, mono-N- or di-N,N-($C_1$–$C_4$)alkylaminosulfonyl, ($C_2$–$C_4$) alkenyl, ($C_2$–$C_4$)alkynyl or ($C_5$–$C_7$)cycloalkenyl, wherein said ($C_1$–$C_4$)alkoxy, ($C_1$–$C_4$)alkyl, ($C_1$–$C_7$) alkanoyl, ($C_1$-$C_4$)alkylthio, mono-N- or di-N,N-($C_1$–$C_4$)alkylamino or ($C_3$–$C_7$)cycloalkyl $R^6$, $R^7$ and $R^8$ substituents are optionally mono-substituted independently with hydroxy, ($C_1$–$C_4$)alkoxycarbonyl, ($C_3$–$C_7$)cycloalkyl, ($C_1$–$C_4$)alkanoyl, ($C_1$-$C_4$) alkanoylamino, ($C_1$–$C_4$)alkanoyloxy, ($C_1$–$C_4$) alkoxycarbonylamino, sulfonamido, ($C_1$–$C_4$) alkylsulfonamido, amino, mono-N- or di-N,N-($C_1$-$C_4$) alkylamino, carbamoyl, mono-N- or di-N,N-($C_1$–$C_4$) alkylcarbamoyl, cyano, thiol, nitro, ($C_1$–$C_4$)alkylthio, ($C_1$–$C_4$)alkylsulfinyl, ($C_1$–$C_4$)alkylsulfonyl or mono-N- or di-N,N-($C_1$–$C_4$)alkylaminosulfonyl or optionally substituted with one to nine fluorines. (See PCT publication number WO 99/43663)

A compound of the present invention can also be used in combination with a glycogen phosphorylase inhibitor. Examples of glycogen phosphorylase inhibitors are set forth below.

One group of glycogen phosphorylase inhibitors that can be used includes compounds of Formula AA:

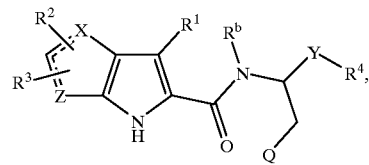

AA a stereoisomer, pharmaceutically acceptable salt or prodrug thereof, or a pharmaceutically acceptable salt of the prodrug, wherein Q is aryl, substituted aryl, heteroaryl, or substituted heteroaryl;

each Z and X are independently (C, CH or $CH_2$), N, O or S;

$X^1$ is $NR^a$, —$CH_2$—, O or S;

each ———— is independently a bond or is absent, provided that both ———— are not simultaneously bonds;

$R^1$ is hydrogen, halogen, —$OC_1$–$C_8$alkyl, —$SC_1$-$C_8$alkyl, —$C_1$–$C_8$alkyl, —$CF_3$, —$NH_2$, —$NHC_1$–$C_8$alkyl, —$N(C_1$–$C_8$alkyl$)_2$, —$NO_2$, —$CN$, —$CO_2H$, —$CO_2C_1$–$C_8$alkyl, —$C_2$–$C_8$alkenyl, or —$C_2$–$C_8$alkynyl;

each $R^a$ and $R^b$ is independently hydrogen or —$C_1$–$C_8$alkyl;

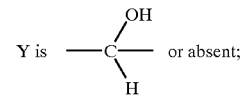

Y is ———— or absent;

$R^2$ and $R^3$ are independently hydrogen, halogen, —$C_1$–$C_8$alkyl, —$CN$, —$C{\equiv}C$—$Si(CH_3)_3$, —$OC_1$–$C_8$alkyl, —$SC_1$–$C_8$alkyl, —$CF_3$, —$NH_2$, —$NHC_1$–$C_8$alkyl, —$N(C_1$–$C_8$alkyl$)_2$, —$NO_2$, —$CO_2H$, —$CO_2C_1$–$C_8$alkyl, —$C_2$–$C_8$alkenyl, or —$C_2$–$C_8$alkynyl, or $R^2$ and $R^3$ together with the atoms on the ring to which they are attached form a five or six membered ring containing from 0 to 3 heteroatoms and from 0 to 2 double bonds;

$R^4$ is —C(=O)—A;

A is —NR$^d$R$^d$, —NR$^a$CH$_2$CH$_2$OR$^a$,

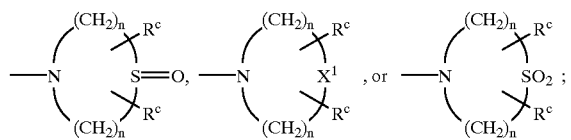

each R$^d$ is independently hydrogen, C$_1$–C$_8$alkyl, C$_1$–C$_8$alkoxy, aryl, substituted aryl, heteroaryl, or substituted heteroaryl;
each R$^c$ is independently hydrogen, —C(=O)OR$^a$, —OR$^a$, —SR$^a$, or —NR$^a$R$^a$; and
each n is independently 1–3.

Preferred examples of glycogen phosphorylase inhibitors of Formula AA include 6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;
2-bromo-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;
2-methyl-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;
(±)-2-methyl-6H-thieno[2,3-b]pyrrole-5-carboxylic acid [1-benzyl-2-((3R,4S)-dihydroxy-pyrrolidin-1-yl)-2-oxo-ethyl]-amide;
2-bromo-6H-thieno[2,3-b]pyrrole-5-carboxylic acid [(1S)-benzyl-2-((3R,4S)-dihydroxy-pyrrolidin-1-yl)-2-oxo-ethyl]-amide;
2-chloro-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;
2-chloro-6H-thieno[2,3-b]pyrrole-5-carboxylic acid [(1S)-benzyl-2-((3R,4S)-dihydroxy-pyrrolidin-1-yl)-2-oxo-ethyl]-amide;
2,4-dichloro-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;
(±)-4H-thieno[3,2-b]pyrrole-5-carboxylic acid [1-benzyl-2-((3R,4S)-dihydroxy-pyrrolidin-1-yl)-2-oxo-ethyl]-amide;
2-bromo-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;
4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;
(±)-2-bromo-4H-furo[3,2-b]pyrrole-5-carboxylic acid [1-benzyl-2-((3R,4S)-dihydroxy-pyrrolidin-1-yl)-2-oxo-ethyl]-amide;
2-bromo-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;
6H-thieno[2,3-b]pyrrole-5-carboxylic acid [(1S)-benzyl-2-((3R,4S)-dihydroxy-pyrrolidin-1-yl)-2-oxo-ethyl]-amide;
2-bromo-4H-thieno[3,2-b]pyrrole-5-carboxylic acid [(1S)-benzyl-2-((3R,4S)-dihydroxy-pyrrolidin-1-yl)-2-oxo-ethyl]-amide;
2-methyl-4H-thieno[3,2-b]pyrrole-5-carboxylic acid [(1S)-benzyl-2-((3R,4S)-dihydroxy-pyrrolidin-1-yl)-2-oxo-ethyl]-amide;
2,4-dichloro-6H-thieno[2,3-b]pyrrole-5-carboxylic acid [(1S)-benzyl-2-((3R,4S)-dihydroxy-pyrrolidin-1-yl)-2-oxo-ethyl]-amide;
2-cyano-6H-thieno[2,3-b]pyrrole-5-carboxylic acid [(1S)-benzyl-2-(3-hydroxy-azetidin-1-yl)-2-oxo-ethyl]-amide;
2-chloro-6H-thieno[2,3-b]pyrrole-5-carboxylic acid [(1S)-benzyl-2-morpholin-4-yl-2-oxo-ethyl]-amide;
2-chloro-6H-thieno[2,3-b]pyrrole-5-carboxylic acid [(1S)-dimethylcarbamoyl-2-phenyl-ethyl]-amide;
2-chloro-6H-thieno[2,3-b]pyrrole-5-carboxylic acid [(1S)-benzyl-2-(1,1-dioxo-1-thiazolidin-3-yl)-2-oxo-ethyl]-amide;
1-{(2S)-[(2-chloro-6H-thieno[2,3-b]pyrrole-5-carbonyl)-amino]-3-phenyl-propionyl}-piperidine-4-carboxylic acid ethyl ester;
2-bromo-6H-thieno[2,3-b]pyrrole-5-carboxylic acid [(1S)-benzyl-2-(3-hydroxy-azetidin-1-yl)-2-oxo-ethyl]-amide;
2-methyl-4H-furo[3,2-b]pyrrole-5-carboxylic acid [(1S)-benzyl-2-((3R,4S)-dihydroxy-pyrrolidin-1-yl)-2-oxo-ethyl]-amide;
2-trimethylsilanylethynyl-6H-thieno[2,3-b]pyrrole-5-carboxylic acid [(1S)-benzyl-2-(3-hydroxy-azetidin-1-yl)-2-oxo-ethyl]-amide;
2-ethynyl-6H-thieno[2,3-b]pyrrole-5-carboxylic acid [(1S)-benzyl-2-(3-hydroxy-azetidin-1-yl)-2-oxo-ethyl]-amide;
2-fluoro-4H-thieno[3,2-b]pyrrole-5-carboxylic acid [(1S)-benzyl-2-((3R,4S)-dihydroxy-pyrrolidin-1-yl)-2-oxo-ethyl]-amide;
2-cyano-4H-furo[3,2-b]pyrrole-5-carboxylic acid [(1S)-benzyl-2-(3-hydroxy-azetidin-1-yl)-2-oxo-ethyl]-amide;
2-chloro-4H-furo[3,2-b]pyrrole-5-carboxylic acid [(1S)-benzyl-2-((3R,4S)-dihydroxy-pyrrolidin-1-yl)-2-oxo-ethyl]-amide;
2-chloro-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;
1-{(2S)-[(2-chloro-6H-thieno[2,3-b]pyrrole-5-carbonyl)-amino]-3-phenyl-propionyl}-piperidine-4-carboxylic acid;
3-chloro-4H-thieno[3,2-b]pyrrole-5-carboxylic acid [(1S)-benzyl-2-((3R,4S)-dihydroxy-pyrrolidin-1-yl)-2-oxo-ethyl]-amide;
3-chloro-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;
3-bromo-4H-thieno[3,2-b]pyrrole-5-carboxylic acid [(1S)-benzyl-2-((3R,4S)-dihydroxy-pyrrolidin-1-yl)-2-oxo-ethyl]-amide;
3-bromo-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;
2-chloro-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;
2-chloro-4H-thieno[3,2-b]pyrrole-5-carboxylic acid [(1S)-benzyl-2-((3R,4S)-dihydroxy-pyrrolidin-1-yl)-2-oxo-ethyl]-amide;
3-methyl-4H-thieno[3,2-b]pyrrole-5-carboxylic acid [(1S)-benzyl-2-((3R,4S)-dihydroxy-pyrrolidin-1-yl)-2-oxo-ethyl]-amide;
3-methyl-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;
2-cyano-4H-thieno[3,2-b]pyrrole-5-carboxylic acid [(1S)-benzyl-2-((3R,4S)-dihydroxy-pyrrolidin-1-yl)-2-oxo-ethyl]-amide;
2-cyano-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;
3-bromo-4H-furo[3,2-b]pyrrole-5-carboxylic acid [(1S)-benzyl-2-((3R,4S)-dihydroxy-pyrrolidin-1-yl)-2-oxo-ethyl]-amide;

3-bromo-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

4H-1,7-dithia-4-aza-cyclopenta[a]pentalene-5-carboxylic acid [(1S)-benzyl-3-((3R,4S)-dihydroxy-pyrrolidin-1-yl)-(2R)-hydroxy-3-oxo-propyl]-amide;

4H-1,7-dithia-4-aza-cyclopenta[a]pentalene-5-carboxylic acid [(1S)-benzyl-2-((3R,4S)-dihydroxy-pyrrolidin-1-yl)-2-oxo-ethyl]-amide;

2-chloro-3-methyl-4H-thieno[3,2-b]pyrrole-5-carboxylic acid [(1S)-benzyl-2-((3R,4S)-dihydroxy-pyrrolidin-1-yl)-2-oxo-ethyl]-amide;

2-chloro-3-methyl-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

2-methylsulfanyl-4H-thieno[3,2-b]pyrrole-5-carboxylic acid [(1S)-benzyl-2-((3R,4S)-dihydroxy-pyrrolidin-1-yl)-2-oxo-ethyl]-amide;

2-Bromo-4H-thieno[3,2-b]pyrrole-5-carboxylic acid [(1S)-benzyl-2-(3-hydroxy-azetidin-1-yl)-2-oxo-ethyl]-amide;

2-Bromo-4H-thieno[3,2-b]pyrrole-5-carboxylic acid [(1S)-benzyl-2-(1,1-dioxo-1-thiazolidin-3-yl)-2-oxo-ethyl]-amide;

2-Bromo-4H-thieno[3,2-b]pyrrole-5-carboxylic acid [(1S)-benzyl-2-morpholin4-yl-2-oxo-ethyl]-amide;

2-bromo4H-thieno[3,2-b]pyrrole-5-carboxylic acid [(1S)-benzyl-2-((3S,4S)-dihydroxy-pyrrolidin-1-yl)-2-oxo-ethyl]-amide;

2-bromo-4H-thieno[3,2-b]pyrrole-5-carboxylic acid [(1S)-benzyl-2-((3R,4R)-dihydroxy-pyrrolidin-1-yl)-2-oxo-ethyl]-amide; and 2-bromo-4H-thieno[3,2-b]pyrrole-5-carboxylic acid [(1S)-benzyl-2-(4-hydroxy-piperidin-1-yl)-2-oxo-ethyl]-amide, and the stereoisomers, pharmaceutically acceptable salts and prodrugs of the compounds, and the pharmaceutically acceptable salts of the prodrugs.

Methods for making the above recited glycogen phosphorylase inhibitors of Formula AA can be found in U.S. provisional patent application No. 60/157,148, filed Sep. 30, 1999.

Commonly assigned PCT published applications WO 96/39384 and WO 96/39385 disclose glycogen phosphorylase inhibitors of Formulas IQ and IAQ.

One group of glycogen phosphorylase inhibitors that can be used in the present invention includes compounds of Formula IQ

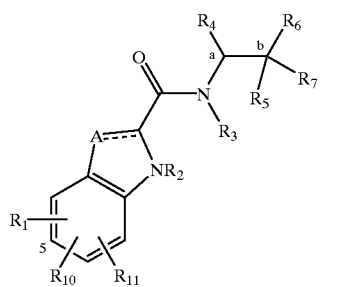

Formula IQ and the pharmaceutically acceptable salts and prodrugs thereof
wherein
the dotted line (———) is an optional bond;
A is —C(H)=, —C((C$_1$–C$_4$)alkyl)= or —C(halo)= when the dotted line (———) is a bond, or A is methylene or —CH((C$_1$–C$_4$)alkyl)— when the dotted line (———) is not a bond;

$R_1$, $R_{10}$ or $R_{11}$ are each independently H, halo, 4-, 6- or 7-nitro, cyano, (C$_1$–C$_4$)alkyl, (C$_1$–C$_4$)alkoxy, fluoromethyl, difluoromethyl or trifluoromethyl;

$R_2$ is H;

$R_3$ is H or (C$_1$–C$_5$)alkyl;

$R_4$ is H, methyl, ethyl, n-propyl, hydroxy(C$_1$–C$_3$)alkyl, (C$_1$–C$_3$)alkoxy(C$_1$–C$_3$)alkyl, phenyl(C$_1$–C$_4$)alkyl, phenylhydroxy(C$_1$–C$_4$)alkyl, phenyl(C$_1$–C$_4$)alkoxy (C$_1$–C$_4$)alkyl, thien-2- or -3-yl(C$_1$–C$_4$)alkyl or fur-2- or -3-yl(C$_1$–C$_4$)alkyl wherein said $R_4$ rings are mono-, di- or tri-substituted independently on carbon with H, halo, (C$_1$–C$_4$)alkyl, (C$_1$–C$_4$)alkoxy, trifluoromethyl, hydroxy, amino or cyano; or $R_4$ is pyrid-2-, -3- or -4-yl(C$_1$–C$_4$)alkyl, thiazol-2-, -4- or -5-yl(C$_1$–C$_4$)alkyl, imidazol-1-, -2-, -4- or -5-yl (C$_1$–C$_4$)alkyl, pyrrol-2- or -3-yl(C$_1$–C$_4$)alkyl, oxazol-2-, -4- or -5-yl-(C$_1$–C$_4$)alkyl, pyrazol-3-, -4- or -5-yl (C$_1$–C$_4$)alkyl, isoxazol-3-, -4- or -5-yl(C$_1$–C$_4$)alkyl, isothiazol-3-, -4- or -5-yl(C$_1$–C$_4$)alkyl, pyridazin-3- or -4-yl-(C$_1$–C$_4$)alkyl, pyrimidin-2-, -4-, -5- or -6-yl (C$_1$–C$_4$)alkyl, pyrazin-2- or -3-yl(C$_1$–C$_4$)alkyl or 1,3,5-triazin-2-yl(C$_1$–C$_4$)alkyl, wherein said preceding $R_4$ heterocycles are optionally mono- or di-substituted independently with halo, trifluoromethyl, (C$_1$–C$_4$) alkyl, (C$_1$–C$_4$)alkoxy, amino or hydroxy and said mono-or di-substituents are bonded to carbon;

$R_5$ is H, hydroxy, fluoro, (C$_1$–C$_5$)alkyl, (C$_1$–C$_5$)alkoxy, (C$_1$–C$_6$)alkanoyl, amino(C$_1$–C$_4$)alkoxy, mono-N- or di-N,N-(C$_1$–C$_4$)alkylamino(C$_1$–C$_4$)alkoxy, carboxy (C$_1$–C$_4$)alkoxy, (C$_1$–C$_5$)alkoxy-carbonyl(C$_1$–C$_4$) alkoxy, benzyloxycarbonyl(C$_1$–C$_4$)alkoxy, or carbonyloxy wherein said carbonyloxy is carbon-carbon linked with phenyl, thiazolyl, imidazolyl, 1H-indolyl, furyl, pyrrolyl, oxazolyl, pyrazolyl, isoxazolyl, isothiazolyl, pyridazinyl, pyrimidinyl, pyrazinyl or 1,3,5-triazinyl and wherein said preceding $R_5$ rings are optionally mono-substituted with halo, (C$_1$–C$_4$)alkyl, (C$_1$–C$_4$) alkoxy, hydroxy, amino or trifluoromethyl and said mono-substituents are bonded to carbon;

$R_7$ is H, fluoro or (C$_1$–C$_5$)alkyl; or $R_5$ and $R_7$ can be taken together to be oxo;

$R_6$ is carboxy, (C$_1$–C$_8$)alkoxycarbonyl, C(O)NR$_8$R$_9$ or C(O)R$_{12}$, wherein $R_8$ is H, (C$_1$–C$_3$)alkyl, hydroxy or (C$_1$–C$_3$)alkoxy; and $R_9$ is H, (C$_1$–C$_8$)alkyl, hydroxy, (C$_1$–C$_8$)alkoxy, methylene-perfluorinated(C$_1$-C$_8$)alkyl, phenyl, pyridyl, thienyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, piperidinyl, morpholinyl, pyridazinyl, pyrimidinyl, pyrazinyl, piperazinyl or 1,3,5-triazinyl wherein said preceding $R_9$ rings are carbon-nitrogen linked; or $R_9$ is mono-, di- or tri-substituted (C$_1$–C$_5$)alkyl, wherein said substituents are independently H, hydroxy, amino, mono-N- or di-N,N-(C$_1$–C$_5$)alkylamino; or $R_9$ is mono- or di-substituted (C$_1$–C$_5$)alkyl, wherein said substituents are independently phenyl, pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, pyridinyl, piperidinyl, morpholinyl, pyridazinyl, pyrimidinyl, pyrazinyl, piperazinyl or 1,3,5-triazinyl wherein the nonaromatic nitrogen-containing $R_9$ rings are optionally mono-substituted on nitrogen with (C$_1$–C$_6$)

alkyl, benzyl, benzoyl or $(C_1-C_6)$alkoxycarbonyl and wherein the $R_9$ rings are optionally mono-substituted on carbon with halo, $(C_1-C_4)$alkyl, $(C_1-C_4)$alkoxy, hydroxy, amino, or mono-N- and di-N,N $(C_1-C_5)$ alkylamino provided that no quaternized nitrogen is included and there are no nitrogen-oxygen, nitrogen-nitrogen or nitrogen-halo bonds;

$R_{12}$ is piperazin-1-yl, 4-$(C_1-C_4)$alkylpiperazin-1-yl, 4-formylpiperazin-1-yl, morpholino, thiomorpholino, 1-oxothiomorpholino, 1,1-dioxo-thiomorpholino, thiazolidin-3-yl, 1-oxo-thiazolidin-3-yl, 1,1-dioxo-thiazolidin-3-yl, 2-$(C_1-C_6)$alkoxycarbonylpyrrolidin-1-yl, oxazolidin-3-yl or 2(R)-hydroxymethylpyrrolidin-1-yl; or $R_{12}$ is 3- and/or 4-mono-or di-substituted oxazetidin-2-yl, 2-, 4-, and/or 5-mono- or di-substituted oxazolidin-3-yl, 2-, 4-, and/or 5- mono- or di-substituted thiazolidin-3-yl, 2-, 4-, and/or 5- mono- or di-substituted 1-oxothiazolidin-3-yl, 2-, 4-, and/or 5- mono- or di-substituted 1,1-dioxothiazolidin-3-yl, 3- and/or 4-, mono- or di-substituted pyrrolidin-1-yl, 3-, 4- and/or 5-, mono-, di- or tri-substituted piperidin-1-yl, 3-, 4-, and/or 5- mono-, di-, or tri-substituted piperazin-1-yl, 3-substituted azetidin-1-yl, 4- and/or 5-, mono- or di-substituted 1,2-oxazinan-2-yl, 3-and/or 4-mono- or di-substituted pyrazolidin-1-yl, 4- and/or 5-, mono- or di-substituted isoxazolidin-2-yl, 4-and/or 5-, mono- and/or di-substituted isothiazolidin-2-yl wherein said $R_{12}$ substituents are independently H, halo, $(C_1-C_5)$-alkyl, hydroxy, amino, mono-N- or di-N,N-$(C_1-C_5)$ alkylamino, formyl, oxo, hydroxyimino, $(C_1-C_5)$ alkoxy, carboxy, carbamoyl, mono-N- or di-N,N-$(C_1-C_4)$alkylcarbamoyl, $(C_1-C_4)$alkoxyimino, $(C_1-C_4)$alkoxymethoxy, $(C_1-C_6)$alkoxycarbonyl, carboxy$(C_1-C_5)$alkyl or hydroxy$(C_1-C_5)$alkyl;

with the proviso that if $R_4$ is H, methyl, ethyl or n-propyl $R_5$ is OH;

with the proviso that if $R_5$ and $R_7$ are H, then $R_4$ is not H, methyl, ethyl, n-propyl, hydroxy$(C_1-C_3)$alkyl or $(C_1-C_3)$alkoxy$(C_1-C_3)$alkyl and $R_6$ is $C(O)NR_8R_9$, $C(O)R_{12}$ or $(C_1-C_4)$alkoxycarbonyl.

A first group of preferred compounds of Formula IQ consists of those compounds wherein $R_1$ is 5-H, 5-halo, 5-methyl or 5-cyano;

$R_{10}$ and $R_{11}$ are each independently H or halo;

A is —C(H)═;

$R_2$ and $R_3$ are H;

$R_4$ is phenyl$(C_1-C_2)$alkyl wherein said phenyl groups are mono-, di- or tri-substituted independently with H or halo or mono- or di-substituted independently with H, halo, $(C_1-C_4)$alkyl, $(C_1-C_4)$alkoxy, trifluoromethyl, hydroxy, amino or cyano; or $R_4$ is thien-2- or -3-yl$(C_1-C_2)$alkyl, pyrid-2-, -3- or -4-yl $(C_1-C_2)$alkyl, thiazol-2-, -4- or -5-yl$(C_1-C_2)$alkyl, imidazol-1-, -2-, -4- or -5-yl$(C_1-C_2)$alkyl, fur-2- or -3-yl$(C_1-C_2)$alkyl, pyrrol-2- or -3-yl$(C_1-C_2)$alkyl, oxazol-2-, -4- or -5-yl-$(C_1-C_2)$alkyl, pyrazol-3-, -4- or -5-yl$(C_1-C_2)$alkyl, isoxazol-3-, -4- or -5-yl$(C_1-C_2)$ alkyl wherein said preceding $R_4$ heterocycles are optionally mono- or di-substituted independently with halo, trifluoromethyl, $(C_1-C_4)$alkyl, $(C_1-C_4)$alkoxy, amino or hydroxy and said mono- or di-substituents are bonded to carbon;

$R_5$ is hydroxy;

$R_6$ is $C(O)NR_8R_9$ or $C(O)R_{12}$; and $R_7$ is H.

Within the above first group of preferred compounds of Formula IQ is a first group of especially preferred compounds wherein the carbon atom a has (S) stereochemistry;

the carbon atom b has (R) stereochemistry;

$R_4$ is phenyl$(C_1-C_2)$alkyl, thien-2-yl-$(C_1-C_2)$alkyl, thien-3-yl-$(C_1-C_2)$alkyl, fur-2-yl-$(C_1-C_2)$alkyl or fur-3-yl-$(C_1-C_2)$alkyl wherein said rings are mono- or di-substituted independently with H or fluoro;

$R_6$ is $C(O)NR_8R_9$;

$R_8$ is $(C_1-C_3)$alkyl, hydroxy or $(C_1-C_3)$alkoxy; and $R_9$ is H, $(C_1-C_8)$alkyl, hydroxy, hydroxy$(C_1-C_6)$alkyl, $(C_1-C_8)$alkoxy, pyridyl, morpholinyl, piperazinyl, pyrrolidinyl, piperidinyl, imidazolyl or thiazolyl or $(C_1-C_4)$alkyl mono-substituted with pyridyl, morpholinyl, piperazinyl, pyrrolidinyl, piperidinyl, imidazolyl or thiazolyl.

Within the above first group of especially preferred compounds are the particularly preferred compounds 5-chloro-1H-indole-2-carboxylic acid [(1S)-((R)-hydroxy-dimethylcarbamoyl-methyl)-2-phenyl-ethyl]-amide, 5,6-dichloro-1H-indole-2-carboxylic acid {(1S)-[(R)-hydroxy-(methoxy-methyl-carbamoyl)-methyl]-2-phenyl-ethyl}-amide, 5-chloro-1H-indole-2-carboxylic acid {(1S)-[(R)-hydroxy-(methoxy-methyl-carbamoyl)-methyl]-2-phenyl-ethyl}-amide, 5-chloro-1H-indole-2-carboxylic acid ((1S)-{(R)-hydroxy-[(2-hydroxy-ethyl)-methyl-carbamoyl]-methyl}-2-phenyl-ethyl)-amide, 5-chloro-1H-indole-2-carboxylic acid [(1S)-benzyl-3-((3R,4S)-dihydroxy-pyrrolidin-1-yl)-(2R)-hydroxy-3-oxo-propyl]-amide, 5-chloro-1H-indole-2-carboxylic acid {(1S)-[(R)-hydroxy-(methyl-pyridin-2-yl-carbamoyl)-methyl]-2-phenyl-ethyl}-amide, and 5-chloro-1H-indole-2-carboxylic acid ((1S)-{(R)-hydroxy-[methyl-(2-pyridin-2-yl-ethyl)-carbamoyl]-methyl}-2-phenyl-ethyl)-amide.

Within the above first group of especially preferred compounds are the compounds wherein a. $R_1$ is 5-chloro;

$R_{10}$ and $R_{11}$ are H;

$R_4$ is benzyl;

$R_8$ is methyl; and $R_9$ is methyl;

b. $R_1$ is 5-chloro;

$R_{11}$ is H;

$R_{10}$ is 6-chloro;

$R_4$ is benzyl;

$R_8$ is methyl; and $R_9$ is methoxy;

c. $R_1$ is 5-chloro;

$R_{10}$ and $R_{11}$ are H;

$R_4$ is benzyl;

$R_8$ is methyl; and $R_9$ is methoxy;

d. $R_1$ is 5-chloro;

$R_{10}$ and $R_{11}$ are H;

$R_4$ is benzyl;

$R_8$ is methyl; and $R_9$ is 2-(hydroxy)ethyl;

e. $R_1$ is 5-chloro;
   $R_{10}$ and $R_{11}$ are H;
   $R_4$ is benzyl;
   $R_8$ is methyl; and
   $R_9$ is pyridin-2-yl; and
f. $R_1$ is 5-chloro;
   $R_{10}$ and $R_{11}$ are H;
   $R_4$ is benzyl;
   $R_8$ is methyl; and
   $R_9$ is 2-(pyridin-2-yl)ethyl.

Within the above first group of preferred compounds of Formula IQ is a second group of especially preferred compounds wherein the carbon atom a is (S) stereochemistry;
the carbon atom b is (R) stereochemistry;
$R_4$ is phenyl($C_1$–$C_2$)alkyl, thien-2-yl-($C_1$–$C_2$)alkyl, thien-3-yl-($C_1$–$C_2$)alkyl, fur-2-yl-($C_1$–$C_2$)alkyl or fur-3-yl-($C_1$–$C_2$)alkyl wherein said rings are mono- or di-substituted independently with H or fluoro;
$R_6$ is C(O)$R_{12}$; and
$R_{12}$ is morpholino, 4-($C_1$–$C_4$)alkylpiperazin-1-yl, 3-substituted azetidin-1-yl, 3-and/or 4-, mono- or di-substituted pyrrolidin-1-yl, 4- and/or 5-mono- or di-substituted isoxazolidin-2-yl, 4- and/or 5-, mono- or di-substituted 1,2-oxazinan-2-yl wherein said substituents are each independently H, halo, hydroxy, amino, mono-N- or di-N,N-($C_1$–$C_6$)alkylamino, oxo, hydroxyimino or alkoxy.

Within the above second group of especially preferred compounds are the particularly preferred compounds
5-chloro-1H-indole-2-carboxylic acid [(1S)-benzyl-(2R)-hydroxy-3-(4-methyl-piperazin-1-yl)-3-oxo-propyl]-amide hydrochloride,
5-chloro-1H-indole-2-carboxylic acid [(1S)-benzyl-(2R)-hydroxy-3-(3-hydroxy-azetidin-1-yl)-3-oxo-propyl]-amide,
5-chloro-1H-indole-2-carboxylic acid ((1S)-benzyl-(2R)-hydroxy-3-isoxazolidin-2-yl-3-oxo-propyl)-amide,
5-chloro-1H-indole-2-carboxylic acid ((1S)-benzyl-(2R)-hydroxy-3-[1,2]oxazinan-2-yl-3-oxo-propyl)-amide,
5-chloro-1H-indole-2-carboxylic acid [(1S)-benzyl-(2R)-hydroxy-3-((3S)-hydroxy-pyrrolidin-1-yl)-3-oxo-propyl]-amide,
5-chloro-1H-indole-2-carboxylic acid [(1S)-benzyl-3-((3S,4S)-dihydroxy-pyrrolidin-1-yl)-(2R)-hydroxy-3-oxo-propyl]-amide,
5-chloro-1H-indole-2-carboxylic acid [(1S)-benzyl-3-(cis-3,4-dihydroxy-pyrrolidin-1-yl)-(2R)-hydroxy-3-oxo-propyl]-amide, and
5-chloro-1H-indole-2-carboxylic acid ((1S)-benzyl-(2R)-hydroxy-3-morpholin-4-yl-3-oxo-propyl)-amide.

Within the above second group of especially preferred compounds are the compounds wherein a. $R_1$ is 5-chloro;
   $R_{10}$ and $R_{11}$ are H;
   $R_4$ is benzyl; and
   $R_{12}$ is 4-methylpiperazin-1-yl;
b. $R_1$ is 5-chloro;
   $R_{10}$ and $R_{11}$ are H;
   $R_4$ is benzyl; and
   $R_{12}$ is 3-hydroxyazetidin-1-yl;
c. $R_1$ is 5-chloro;
   $R_{10}$ and $R_{11}$ are H;
   $R_4$ is benzyl; and
   $R_{12}$ is isoxazolidin-2-yl;
d. $R_1$ is 5-chloro;
   $R_{10}$ and $R_{11}$ are H;
   $R_4$ is benzyl; and
   $R_{12}$ is (1,2)-oxazinan-2-yl;
e. $R_1$ is 5-chloro;
   $R_{10}$ and $R_{11}$ are H;
   $R_4$ is benzyl; and
   $R_{12}$ is 3(S)-hydroxypyrrolidin-1-yl;
f. $R_1$ is 5-chloro;
   $R_{10}$ and $R_{11}$ are H;
   $R_4$ is benzyl; and
   $R_{12}$ is (3S,4S)-dihydroxypyrrolidin-1-yl;
g. $R_1$ is 5-chloro;
   $R_{10}$ and $R_{11}$ are H;
   $R_4$ is benzyl; and
   $R_{12}$ is cis-3,4-dihydroxypyrrolidin-1-yl; and
h. $R_1$ is 5-chloro;
   $R_{10}$ and $R_{11}$ are H;
   $R_4$ is benzyl; and
   $R_{12}$ is morpholino.

A second group of preferred compounds of Formula IQ consists of those compounds wherein $R_1$ is H, halo, methyl or cyano;
$R_{10}$ and $R_{11}$ are each independently H or halo;
A is —C(H)=;
$R_2$ and $R_3$ are H;
$R_4$ is phenyl($C_1$–$C_2$)alkyl wherein said phenyl groups are mono-, di- or tri-substituted independently with H or halo or mono- or di-substituted independently with H, halo, ($C_1$–$C_4$)alkyl, ($C_1$–$C_4$)alkoxy, trifluoromethyl, hydroxy, amino or cyano; or
$R_4$ is thien-2- or -3-yl($C_1$–$C_2$)alkyl, pyrid-2-, -3- or -4-yl ($C_1$–$C_2$)alkyl, thiazol-2-, -4- or -5-yl($C_1$–$C_2$)alkyl, imidazol-1-, -2-, -4- or -5-yl($C_1$–$C_2$)alkyl, fur-2- or -3-yl($C_1$–$C_2$)alkyl, pyrrol-2- or -3-yl($C_1$–$C_2$)alkyl, oxazol-2-, -4- or -5-yl-($C_1$–$C_2$)alkyl, pyrazol-3-, -4- or -5-yl($C_1$–$C_2$)alkyl, isoxazol-3-, -4- or -5-yl($C_1$–$C_2$) alkyl wherein said preceding $R_4$ heterocycles are optionally mono- or di-substituted independently with halo, trifluoromethyl, ($C_1$–$C_4$)alkyl, ($C_1$–$C_4$)alkoxy, amino or hydroxy and said mono- or di-substituents are bonded to carbon;
$R_5$ is hydroxy;
$R_6$ is carboxy or ($C_1$–$C_8$)alkoxycarbonyl; and
$R_7$ is H, fluoro or ($C_1$–$C_6$)alkyl.

Within the second group of preferred compounds of Formula IQ is a group of especially preferred compounds wherein the carbon atom a is (S) stereochemistry;
the carbon atom b is (R) stereochemistry;
$R_4$ is phenyl($C_1$–$C_2$)alkyl, thien-2-yl-($C_1$–$C_2$)alkyl, thien-3-yl-($C_1$–$C_2$)alkyl, fur-2-yl-($C_1$–$C_2$)alkyl or fur-3-yl-($C_1$–$C_2$)alkyl wherein said rings are mono- or di-substituted independently with H or fluoro;
$R_{10}$ and $R_{11}$ are H;
$R_6$ is carboxy; and
$R_7$ is H.

Preferred within the immediately preceding group is a compound wherein
$R_1$ is 5-chloro;
$R_{10}$ and $R_{11}$ are H; and
$R_4$ is benzyl.

A third group of preferred compounds of Formula IQ consists of those compounds wherein
$R_1$ is H, halo, methyl or cyano;
$R_{10}$ and $R_{11}$ are each independently H or halo;
A is —C(H)=;
$R_2$ and $R_3$ are H;
$R_4$ is phenyl($C_1$–$C_2$)alkyl wherein said phenyl groups are mono-, di- or tri-substituted independently with H or halo or mono- or di-substituted independently with H, halo, ($C_1$–$C_4$)alkyl, ($C_1$–$C_4$)alkoxy, trifluoromethyl, hydroxy, amino or cyano; or
$R_4$ is thien-2- or -3-yl($C_1$–$C_2$)alkyl, pyrid-2-, -3- or -4-yl ($C_1$–$C_2$)alkyl, thiazol-2-, -4- or -5-yl($C_1$–$C_2$)alkyl, imidazol-1-, -2-, -4- or -5-yl($C_1$–$C_2$)alkyl, fur-2- or -3-yl($C_1$–$C_2$)alkyl, pyrrol-2- or -3-yl($C_1$–$C_2$)alkyl, oxazol-2-, -4- or -5-yl-($C_1$–$C_2$)alkyl, pyrazol-3-, -4- or -5-yl($C_1$–$C_2$)alkyl, isoxazol-3-, -4- or -5-yl($C_1$–$C_2$)alkyl wherein said preceding $R_4$ heterocycles are optionally mono- or di-substituted independently with halo, trifluoromethyl, ($C_1$–$C_4$)alkyl, ($C_1$–$C_4$)alkoxy, amino or hydroxy and said mono- or di-substituents are bonded to carbon;
$R_5$ is fluoro, ($C_1$–$C_4$)alkyl, ($C_1$–$C_5$)alkoxy, amino($C_1$–$C_4$) alkoxy, mono-N- or di-N,N-($C_1$-$C_4$)alkylamino ($C_1$–$C_4$)alkoxy, carboxy($C_1$–$C_4$)alkoxy, ($C_1$–$C_5$) alkoxycarbonyl($C_1$-$C_4$)alkoxy, benzyloxycarbonyl ($C_1$–$C_4$)alkoxy;
$R_6$ is carboxy or ($C_1$–$C_8$)alkoxycarbonyl; and
$R_7$ is H, fluoro or ($C_1$–$C_6$)alkyl.

A fourth group of preferred compounds of Formula IQ consists of those compounds wherein
$R_1$ is H, halo, methyl or cyano;
$R_{10}$ and $R_{11}$ are each independently H or halo;
A is —C(H)=;
$R_2$ and $R_3$ are H;
$R_4$ is phenyl($C_1$–$C_2$)alkyl wherein said phenyl groups are mono-, di- or tri-substituted independently with H or halo or mono- or di-substituted independently with H, halo, ($C_1$–$C_4$)alkyl, ($C_1$–$C_4$)alkoxy, trifluoromethyl, hydroxy, amino or cyano; or
$R_4$ is thien-2- or -3-yl($C_1$–$C_2$)alkyl, pyrid-2-, -3- or -4-yl ($C_1$–$C_2$)alkyl, thiazol-2-, -4- or -5-yl($C_1$–$C_2$)alkyl, imidazol-1-, -2-, -4- or -5-yl($C_1$–$C_2$)alkyl, fur-2- or -3-yl($C_1$–$C_2$)alkyl, pyrrol-2- or -3-yl($C_1$–$C_2$)alkyl, oxazol-2-, -4- or -5-yl-($C_1$–$C_2$)alkyl, pyrazol-3-, -4- or -5-yl($C_1$–$C_2$)alkyl, isoxazol-3-, -4- or -5-yl($C_1$–$C_2$) alkyl wherein said preceding $R_4$ heterocycles are optionally mono- or di-substituted independently with halo, trifluoromethyl, ($C_1$–$C_4$)alkyl, ($C_1$–$C_4$)alkoxy, amino or hydroxy and said mono- or di-substituents are bonded to carbon;
$R_5$ is fluoro, ($C_1$–$C_4$)alkyl, ($C_1$–$C_5$)alkoxy, amino($C_1$–$C_4$) alkoxy, mono-N- or di-N,N-($C_1$-$C_4$)alkylamino ($C_1$–$C_4$)alkoxy, carboxy($C_1$–$C_4$)alkoxy, ($C_1$–$C_5$) alkoxycarbonyl($C_1$-$C_4$)alkoxy, benzyloxycarbonyl ($C_1$–$C_4$)alkoxy;
$R_6$ is C(O)$NR_8R_9$ or C(O)$R_{12}$; and
$R_7$ is H, fluoro or ($C_1$–$C_6$)alkyl.

Another group of glycogen phosphorylase inhibitors includes compounds of the Formula IAQ

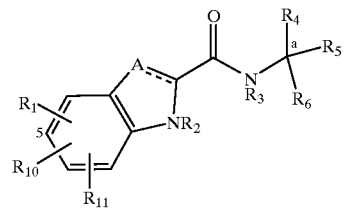

Formula IAQ and the pharmaceutically acceptable salts and prodrugs thereof
wherein
the dotted line (———) is an optional bond;
A is —C(H)=, —C(($C_1$–$C_4$)alkyl)=, —C(halo)= or —N=, when the dotted line (———) is a bond, or A is methylene or —CH(($C_1$–$C_4$)alkyl)—, when the dotted line (———) is not a bond;
$R_1$, $R_{10}$ or $R_{11}$ are each independently H, halo, cyano, 4-, 6-, or 7-nitro, ($C_1$-$C_4$)alkyl, ($C_1$-$C_4$)alkoxy, fluoromethyl, difluoromethyl or trifluoromethyl;
$R_2$ is H;
$R_3$ is H or ($C_1$-$C_5$)alkyl;
$R_4$ is H, methyl, ethyl, n-propyl, hydroxy($C_1$–$C_3$)alkyl, ($C_1$–$C_3$)alkoxy($C_1$–$C_3$)alkyl, phenyl($C_1$–$C_4$)alkyl, phenylhydroxy($C_1$–$C_4$)alkyl, (phenyl)(($C_1$–$C_4$)-alkoxy)($C_1$–$C_4$)alkyl, thien-2- or -3-yl($C_1$–$C_4$)alkyl or fur-2- or -3-yl($C_1$–$C_4$)alkyl wherein said $R_4$ rings are mono-, di- or tri-substituted independently on carbon with H, halo, ($C_1$–$C_4$)alkyl, ($C_1$-$C_4$)alkoxy, trifluoromethyl, hydroxy, amino, cyano or 4,5-dihydro-1H-imidazol-2-yl; or
$R_4$ is pyrid-2-, -3- or -4-yl($C_1$–$C_4$)alkyl, thiazol-2-, -4- or -5-yl($C_1$–$C_4$)alkyl, imidazol-2-, -4- or -5-yl($C_1$–$C_4$) alkyl, pyrrol-2- or -3-yl($C_1$–$C_4$)alkyl, oxazol-2-, -4- or -5-yl($C_1$–$C_4$)alkyl, pyrazol-3-, -4- or -5-yl($C_1$–$C_4$) alkyl, isoxazol-3-, -4- or -5-yl($C_1$–$C_4$)alkyl, isothiazol-3-, -4- or -5-yl($C_1$–$C_4$)alkyl, pyridazin-3- or -4-yl ($C_1$–$C_4$)alkyl, pyrimidin-2-, -4-, -5- or -6-yl($C_1$–$C_4$) alkyl, pyrazin-2- or -3-yl($C_1$–$C_4$)alkyl, 1,3,5-triazin-2-yl($C_1$–$C_4$)alkyl or indol-2-($C_1$–$C_4$)alkyl, wherein said preceding $R_4$ heterocycles are optionally mono- or di-substituted independently with halo, trifluoromethyl, ($C_1$–$C_4$)alkyl, ($C_1$–$C_4$)alkoxy, amino, hydroxy or cyano and said substituents are bonded to carbon; or
$R_4$ is $R_{15}$-carbonyloxymethyl, wherein said $R_{15}$ is phenyl, thiazolyl, imidazolyl, 1H-indolyl, furyl, pyrrolyl, oxazolyl, pyrazolyl, isoxazolyl, isothiazolyl, pyridyl, pyridazinyl, pyrimidinyl, pyrazinyl or 1,3,5-triazinyl and wherein said preceding $R_{15}$ rings are optionally mono- or di-substituted independently with halo, amino, hydroxy, ($C_1$–$C_4$)alkyl, ($C_1$–$C_4$)alkoxy or trifluoromethyl and said mono- or di-substituents are bonded to carbon;
$R_5$ is H;
$R_6$ is carboxy, ($C_1$-$C_8$)alkoxycarbonyl, benzyloxycarbonyl, C(O)$NR_8R_9$ or C(O)$R_{12}$
wherein
$R_8$ is H, ($C_1$–$C_6$)alkyl, cyclo($C_3$–$C_6$)alkyl, cyclo($C_3$–$C_6$) alkyl($C_1$–$C_5$)alkyl, hydroxy or ($C_1$–$C_8$)alkoxy; and
$R_9$ is H, cyclo($C_3$–$C_8$)alkyl, cyclo($C_3$–$C_8$)alkyl($C_1$–$C_5$) alkyl, cyclo($C_4$–$C_7$)alkenyl, cyclo($C_3$–$C_7$)alkyl ($C_1$–$C_5$)alkoxy, cyclo($C_3$–$C_7$)alkyloxy, hydroxy, methylene-perfluorinated($C_1$–$C_8$)alkyl, phenyl, or a heterocycle wherein said heterocycle is pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, pyridinyl, piperidinyl, morpholinyl, pyridazinyl, pyrimidinyl, pyrazinyl, piperazinyl, 1,3,5-triazinyl, benzothiazolyl, benzoxazolyl, benzimidazolyl, thiochromanyl or tetrahydrobenzothiazolyl wherein said heterocycle rings are carbon-nitrogen linked; or $R_9$ is ($C_1$–$C_6$)alkyl or ($C_1$–$C_8$)alkoxy wherein said ($C_1$–$C_6$)alkyl or ($C_1$–$C_8$)alkoxy is optionally monosubstituted with cyclo($C_4$–$C_7$)alken-1-yl, phenyl, thienyl, pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, piperidinyl, morpholinyl, thiomorpholinyl, 1-oxothiomorpholinyl, 1,1-dioxothiomorpholinyl, pyridazinyl, pyrimidinyl, pyrazinyl, piperazinyl, 1,3,5-triazinyl or indolyl and wherein said ($C_1$–$C_6$)alkyl or ($C_1$–$C_8$)alkoxy are optionally additionally independently mono- or di-substituted with halo, hydroxy, ($C_1$–$C_5$)alkoxy, amino, mono-N- or di-N,N-($C_1$–$C_5$)alkylamino, cyano, carboxy, or ($C_1$–$C_4$)alkoxycarbonyl; and wherein the $R_9$ rings are optionally mono- or di-substituted independently on carbon with halo, ($C_1$–$C_4$)alkyl, ($C_1$–$C_4$)alkoxy, hydroxy, hydroxy($C_1$–$C_4$)alkyl, amino($C_1$–$C_4$)alkyl, mono-N- or di-N,N-($C_1$–$C_4$)alkylamino($C_1$–$C_4$)alkyl, ($C_1$–$C_4$)alkoxy($C_1$–$C_4$)alkyl, amino, mono-N- or di-N,N-($C_1$–$C_4$)alkylamino, cyano, carboxy, ($C_1$–$C_5$)alkoxycarbonyl, carbamoyl, formyl or trifluoromethyl and said $R_9$ rings may optionally be additionally mono- or di-substituted independently with ($C_1$–$C_5$)alkyl or halo;

with the proviso that no quaternized nitrogen on any $R_9$ heterocycle is included;

$R_{12}$ is morpholino, thiomorpholino, 1-oxothiomorpholino, 1,1-dioxothiomorpholino, thiazolidin-3-yl, 1-oxothiazolidin-3-yl, 1,1-dioxothiazolidin-3-yl, pyrrolidin-1-yl, piperidin-1-yl, piperazin-1-yl, piperazin-4-yl, azetidin-1-yl, 1,2-oxazinan-2-yl, pyrazolidin-1-yl, isoxazolidin-2-yl, isothiazolidin-2-yl, 1,2-oxazetidin-2-yl, oxazolidin-3-yl, 3,4-dihydroisoquinolin-2-yl, 1,3-dihydroisoindol-2-yl, 3,4-dihydro-2H-quinol-1-yl, 2,3-dihydro-benzo[1,4]oxazin-4-yl, 2,3-dihydro-benzo[1,4]-thiazine-4-yl, 3,4-dihydro-2H-quinoxalin-1-yl, 3,4-dihydro-benzo[c][1,2]oxazin-1-yl, 1,4-dihydro-benzo[d][1,2]oxazin-3-yl, 3,4-dihydro-benzo[e][1,2]-oxazin-2-yl, 3H-benzo[d]isoxazol-2-yl, 3H-benzo[c]isoxazol-1-yl or azepan-1-yl, wherein said $R_{12}$ rings are optionally mono-, di- or tri-substituted independently with halo, ($C_1$–$C_5$)alkyl, ($C_1$–$C_5$)alkoxy, hydroxy, amino, mono-N- or di-N,N-($C_1$-$C_5$)alkylamino, formyl, carboxy, carbamoyl, mono-N- or di-N,N-($C_1$–$C_5$)alkylcarbamoyl, ($C_1$–$C_6$)alkoxy($C_1$–$C_3$)alkoxy, ($C_1$–$C_5$)alkoxycarbonyl, benzyloxycarbonyl, ($C_1$–$C_5$)alkoxycarbonyl($C_1$–$C_5$)alkyl, ($C_1$–$C_4$)alkoxycarbonylamino, carboxy($C_1$–$C_5$)alkyl, carbamoyl($C_1$–$C_5$)alkyl, mono-N- or di-N,N-($C_1$–$C_5$)alkylcarbamoyl($C_1$–$C_5$)alkyl, hydroxy($C_1$–$C_5$)alkyl, ($C_1$–$C_4$)alkoxy($C_1$–$C_4$)alkyl, amino($C_1$–$C_4$)alkyl, mono-N- or di-N,N-($C_1$-$C_4$)alkylamino($C_1$–$C_4$)alkyl, oxo, hydroxyimino or ($C_1$–$C_6$)alkoxyimino and wherein no more than two substituents are selected from oxo, hydroxyimino or ($C_1$–$C_6$)alkoxyimino and oxo, hydroxyimino or ($C_1$–$C_6$)alkoxyimino are on non-aromatic carbon; and wherein said $R_{12}$ rings are optionally additionally mono- or di-substituted independently with ($C_1$–$C_5$)alkyl or halo;

with the proviso that when $R_6$ is ($C_1$–$C_5$)alkoxycarbonyl or benzyloxycarbonyl then $R_1$ is 5-halo, 5-($C_1$–$C_4$)alkyl or 5-cyano and $R_4$ is (phenyl)(hydroxy)($C_1$–$C_4$)alkyl, (phenyl)(($C_1$–$C_4$)alkoxy)($C_1$–$C_4$)alkyl, hydroxymethyl or Ar($C_1$–$C_2$)alkyl, wherein Ar is thien-2- or -3-yl, fur-2- or -3-yl or phenyl wherein said Ar is optionally mono- or di-substituted independently with halo; with the proviso that when $R_1$ and $R_{10}$ and $R_{11}$ are H, $R_4$ is not imidazol-4-ylmethyl, 2-phenylethyl or 2-hydroxy-2-phenylethyl;

with the proviso that when $R_8$ is H and $R_9$ is ($C_1$–$C_6$)alkyl, $R_9$ is not substituted with carboxy or ($C_1$–$C_4$)alkoxycarbonyl on the carbon which is attached to the nitrogen atom N of $NHR_9$;

with the proviso that when $R_6$ is carboxy and $R_1$, $R_{10}$, $R_{11}$ and $R_5$ are all H, then $R_4$ is not benzyl, H, (phenyl)(hydroxy)methyl, methyl, ethyl or n-propyl; and with the proviso that when $R_8$ and $R_9$ are both n-pentyl, $R^1$ is 5-chloro, 5-bromo, 5-cyano, 5-($C_1$–$C_5$ alkyl), 5-($C_1$–$C_5$alkoxy), or 5-trifluoromethyl.

A first group of preferred compounds of Formula IAQ consists of those compounds wherein $R_1$ is 5-H, 5-halo, 5-methyl, 5-cyano or 5-trifluoromethyl;

$R_{10}$ and $R_{11}$ are each independently H or halo;

A is —C(H)=;

$R_2$ and $R_3$ are H;

$R_4$ is H, methyl, phenyl($C_1$–$C_2$)alkyl, wherein said phenyl groups are mono- or di-substituted independently with H, halo, ($C_1$–$C_4$)alkyl, ($C_1$–$C_4$)alkoxy, trifluoromethyl, hydroxy, amino or cyano and wherein said $R_4$ groups are optionally additionally mono-substituted with halo; or $R_4$ is thien-2- or -3-yl($C_1$–$C_2$)alkyl, pyrid-2-, -3- or -4-yl ($C_1$–$C_2$)alkyl, thiazol-2-, -4- or -5-yl($C_1$–$C_2$)alkyl, imidazol-2-, -4- or -5-yl($C_1$–$C_2$)alkyl, fur-2- or -3-yl ($C_1$–$C_2$)alkyl, pyrrol-2- or -3-yl($C_1$–$C_2$)alkyl, oxazol-2-, -4- or -5-yl($C_1$–$C_2$)alkyl, pyrazol-3-, 4- or -5-yl ($C_1$–$C_2$)alkyl, isoxazol-3-, -4- or -5-yl($C_1$–$C_2$)alkyl, isothiazol-3-, -4- or -5-yl($C_1$–$C_2$)alkyl, pyridazin-3- or -4-yl($C_1$–$C_2$)alkyl, pyrimidin-2-, -4-, -5- or -6-yl ($C_1$–$C_2$)alkyl, pyrazin-2- or -3-yl($C_1$–$C_2$)alkyl or 1,3,5-triazin-2-yl($C_1$–$C_2$)alkyl wherein said preceding $R_4$ heterocycles are optionally mono- or di-substituted independently with halo, trifluoromethyl, ($C_1$–$C_4$)alkyl, ($C_1$–$C_4$)alkoxy, amino or hydroxy and said mono- or di-substituents are bonded to carbon;

$R_5$ is H; and $R_6$ is $C(O)NR_8R_9$ or $C(O)R_{12}$.

Within the above first group of preferred compounds of Formula IAQ is a first group of especially preferred compounds wherein $R_4$ is H, phenyl($C_1$–$C_2$)alkyl, thien-2- or -3-yl($C_1$–$C_2$) alkyl, fur-2- or -3-yl($C_1$–$C_2$)alkyl wherein said $R_4$ rings are mono- or di-substituted independently with H or fluoro;

$R_6$ is $C(O)R_{12}$; and $R_{12}$ is morpholino, thiomorpholino, 1-oxothiomorpholino, 1,1-dioxothiomorpholino, thiazolidin-3-yl, 1-oxothiazolidin-3-yl, 1,1-dioxothiazolidin-3-yl, pyrrolidin-1-yl, piperidin-1-yl, piperazin-1-yl, piperazin-4-yl, azetidin-1-yl, 1,2-oxazinan-2-yl, isoxazolidin-2-yl, isothiazolidin-2-yl, 1,2-oxazetidin-2-yl, oxazolidin-3-yl, 1,3-dihydroisoindol-2-yl, or azepan-1-yl, wherein said $R_{12}$ rings are optionally mono- or di-substituted independently with halo, $(C_1-C_5)$alkyl, $(C_1-C_5)$alkoxy, hydroxy, amino, mono-N-or di-N,N-$(C_1-C_5)$alkylamino, formyl, carboxy, carbamoyl, mono-N- or di-N,N-$(C_1-C_5)$alkylcarbamoyl, $(C_1-C_5)$alkoxycarbonyl, hydroxy$(C_1-C_5)$alkyl, amino$(C_1-C_4)$alkyl, mono-N- or di-N,N-$(C_1-C_4)$alkylamino$(C_1-C_4)$alkyl, oxo, hydroxyimino or $(C_1-C_6)$alkoxyimino with the proviso that only the $R_{12}$ heterocycles thiazolidin-3-yl, pyrrolidin-1-yl, piperidin-1-yl, piperazin-1-yl, piperazin-4-yl, azetidin-1-yl, 1,2-oxazinan-2-yl, isoxazolidin-2-yl, or oxazolidin-3-yl are optionally mono- or di-substituted with oxo, hydroxyimino, or $(C_1-C_6)$alkoxyimino; and wherein said $R_{12}$ rings are optionally additionally mono- or di-substituted independently with $(C_1-C_5)$alkyl.

Within the above group of especially preferred compounds are the compounds 5-chloro-1H-indole-2-carboxylic acid [(1S)-benzyl-2-(3-hydroxyimino-pyrrolidin-1-yl)-2-oxo-ethyl]-amide, 5-chloro-1H-indole-2-carboxylic acid [2-(cis-3,4-dihydroxy-pyrrolidin-1-yl)-2-oxo-ethyl]-amide, 5-chloro-1H-indole-2-carboxylic acid [2-((3S,4S)-dihydroxy-pyrrolidin-1-yl)-2-oxo-ethyl]-amide, 5-chloro-1H-indole-2-carboxylic acid [(1S)-benzyl-2-(cis-3,4-dihydroxy-pyrrolidin-1-yl)-2-oxo-ethyl]-amide, 5-chloro-1H-indole-2-carboxylic acid [2-(1,1-dioxo-thiazolidin-3-yl)-2-oxo-ethyl]-amide, 5-chloro-1H-indole-2-carboxylic acid (2-oxo-2-thiazolidin-3-yl-ethyl)-amide, 5-chloro-1H-indole-2-carboxylic acid [(1S)-(4-fluoro-benzyl)-2-(4-hydroxy-piperidin-1-yl)-2-oxo-ethyl]-amide, 5-chloro-1H-indole-2-carboxylic acid [(1S)-benzyl-2-((3RS)-hydroxy-piperidin-1-yl)-2-oxo-ethyl]-amide, 5-chloro-1H-indole-2-carboxylic acid [2-oxo-2-((1RS)-oxo-1-thiazolidin-3-yl)-ethyl]-amide, 5-chloro-1H-indole-2-carboxylic acid [(1S)-(2-fluoro-benzyl)-2-(4-hydroxy-piperidin-1-yl)-2-oxo-ethyl]-amide, 5-chloro-1H-indole-2-carboxylic acid [(1S)-benzyl-2-((3S,4S)-dihydroxy-pyrrolidin-1-yl)-2-oxo-ethyl]-amide, 5-chloro-1H-indole-2-carboxylic acid [(1S)-benzyl-2-(3-hydroxy-azetidin-1-yl)-2-oxo-ethyl]-amide, 5-chloro-1H-indole-2-carboxylic acid [(1S)-benzyl-2-(3-hydroxyimino-azetidin-1-yl)-2-oxo-ethyl]-amide, 5-chloro-1H-indole-2-carboxylic acid [(1S)-benzyl-2-(4-hydroxyimino-piperidin-1-yl)-2-oxo-ethyl]-amide, and 5-chloro-1H-indole-2-carboxylic acid [1-benzyl-2-(3-hydroxypyrrolidin-1-yl)-2-oxo-ethyl]amide.

Within the above group of especially preferred compounds is a first group of particularly preferred compounds wherein $R_4$ is H; and $R_{12}$ is thiazolidin-3-yl, 1-oxo-thiazolidin-3-yl, 1,1-dioxo-thiazolidin-3-yl or oxazolidin-3-yl or said $R_{12}$ substituents optionally mono- or di-substituted independently with carboxy, $(C_1-C_5)$alkoxycarbonyl, hydroxy $(C_1-C_3)$alkyl, amino$(C_1-C_3)$alkyl, mono-N- or di-N,N-$(C_1-C_3)$alkylamino$(C_1-C_3)$alkyl or $R_{12}$ is mono- or di-substituted pyrrolidin-1-yl wherein said substituents are independently carboxy, $(C_1-C_5)$ alkoxycarbonyl, $(C_1-C_5)$alkoxy, hydroxy, hydroxy$(C_1-C_3)$alkyl, amino, amino$(C_1-C_3)$alkyl, mono-N- or di-N, N-$(C_1-C_3)$alkylamino$(C_1-C_3)$alkyl or mono-N- or di-N,N-$(C_1-C_4)$alkylamino; and the $R_{12}$ rings are optionally additionally independently disubstituted with $(C_1-C_5)$alkyl.

Preferred compounds within the immediately preceding group of particularly preferred compounds are compounds wherein a. $R_1$ is 5-chloro;

$R_{10}$ and $R_{11}$ are H; and $R_{12}$ is cis-3,4-dihydroxy-pyrrolidin-1-yl;

b. $R_1$ is 5-chloro;

$R_{10}$ and $R_{11}$ are H; and $R_{12}$ is (3S,4S)-dihydroxy-pyrrolidin-1-yl;

c. $R_1$ is 5-chloro;

$R_{10}$ and $R_{11}$ are H; and $R_{12}$ is 1,1-dioxo-thiazolidin-3-yl;

d. $R_1$ is 5-chloro;

$R_{10}$ and $R_{11}$ are H; and $R_{12}$ is thiazolidin-3-yl; and e. $R_1$ is 5-chloro;

$R_{10}$ and $R_{11}$ are H; and $R_{12}$ is 1-oxo-thiazolidin-3-yl.

Within the above group of especially preferred compounds is a second group of particularly preferred compounds wherein $R_4$ is phenylmethyl, thien-2- or -3-ylmethyl wherein said $R_4$ rings are optionally mono- or di-substituted with fluoro; and $R_{12}$ is thiazolidin-3-yl, 1-oxo-thiazolidin-3-yl, 1,1-dioxo-thiazolidin-3-yl or oxazolidin-3-yl or said $R_{12}$ substituents optionally mono- or di-substituted independently with carboxy or $(C_1-C_5)$alkoxycarbonyl, hydroxy $(C_1-C_3)$alkyl, amino$(C_1-C_3)$alkyl or mono-N- or di-N, N-$(C_1-C_3)$alkylamino$(C_1-C_3)$alkyl or $R_{12}$ is mono- or di-substituted azetidin-1-yl or mono- or di-substituted pyrrolidin-1-yl or mono- or di-substituted piperidin-1-yl wherein said substituents are independently carboxy, $(C_1-C_5)$alkoxycarbonyl, hydroxy$(C_1-C_3)$alkyl, amino$(C_1-C_3)$alkyl,, mono-N- or di-N,N-$(C_1-C_3)$alkylamino$(C_1-C_3)$alkyl, hydroxy, $(C_1-C_5)$alkoxy, amino, mono-N- or di-N,N-$(C_1-C_5)$ alkylamino, oxo, hydroxyimino or $(C_1-C_5)$ alkoxyimino; and the $R_{12}$ rings are optionally additionally mono- or di-substituted independently with $(C_1-C_5)$alkyl.

Preferred compounds within the immediately preceding group of particularly preferred compounds are compounds wherein a. $R_1$ is 5-chloro;

$R_{10}$ and $R_{11}$ are H;

$R_4$ is 4-fluorobenzyl;

$R_{12}$ is 4-hydroxypiperidin-1-yl; and the stereochemistry of carbon (a) is (S);

b. $R_1$ is 5-chloro;

$R_{10}$ and $R_{11}$ are H;

$R_4$ is benzyl;

$R_{12}$ is 3-hydroxypiperidin-1-yl; and the stereochemistry of carbon (a) is (S);

c. $R_1$ is 5-chloro; $R_{10}$ and $R_{11}$ are H;
   $R_4$ is benzyl;
   $R_{12}$ is cis-3,4-dihydroxy-pyrrolidin-1-yl; and
   the stereochemistry of carbon (a) is S;
d. $R_1$ is 5-chloro;
   $R_{10}$ and $R_1$, are H; $R_4$ is benzyl;
   $R_{12}$ is 3-hydroxyimino-pyrrolidin-1-yl; and
   the stereochemistry of carbon (a) is (S);
e. $R_1$ is 5-chloro;
   $R_{10}$ and $R_{11}$ are H;
   $R_4$ is 2-fluorobenzyl;
   $R_{12}$ is 4-hydroxypiperidin-1-yl; and
   the stereochemistry of carbon (a) is (S);
f. $R_1$ is 5-chloro;
   $R_{10}$ and $R_1$ are H;
   $R_4$ is benzyl;
   $R_{12}$ is (3S,4S)-dihydroxy-pyrrolidin-1-yl; and
   the stereochemistry of carbon (a) is (S);
g. $R_1$ is 5-chloro;
   $R_{10}$ and $R_{11}$ are H;
   $R_4$ is benzyl;
   $R_{12}$ is 3-hydroxy-azetidin-1-yl; and
   the stereochemistry of carbon (a) is (S);
h. $R_1$ is 5-chloro;
   $R_{10}$ and $R_1$ are H;
   $R_4$ is benzyl;
   $R_{12}$ is 3-hydroxyimino-azetidin-1-yl; and
   the stereochemistry of carbon (a) is (S); and
i. $R_1$ is 5-chloro;
   $R_{10}$ and $R_{11}$ are H;
   $R_4$ is benzyl;
   $R_{12}$ is 4-hydroxyimino-piperidin-1-yl; and
   the stereochemistry of carbon (a) is (S).

A second group of especially preferred compounds within the first group of preferred compounds are the compounds wherein $R_4$ is H, phenyl($C_1$–$C_2$)alkyl, thien-2- or -3-yl($C_1$–$C_2$) alkyl, fur-2- or -3-yl($C_1$-$C_2$)alkyl wherein said $R_4$ rings are mono- or di-substituted independently with H or fluoro;

$R_6$ is C(O)NR$_8$R$_9$; and $R_8$ is H, ($C_1$–$C_5$)alkyl, hydroxy or ($C_1$–$C_4$)alkoxy; and $R_9$ is H, cyclo($C_4$–$C_6$)alkyl, cyclo($C_3$–$C_6$)alkyl($C_1$–$C_5$) alkyl, methylene-perfluorinated($C_1$-$C_3$)alkyl, pyridyl, pyrrolidinyl, oxazolyl, thiazolyl, imidazolyl, piperidinyl, benzothiazolyl or thiochromanyl; or $R_9$ is ($C_1$–$C_5$)alkyl wherein said ($C_1$–$C_5$)alkyl is optionally substituted with cyclo($C_4$–$C_6$)alkenyl, phenyl, thienyl, pyridyl, pyrrolidinyl, oxazolyl, thiazolyl, imidazolyl, pyrazolyl, piperidinyl, morpholinyl, thiomorpholinyl, 1-oxothiomorpholinyl, or 1,1-dioxothiomorpholinyl and wherein said ($C_1$–$C_5$)alkyl or ($C_1$–$C_4$)alkoxy is optionally additionally independently mono- or di-substituted with halo, hydroxy, ($C_1$–$C_5$)alkoxy, amino, mono-N- or di-N,N-($C_1$–$C_5$) alkylamino, cyano, carboxy, or ($C_1$-$C_4$) alkoxycarbonyl; and wherein the $R_9$ rings are optionally mono- or di-substituted independently on carbon with halo, ($C_1$–$C_4$)alkyl, ($C_1$–$C_4$)alkoxy, hydroxy, amino, mono-N- or di-N,N-($C_1$-$C_4$)alkylamino, carbamoyl, ($C_1$–$C_5$) alkoxycarbonyl or carbamoyl.

Within the immediately preceding second group of especially preferred compounds are the compounds wherein
a. $R_1$ is 5-chloro;
   $R_{10}$ and $R_{11}$ are H;
   $R_4$ is benzyl;
   $R_8$ is methyl; and
   $R_9$ is 3-(dimethylamino)propyl;
b. the stereochemistry of carbon (a) is (S);
   $R_1$ is 5-chloro;
   $R_{10}$ and $R_{11}$ are H;
   $R_4$ is benzyl;
   $R_8$ is methyl; and
   $R_9$ is 3-pyridyl;
c. the stereochemistry of carbon (a) is (S);
   $R_1$ is 5-chloro;
   $R_{10}$ and $R_{11}$ are H;
   $R_4$ is benzyl;
   $R_8$ is methyl; and
   $R_9$ is 2-hydroxyethyl; and
d. the stereochemistry of carbon (a) is (S);
   $R_1$ is 5-fluoro;
   $R_{10}$ and $R_{11}$ are H;
   $R_4$ is 4-fluorophenylmethyl;
   $R_8$ is methyl; and
   $R_9$ is 2-morpholinoethyl.

A third group of especially preferred compounds within the first group of preferred compounds are the compounds wherein $R_4$ is H, phenyl($C_1$–$C_2$)alkyl, thien-2- or -3-yl($C_1$–$C_2$) alkyl, fur-2- or -3-yl($C_1$-$C_2$)alkyl wherein said $R_4$ rings are mono- or di-substituted independently with H or fluoro;

$R_6$ is C(O)NR$_8$R$_9$; and $R_8$ is H, ($C_1$–$C_5$)alkyl, hydroxy or ($C_1$–$C_4$)alkoxy; and $R_9$ is ($C_1$–$C_4$)alkoxy wherein said ($C_1$–$C_4$)alkoxy is optionally substituted with cyclo($C_4$–$C_6$)alkenyl, phenyl, thienyl, pyridyl, pyrrolidinyl, oxazolyl, thiazolyl, imidazolyl, pyrazolyl, piperidinyl, morpholinyl, thiomorpholinyl, 1-oxothiomorpholinyl, or 1,1-dioxothiomorpholinyl and wherein said ($C_1$–$C_5$) alkyl or ($C_1$–$C_4$)alkoxy is optionally additionally independently mono- or di-substituted with halo, hydroxy, ($C_1$–$C_5$)alkoxy, amino, mono-N- or di-N,N-($C_1$–$C_5$) alkylamino, cyano, carboxy, or ($C_1$-$C_4$) alkoxycarbonyl; and wherein the $R_9$ rings are optionally mono- or di-substituted independently on carbon with halo, ($C_1$–$C_4$)alkyl, ($C_1$–$C_4$)alkoxy, hydroxy, amino, mono-N- or di-N,N-($C_1$-$C_4$)alkylamino, carbamoyl, ($C_1$–$C_5$) alkoxycarbonyl or carbamoyl.

Within the immediately preceding third group of especially preferred compounds are the compounds wherein
a. $R_1$ is 5-chloro;
   $R_{10}$ and $R_{11}$ are H;
   $R_4$ is benzyl;
   $R_8$ is methyl; and
   $R_9$ is 2-hydroxyethoxy;
b. the stereochemistry of carbon (a) is (S);
   $R_1$ is 5-chloro;

$R_{10}$ and $R_{11}$ are H;
$R_4$ is 4-fluorophenylmethyl;
$R_8$ is methyl; and
$R_9$ is methoxy;
c. the stereochemistry of carbon (a) is (S);
$R_1$ is 5-chloro;
$R_{10}$ and $R_{11}$ are H;
$R_4$ is benzyl;
$R_8$ is methyl; and
$R_9$ is methoxy;

A second group of preferred compounds of Formula IAQ are those compounds wherein
$R_1$ is 5-halo, 5-methyl, 5-cyano or trifluoromethyl;
$R_{10}$ and $R_{11}$ are each independently H or halo;
A is —C(H)=;
$R_2$ and $R_3$ are H;
$R_4$ is H, phenyl($C_1$–$C_2$)alkyl, thien-2- or -3-yl($C_1$–$C_2$) alkyl, fur-2- or -3-yl($C_1$–$C_2$)alkyl wherein said rings are mono- or di-substituted independently with H or fluoro;
$R_5$ is H; and
$R_6$ is ($C_1$–$C_5$)alkoxycarbonyl.

A third group of preferred compounds of Formula IAQ are those compounds wherein
$R_1$ is 5-halo, 5-methyl, 5-cyano or trifluoromethyl;
$R_{10}$ and $R_{11}$ are each independently H or halo;
A is —C(H)=;
$R_2$ and $R_3$ are H;
$R_4$ is H, methyl or phenyl($C_1$–$C_2$)alkyl, wherein said phenyl groups are mono- or di-substituted independently with H, halo, ($C_1$–$C_4$)alkyl, ($C_1$–$C_4$)alkoxy, trifluoromethyl, hydroxy, amino or cyano and wherein said phenyl groups are additionally mono- or di-substituted independently H or halo; or
$R_4$ is thien-2- or -3-yl($C_1$–$C_2$)alkyl, pyrid-2-, -3- or -4-yl ($C_1$–$C_2$)alkyl, thiazol-2-, -4- or -5-yl($C_1$–$C_2$)alkyl, imidazol-2-, -4- or -5-yl($C_1$–$C_2$)alkyl, fur-2- or -3-yl ($C_1$–$C_2$)alkyl, pyrrol-2- or -3-yl($C_1$–$C_2$)alkyl, oxazol-2-, 4- or -5-yl($C_1$–$C_2$)alkyl, pyrazol-3-, -4- or -5-yl ($C_1$–$C_2$)alkyl, isoxazol-3-, -4- or -5-yl($C_1$–$C_2$)alkyl, isothiazol-3-, -4- or -5-yl($C_1$–$C_2$)alkyl, pyridazin-3- or 4-yl($C_1$–$C_2$)alkyl, pyrimidin-2-, -4-, -5- or -6-yl ($C_1$–$C_2$)alkyl, pyrazin-2- or -3-yl($C_1$–$C_2$)alkyl or 1,3, 5-triazin-2-yl($C_1$–$C_2$)alkyl wherein said preceding $R_4$ heterocycles are optionally mono- or di-substituted independently with halo, trifluoromethyl, ($C_1$–$C_4$) alkyl, ($C_1$–$C_4$)alkoxy, amino or hydroxy and said mono- or di-substituents are bonded to carbon;
$R_5$ is H; and
$R_6$ is carboxy.

Within the third group of preferred compounds is a first group of especially preferred compounds wherein
$R_{10}$ and $R_{11}$ are H; and
$R_4$ is H.

Particularly preferred within the immediately preceding especially preferred group is a compound wherein
$R_1$ is 5-chloro.

Another group of preferred glycogen phosphorylase inhibitors includes:
5-chloro-1H-indole-2-carboxylic acid [(1S)-((R)-hydroxy-dimethylcarbamoyl-methyl)-2-phenyl-ethyl]-amide;
5-chloro-1H-indole-2-carboxylic acid [(1S)-((R)-hydroxy-(methoxy-methyl-carbamoyl)-methyl)-2-phenyl-ethyl]-amide;
5-chloro-1H-indole-2-carboxylic acid [(1S)-benzyl-3-((3-hydroxy azetidin-1-yl)-(2R)-hydroxy-3-oxopropyl]-amide;
5-chloro-1H-indole-2-carboxylic acid [(1S)-((R)-hydroxy-[methyl-(2-hydroxyethyl)-carbamoyl]-methyl)-2-phenyl-ethyl]-amide;
5-chloro-1H-indole-2-carboxylic acid [(1S)-benzyl-(2R)-hydroxy-3-((3S)-hydroxy-pyrrolidin-1-yl)-3-oxopropyl]-amide;
5-chloro-1H-indole-2-carboxylic acid [(1S)-benzyl-(2R)-hydroxy -3-((3S,4S)-dihydroxy-pyrrolidin-1-yl)-3-oxopropyl]-amide;
5-chloro-1H-indole-2-carboxylic acid [(1S)-benzyl-3-(cis-3, 4-dihydroxy-pyrrolidin-1-yl)-(2R)-hydroxy-3-oxopropyl]-amide;
5-chloro-1H-indole-2-carboxylic acid [1-benzyl-2-(3-hydroxypyrrolidin-1-yl)-2-oxo-ethyl]-amide;
5-chloro-1H-indole-2-carboxylic acid [(1S)-benzyl-2-(cis-3, 4-dihydroxypyrrolidin-1-yl)-2-oxo-ethyl]-amide;
5-chloro-1H-indole-2-carboxylic acid [(1S)-(4-fluorobenzyl-2-(4-hydroxy-piperidin-1-yl)-2-oxo-ethyl]-amide;
5-chloro-1H-indole-2-carboxylic acid (2-oxo-2-thiazolidin-3-yl-ethyl)-amide;
5-chloro-1H-indole-2-carboxylic acid [(1S)-benzyl-2-(3-hydroxy-azetidin-1-yl)-2-oxo-ethyl]-amide;
5-chloro-1H-indole-2-carboxylic acid [(1S)-benzyl-2-(3-hydroxyimino-azetidin-1-yl)-2-oxo-ethyl]-amide; and
5-chloro-1H-indole-2-carboxylic acid [(1S)-benzyl-2-((3S, 4S)-dihydroxy-pyrrolidin-1-yl)-2-oxo-ethyl]-amide, and the pharmaceutically acceptable salts, and prodrugs and salts of the prodrugs.

Any glycogen phosphorylase inhibitor may be used in combination with a compound of the present invention. Glycogen phosphorylase inhibition is readily determined by those skilled in the art according to standard assays (for example, Pesce, et al. (1977) *Clinical Chemistry* 23:1711–1717). A variety of glycogen phosphorylase inhibitors are described above, however, other glycogen phosphorylase inhibitors will be known to those skilled in the art (e.g., WO 95/24391-A and those disclosed in U.S. Pat. No. 5,952,363). The following documents also disclose glycogen phosphorylase inhibitors that can be used in the present invention: U.S. Pat. No. 5,998,463; Oikanomakos et al., *Protein Science,* 1999 8(10) 1930–1945, which in particular discloses the compound 3-isopropyl-4-(2-chlorophenyl)-1, 4-dihydro-1-ethyl-2-methylpyridine; WO 9524391; WO 9709040; WO 9840353; WO 9850359; WO 9731901; EP 884050; and Hoover et al., *J. Med. Chem.,* 1998, 41, 2934–2938.

Moreover, the compounds of the present invention can be administered in combination with other pharmaceutical agents such as a cholesterol biosynthesis inhibitor or a cholesterol absorption inhibitor, especially a HMG-CoA reductase inhibitor, or a HMG-CoA synthase inhibitor, or a HMG-CoA reductase or synthase gene expression inhibitor, a CETP inhibitor, a bile acid sequesterant, a fibrate, an ACAT inhibitors, a squalene synthetase inhibitor, an antioxidant or niacin. The compounds of the present invention may also be administered in combination with a naturally occurring compound that act to lower plasma cholesterol levels. Such naturally occurring compounds are commonly called nutraceuticals and include, for example, garlic extract and niacin.

In addition, the compounds of the present invention can be used in combination with an apolipoprotein B secretion inhibitor and/or microsomal triglyceride transfer protein (MTP) inhibitor. Some preferred apolipoprotein B secretion inhibitors and/or MTP inhibitors are disclosed in commonly assigned U.S. Pat. No. 5,919,795.

A variety of apo B secretion/MTP inhibitors are known to one of ordinary skill in the art. Although any apo B secretion/MTP inhibitor may be used in the practice of the methods and pharmaceutical compositions of the instant invention, generally preferred apo B secretion/MTP inhibitors include those compounds that are disclosed in, for example, European Patent Application Publication Numbers EP 643057, EP 719763, EP 753517, EP 764647, EP 765878, EP 779276, EP 779279, EP 799828, EP 799829, EP 802186, EP 802188, EP 802192, and EP 802197; PCT Application Publication Numbers WO 96/13499, WO 96/33193, WO 96/40640, WO 97/26240, WO 97/43255, WO 97/43257, WO 98/16526 and WO 98/23593; and U.S. Pat. Nos. 5,595,872; 5,646,162; 5,684,014; 5,712,279; 5,739,135 and 5,789,197.

Especially preferred apo-B secretion/MTP inhibitors are those biphenyl-2-carboxylic acid-tetrahydroisoquinolin-6-yl amide derivatives disclosed in PCT Application Publication Numbers WO 96/40640 and WO 98/23593. Especially preferred apo B secretion/MTP inhibitors disclosed in PCT Application Publication Numbers WO 96/40640 and WO 98/23593, and useful in the methods and pharmaceutical compositions of the present invention, are 4'-trifluoromethyl-biphenyl-2-carboxylic acid-[2-(1H-[1,2,4]triazol-3-ylmethyl)-1,2,3,4-tetrahydroisoquin-6-yl]-amide and 4'-trifluoromethyl-biphenyl-2-carboxylic acid-[2-(acetylaminoethyl)-1,2,3,4-tetrahydroisoquinolin-6-yl]-amide.

Another especially preferred class of apo B secretion/MTP inhibitors is disclosed in U.S. Pat. Nos. 5,595,872; 5,721,279; 5,739,135 and 5,789,197.

Especially preferred apo B secretion/MTP inhibitors disclosed in U.S. Pat. Nos. 5,595,872; 5,721,279; 5,739,135 and 5,789,197 and useful in the methods and pharmaceutical compositions of the present invention, are 9-(4-{4-[4'trifluoromethyl-biphenyl-2-carbonyl)-amino]-piperidin-1-yl}-butyl-9H-fluorene-9-carboxylic acid-(2,2,2-trifluoroethyl)-amide and 9-{4-[4-(2-benzothiazol-2-yl-benzoylamino)-piperidin-1-yl]-butyl}9H-fluorene-9-carboxylic acid-(2,2,2-trifluoroethyl)-amide.

Another class of especially preferred apo B secretion/MTP inhibitors is disclosed in PCT Application Publication Number WO 98/16526.

Especially preferred apo B secretion/MTP inhibitors disclosed in PCT Application Publication Number WO 98/16526, and useful in the methods and pharmaceutical compositions of the present invention, are [11a-R]-8-[(4-cyanophenyl)methoxy]-2-cyclopentyl-7-(prop-2-enyl)-2,3,11,11a-tetrahydro-6H-pyrazino(1,2b]isoquinoline-1,4-dione and [11a-R]-cyclopentyl-7-(prop-2-enyl)-8-[(pyridin-2-yl)methoxy]-2,3,11,11a-tetrahydro-6H-pyrazino[1,2b]isoquinoline-1,4-dione.

Another especially preferred class of apo B secretion/MTP inhibitors is disclosed in U.S. Pat. No. 5,684,014.

An especially preferred apo B secretion/MTP inhibitor disclosed in U.S. Pat. No. 5,684,014, and useful in the methods and pharmaceutical compositions of the present invention, is 2-cyclopentyl-2-[4-(2,4-dimethyl-pyrido[2,3-b]indol-9-ylmethyl)-phenyl]-N-(2-hydroxy-1-phenyl-ethyl)-acetamide.

Yet another class of especially preferred apo B secretion/MTP inhibitors is disclosed in U.S. Pat. No. 5,646,162.

An especially preferred apo B secretion/MTP inhibitor disclosed in U.S. Pat. No. 5,646,162 and useful in the methods and pharmaceutical compositions of the present invention, is 2-cyclopentyl-N-(2-hydroxy-1-phenylethyl)-2-[4-(quinolin-2-ylmethoxy)-phenyl]-acetamide.

Additional apo B secretion/MTP inhibitors that can be used in combination with compounds identified by the present invention are disclosed in U.S. provisional patent application No. 60/164,803, filed Nov. 11, 1999. Examples of specific preferred apo B secretion/MTP inhibitors disclosed in this application include:

7-amino-quinoline-3-carboxylic acid ethyl ester;

7-[(4'-trifluoromethyl-biphenyl-2-carbonyl)-amino]-quinoline-3-carboxylic acid ethyl ester;

7-[(4'-trifluoromethyl-biphenyl-2-carbonyl)-amino]-quinoline-3-carboxylic acid;

7-[(4'-trifluoromethyl-biphenyl-2-carbonyl)-amino]-quinoline-3-carboxylic acid (dipyridin-2-yl-methyl)-amide;

7-[(4'-trifluoromethyl-biphenyl-2-carbonyl)-amino]-quinoline-3-carboxylic acid (dipyridin-2-yl-methyl)-amide, ethanesulfonate;

7-[(4'-trifluoromethyl-biphenyl-2-carbonyl)-amino]-quinoline-3-carboxylic acid (dipyridin-2-yl-methyl)-amide, bis-ethanesulfonate;

7-[(4'-trifluoromethyl-biphenyl-2-carbonyl)-amino]-quinoline-3-carboxylic acid (phenyl-pyridin-2-yl-methyl)-amide;

7-[(4'-trifluoromethyl-biphenyl-2-carbonyl)-amino]-quinoline-3-carboxylic acid (phenyl-pyridin-2-yl-methyl)-amide, ethanesulfonate;

(S)-7-[(4'-trifluoromethyl-biphenyl-2-carbonyl)-amino]-quinoline-3-carboxylic acid (phenyl-pyridin-2-yl-methyl)-amide;

(S)-7-[(4'-trifluoromethyl-biphenyl-2-carbonyl)-amino]-quinoline-3-carboxylic acid (phenyl-pyridin-2-yl-methyl)-amide, ethanesulfonate;

(S)-7-[(4'-trifluoromethyl-biphenyl-2-carbonyl)-amino]-quinoline-3-carboxylic acid (phenyl-pyridin-2-yl-methyl)-amide, bis-ethanesulfonate;

(R)-7-[(4'-trifluoromethyl-biphenyl-2-carbonyl)-amino]-quinoline-3-carboxylic acid (phenyl-pyridin-2-yl-methyl)-amide;

(R)-7-[(4'-trifluoromethyl-biphenyl-2-carbonyl)-amino]-quinoline-3-carboxylic acid (phenyl-pyridin-2-yl-methyl)-amide, ethanesulfonate;

7-[(4'-trifluoromethyl-biphenyl-2-carbonyl)-amino]-quinoline-3-carboxylic acid (phenyl-pyridin-2-yl-methyl)-amide, bis-ethanesulfonate;

7-[(4'-trifluoromethyl-biphenyl-2-carbonyl)-amino]-quinoline-3-carboxylic acid (1-carbamoyl-2-phenyl-ethyl)-amide;

7-[(4'-trifluoromethyl-biphenyl-2-carbonyl)-amino]-quinoline-3-carboxylic acid (carbamoyl-phenyl-methyl)-amide;

7-[(4'-trifluoromethyl-biphenyl-2-carbonyl)-amino]-quinoline-3-carboxylic acid propylamide;

7-[(4'-trifluoromethyl-biphenyl-2-carbonyl)-amino]-quinoline-3-carboxylic acid (2,2,2-trifluoro-ethyl)-amide;

7-[(4'-trifluoromethyl-biphenyl-2-carbonyl)-amino]-quinoline-3-carboxylic acid (1-methyl-1-phenyl-ethyl)-amide;

7-[(4'-trifluoromethyl-biphenyl-2-carbonyl)-amino]-quinoline-3-carboxylic acid cyclopentylamide;

7-[(4'-trifluoromethyl-biphenyl-2-carbonyl)-amino]-quinoline-3-carboxylic acid (1-phenyl-propyl)-amide;

(R)-7-[(4'-trifluoromethyl-biphenyl-2-carbonyl)-amino]-quinoline-3-carboxylic acid (1-phenyl-ethyl)-amide, ethanesulfonate;

7-[(4'-trifluoromethyl-biphenyl-2-carbonyl)-amino]-quinoline-3-carboxylic acid (1-phenyl-ethyl)-amide;
7-[(4'-trifluoromethyl-biphenyl-2-carbonyl)-amino]-quinoline-3-carboxylic acid (1-pyridin-2-yl-propyl)-amide;
(R)-7-[(4'-trifluoromethyl-biphenyl-2-carbonyl)-amino]-quinoline-3-carboxylic acid (1-pyridin-2-yl-propyl)-amide;
(R)-7-[(4'-trifluoromethyl-biphenyl-2-carbonyl)-amino]-quinoline-3-carboxylic acid (1-pyridin-2-yl-propyl)-amide, ethanesulfonate;
(S)-7-[(4'-trifluoromethyl-biphenyl-2-carbonyl)-amino]-quinoline-3-carboxylic acid (1-pyridin-2-yl-propyl)-amide;
(S)-7-[(4'-trifluoromethyl-biphenyl-2-carbonyl)-amino]-quinoline-3-carboxylic acid (1-pyridin-2-yl-propyl)-amide ethanesulfonate;
7-[(4'-trifluoromethyl-biphenyl-2-carbonyl)-amino]-quinoline-3-carboxylic acid (1-pyridin-2-yl-propyl)-amide, ethanesulfonate;
7-[(4'-trifluoromethyl-biphenyl-2-carbonyl)-amino]-quinoline-3-carboxylic acid (pyridin-2-ylmethyl)-amide, ethanesulfonate;
7-[(4'-trifluoromethyl-biphenyl-2-carbonyl)-amino]-quinoline-3-carboxylic acid (2-pyridin-2-yl-ethyl)-amide, ethanesulfonate;
7-[(4'-trifluoromethyl-biphenyl-2-carbonyl)-amino]-quinoline-3-carboxylic acid ethylamide, ethanesulfonate;
7-[(4'-trifluoromethyl-biphenyl-2-carbonyl)-amino]-quinoline-3-carboxylic acid butylamide, ethanesulfonate;
7-[(4'-trifluoromethyl-biphenyl-2-carbonyl)-amino]-quinoline-3-carboxylic acid (thiophen-2-yl ethyl)-amide, ethanesulfonate;
7-[(4'-trifluoromethyl-biphenyl-2-carbonyl)-amino]-quinoline-3-carboxylic acid (1-methyl-1-pyridin-2-yl-ethyl)-amide;
(S)-7-[(4'-trifluoromethyl-biphenyl-2-carbonyl)-amino]-quinoline-3-carboxylic acid (1-pyridin-2-yl-ethyl)-amide;
(R)-7-[(4'-trifluoromethyl-biphenyl-2-carbonyl)-amino]-quinoline-3-carboxylic acid (1-pyridin-2-yl-ethyl)-amide ethanesulfonate;
7-[(4'-trifluoromethyl-biphenyl-2-carbonyl)-amino]-quinoline-3-carboxylic acid (1-pyridin-2-yl-ethyl)-amide;
7-[(4-trifluoromethyl-biphenyl-2-carbonyl)-amino]-quinoline-3-carboxylic acid (1-pyridin-2-yl-ethyl)-amide ethanesulfonate;
7-[(4'-trifluoromethyl-biphenyl-2-carbonyl)-amino]-quinoline-3-carboxylic acid amide;
7-[(4'-trifluoromethyl-biphenyl-2-carbonyl)-amino]-quinoline-3-carboxylic acid benzylamide;
7-[(4'-trifluoromethyl-biphenyl-2-carbonyl)-amino]-quinoline-3-carboxylic acid 4-methoxy-benzylamide;
7-[(4'-trifluoromethyl-biphenyl-2-carbonyl)-amino]-quinoline-3-carboxylic acid 4-chloro-benzylamide;
7-[(4'-trifluoromethyl-biphenyl-2-carbonyl)-amino]-quinoline-3-carboxylic acid 4-methyl-benzylamide;
7-[(4'-trifluoromethyl-biphenyl-2-carbonyl)-amino]-quinoline-3-carboxylic acid cyclopropylmethyl-amide;
7-[(4'-trifluoromethyl-biphenyl-2-carbonyl)-amino]-quinoline-3-carboxylic acid 4-fluoro-benzylamide;
7-[(4'-trifluoromethyl-biphenyl-2-carbonyl)-amino]-quinoline-3-carboxylic acid isopropyl-amide;
7-[(4'-trifluoromethyl-biphenyl-2-carbonyl)-amino]-quinoline-3-carboxylic acid benzhydryl-amide;
7-[(4'-trifluoromethyl-biphenyl-2-carbonyl)-amino]-quinoline-3-carboxylic acid cyclopropylamide;
7-[(4'-trifluoromethyl-biphenyl-2-carbonyl)-amino]-quinoline-3-carboxylic acid [1-(4-fluoro-phenyl)-ethyl]-amide;
7-[(4'-trifluoromethyl-biphenyl-2-carbonyl)-amino]-quinoline-3-carboxylic acid 3-methyl-benzylamide;
7-[(4'-trifluoromethyl-biphenyl-2-carbonyl)-amino]-quinoline-3-carboxylic acid 3-methoxy-benzylamide;
7-[(4'-trifluoromethyl-biphenyl-2-carbonyl)-amino]-quinoline-3-carboxylic acid 3-chloro-benzylamide;
7-[(4'-trifluoromethyl-biphenyl-2-carbonyl)-amino]-quinoline-3-carboxylic acid 2-fluoro-benzylamide;
7-[(4'-trifluoromethyl-biphenyl-2-carbonyl)-amino]-quinoline-3-carboxylic acid 3-fluoro-benzylamide;
7-[(4'-trifluoromethyl-biphenyl-2-carbonyl)-amino]-quinoline-3-carboxylic acid 2-methyl-benzylamide;
7-[(4'-trifluoromethyl-biphenyl-2-carbonyl)-amino]-quinoline-3-carboxylic acid 2-methoxy-benzylamide;
7-[(4'-trifluoromethyl-biphenyl-2-carbonyl)-amino]-quinoline-3-carboxylic acid 2-chloro-benzylamide;
4'-trifluoromethyl-biphenyl-2-carboxylic acid [3-(pyrrolidine-1-carbonyl)-quinolin-7-yl]-amide;
4'-trifluoromethyl-biphenyl-2-carboxylic acid [3-(morpholine-4-carbonyl)-quinolin-7-yl]-amide;
7-[(4'-trifluoromethyl-biphenyl-2-carbonyl)-amino]-quinoline-3-carboxylic acid diethylamide;
4'-trifluoromethyl-biphenyl-2-carboxylic acid [3-(piperidine-1-carbonyl)-quinolin-7-yl]-amide; and pharmaceutically acceptable salts and prodrugs thereof, and salts of the prodrugs.

Specific cholesterol absorption inhibitors and cholesterol biosynthesis inhibitors are described in detail below. Additional cholesterol absorption inhibitors are known to those skilled in the art and are described, for example, in WO 94/00480.

Any HMG-CoA reductase inhibitor may be employed as an additional compound in the combination therapy aspect of the present invention. The term HMG-CoA reductase inhibitor refers to a compound that inhibits the biotransformation of hydroxymethylglutaryl-coenzyme A to mevalonic acid as catalyzed by the enzyme HMG-CoA reductase. Such inhibition may be determined readily by one of skill in the art according to standard assays (e.g., *Methods of Enzymology*, 71: 455–509 (1981); and the references cited therein). A variety of these compounds are described and referenced below. U.S. Pat. No. 4,231,938 discloses certain compounds isolated after cultivation of a microorganism belonging to the genus Aspergillus, such as lovastatin. Also, U.S. Pat. No. 4,444,784 discloses synthetic derivatives of the aforementioned compounds, such as simvastatin. Additionally, U.S. Pat. No. 4,739,073 discloses certain substituted indoles, such as fluvastatin. Further, U.S. Pat. No. 4,346,227 discloses ML-236B derivatives, such as pravastatin. In addition, EP 491,226 teaches certain pyridyldihydroxyheptenoic acids, such as rivastatin. Also, U.S. Pat. No. 4,647,576 discloses certain 6-[2-(substituted-pyrrol-1-yl)-alkyl]-pyran-2-ones such as atorvastatin. Other HMG-CoA reductase inhibitors will be known to those skilled in the art. Examples of marketed products containing HMG-CoA reductase inhibitors include Baycol®, Lescol®, Lipitor®, Mevacor®, Pravachol® and Zocor®.

Any HMG-CoA synthase inhibitor may be used as an additional compound in the combination therapy aspect of this invention. The term HMG-CoA synthase inhibitor refers to a compound that inhibits the biosynthesis of hydroxymethylglutaryl-coenzyme A from acetyl-coenzyme A and acetoacetyl-coenzyme A, catalyzed by the enzyme HMG-CoA synthase. Such inhibition may be determined readily by one of skill in the art according to standard assays (e.g., *Methods of Enzymology*, 35: 155–160 (1975); and *Methods of Enzymology*, 110: 19–26 (1985); and the references cited therein). A variety of these compounds are described and referenced below. U.S. Pat. No. 5,120,729 discloses certain beta-lactam derivatives. U.S. Pat. No. 5,064,856 discloses certain spiro-lactone derivatives prepared by culturing the microorganism MF5253. U.S. Pat. No. 4,847,271 discloses certain oxetane compounds such as 11-(3-hydroxymethyl-4-oxo-2-oxetayl)-3,5,7-trimethyl-2,4-undecadienoic acid derivatives. Other HMG-CoA synthase inhibitors useful in the methods, compositions and kits of the present invention will be known to those skilled in the art.

Any compound that decreases HMG-CoA reductase gene expression may be used as an additional compound in the combination therapy aspect of this invention. These agents may be HMG-CoA reductase transcription inhibitors that block the transcription of DNA or translation inhibitors that prevent translation of mRNA coding for HMG-CoA reductase into protein. Such inhibitors may either affect transcription or translation directly, or may be biotransformed into compounds that have the aforementioned attributes by one or more enzymes in the cholesterol biosynthetic cascade or may lead to the accumulation of an isoprene metabolite that has the aforementioned activities. Such regulation is readily determined by those skilled in the art according to standard assays (*Methods of Enzymology,* 110: 9–19 1985). Several such compounds are described and referenced below; however, other inhibitors of HMG-CoA reductase gene expression will be known to those skilled in the art, for example, U.S. Pat. No. 5,041,432 discloses certain 15-substituted lanosterol derivatives that are inhibitors of HMG-CoA reductase gene expression. Other oxygenated sterols that suppress the biosynthesis of HMG-CoA reductase are discussed by E. I. Mercer (*Prog. Lip. Res.,* 32:357–416 1993).

Any compound having activity as a CETP inhibitor can serve as the second compound in the combination therapy aspect of the instant invention. The term CETP inhibitor refers to compounds that inhibit the cholesteryl ester transfer protein (CETP) mediated transport of various cholesteryl esters and triglycerides from HDL to LDL and VLDL. A variety of these compounds are described and referenced below; however, other CETP inhibitors will be known to those skilled in the art. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot.,* 49(8): 815–816 (1996), and *Bioorg. Med. Chem. Lett.;* 6:1951–1954 (1996), respectively.

Preferred CETP inhibitors that can be used in combination with a compound of the present invention include those described below in U.S. patent application Ser. No. 09/391, 152, filed Sep. 7, 1999.

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid 2-hydroxy-ethyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid propyl ester; and

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid propyl ester,

[2S,4S]4-[(3,5-bis-trifluoromethyl-benzyl)-methoxycarbonyl-amino]-2-isopropyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-6-chloro-2-cyclopropyl-3,4-dihydro-2H-quinoline-1-carboxylic acid isopropyl ester;

[2S,4S]2-cyclopropyl-4-[(3,5-dichloro-benzyl)-methoxycarbonyl-amino]-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid tert-butyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-cyclobutyl-6-trifluoromethyl-3,4-dihydro-2H-quinoline-1-carboxylic acid isopropyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid 2-hydroxy-ethyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid propyl ester; and

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid propyl ester, and pharmaceutically acceptable salts and prodrugs thereof and salts of the prodrugs.

Any ACAT inhibitor can serve as an additional compound in the combination therapy aspect of this invention. The term ACAT inhibitor refers to a compound that inhibits the intracellular esterification of dietary cholesterol by the enzyme acyl CoA: cholesterol acyltransferase. Such inhibition may be determined readily by one of skill in the art according to standard assays, such as the method of Heider et al. described in *Journal of Lipid Research.,* 24:1127

(1983). A variety of these compounds are described and referenced below; however, other ACAT inhibitors will be known to those skilled in the art. U.S. Pat. No. 5,510,379 discloses certain carboxysulfonates, while WO 96/26948 and WO 96/10559 both disclose urea derivatives having ACAT inhibitory activity.

Any compound having activity as a squalene synthetase inhibitor can serve as an additional compound in the combination therapy aspect of the instant invention. The term squalene synthetase inhibitor refers to compounds that inhibit the condensation of two molecules of farnesylpyrophosphate to form squalene, a reaction that is catalyzed by the enzyme squalene synthetase. Such inhibition is readily determined by those skilled in the art according to standard methodology (*Methods of Enzymology*, 15:393–454 (1969); and *Methods of Enzymology*, 110: 359–373 (1985); and references cited therein). A summary of squalene synthetase inhibitors has been complied in *Curr. Op. Ther. Patents*, 861–4, (1993). European patent application publication Number 0 567 026 A1 discloses certain 4,1-benzoxazepine derivatives as squalene synthetase inhibitors and their use in the treatment of hypercholesterolemia and as fungicides. European patent application publication Number 0 645 378 A1 discloses certain seven- or eight-membered heterocycles as squalene synthetase inhibitors and their use in the treatment and prevention hypercholesterolemia and fungal infections. European patent application publication Number 0 645 377 A1 discloses certain benzoxazepine derivatives as squalene synthetase inhibitors useful for the treatment of hypercholesterolemia or coronary sclerosis. European patent application publication Number 0 611 749 A1 discloses certain substituted amic acid derivatives useful for the treatment of arteriosclerosis. European patent application publication Number 0 705 607 A2 discloses certain condensed seven- or eight-membered heterocyclic compounds useful as antihypertriglyceridemic agents. PCT publication WO 96/09827 discloses certain combinations of cholesterol absorption inhibitors and cholesterol biosynthesis inhibitors including benzoxazepine derivatives and benzothiazepine derivatives. European patent application publication Number 0 701 725 A1 discloses a process for preparing certain optically-active compounds, including benzoxazepine derivatives, having plasma cholesterol and triglyceride lowering activities.

Other compounds that are marketed for hyperlipidemia, including hypercholesterolemia, and which are intended to help prevent or treat atherosclerosis, include bile acid sequestrants, such as Colestid®, LoCholest®, and Questran®; and fibric acid derivatives, such as Atromid®, Lopid®, and Tricor®. These compounds can also be used in combination with a compound of the present invention.

It is also contemplated that the compounds of the present invention be administered with a lipase inhibitor and/or a glucosidase inhibitor, which are typically used in the treatment of conditions resulting from the presence of excess triglycerides, free fatty acids, cholesterol, cholesterol esters or glucose including, inter alia, obesity, hyperlipidemia, hyperlipoproteinemia, Syndrome X, and the like.

In a combination with a compound of the present invention, any lipase inhibitor or glucosidase inhibitor may be employed. Preferred lipase inhibitors comprise gastric or pancreatic lipase inhibitors. Preferred glucosidase inhibitors comprise amylase inhibitors.

A lipase inhibitor is a compound that inhibits the metabolic cleavage of dietary triglycerides into free fatty acids and monoglycerides. Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid-phospholipid micelles, which are subsequently absorbed at the level of the brush border of the small intestine. The micelles eventually enter the peripheral circulation as chylomicrons. Accordingly, compounds, including lipase inhibitors that selectively limit or inhibit the absorption of ingested fat precursors are useful in the treatment of conditions including obesity, hyperlipidemia, hyperlipoproteinemia, Syndrome X, and the like.

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions.

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., *Gastroenterology*, 92, 125 (1987).

A variety of lipase inhibitors are known to one of ordinary skill in the art. However, in the practice of the methods, pharmaceutical compositions, and kits of the instant invention, generally preferred lipase inhibitors are those inhibitors that are selected from the group consisting of lipstatin, tetrahydrolipstatin (orlistat), FL-386, WAY-121898, Bay-N-3176, valilactone, esterastin, ebelactone A, ebelactone B and RHC 80267.

The pancreatic lipase inhibitors lipstatin, 2S, 3S, 5S, 7Z, 10Z)-5-[(S)-2-formamido-4-methyl-valeryloxy]-2-hexyl-3-hydroxy-7,10-hexadecanoic acid lactone, and tetrahydrolipstatin (orlistat), 2S, 3S, 5S)-5-[(S)-2-formamido-4-methyl-valeryloxy]-2-hexyl-3-hydroxy-hexadecanoic acid lactone, and the variously substituted N-formylleucine derivatives and stereoisomers thereof, are disclosed in U.S. Pat. No. 4,598,089.

The pancreatic lipase inhibitor FL-386, 1-[4-(2-methylpropyl)cyclohexyl]-2-[(phenylsulfonyl)oxy]-ethanone, and the variously substituted sulfonate derivatives related thereto, are disclosed in U.S. Pat. No. 4,452,813.

The pancreatic lipase inhibitor WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151.

The lipase inhibitor Bay-N-3176, N-3-trifluoromethylphenyl-N'-3-chloro-4'-trifluoromethylphenylurea, and the various urea derivatives related thereto, are disclosed in U.S. Pat. No. 4,405,644.

The pancreatic lipase inhibitor valilactone, and a process for the preparation thereof by the microbial cultivation of Actinomycetes strain MG147—CF2, are disclosed in Kitahara, et al., *J. Antibiotics*, 40 (11), 1647–1650 (1987).

The lipase inhibitor esteracin, and certain processes for the preparation thereof by the microbial cultivation of Streptomyces strain ATCC 31336, are disclosed in U.S. Pat. Nos. 4,189,438 and 4,242,453.

The pancreatic lipase inhibitors ebelactone A and ebelactone B, and a process for the preparation thereof by the microbial cultivation of Actinomycetes strain MG7-G1, are disclosed in Umezawa, et al., *J. Antibiotics*, 33, 1594–1596 (1980). The use of ebelactones A and B in the suppression of monoglyceride formation is disclosed in Japanese Kokai 08-143457, published Jun. 4, 1996.

The lipase inhibitor RHC 80267, cyclo-O,O'-[(1,6-hexanediyl)-bis-(iminocarbonyl)]dioxime, and the various bis(iminocarbonyl)dioximes related thereto may be prepared as described in Petersen et al., *Liebig's Annalen*, 562, 205–229 (1949). The ability of RHC 80267 to inhibit the activity of myocardial lipoprotein lipase is disclosed in Carroll et al., *Lipids*, 27, pp. 305–307 (1992) and Chuang et al., *J. Mol. Cell Cardiol.*, 22, 1009–1016 (1990).

A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known that both hypoglycemias and chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom.

In combination with a compound of the present invention, any glucosidase inhibitor may be employed; however, a generally preferred glucosidase inhibitor comprises an amylase inhibitor. An amylase inhibitor is a glucosidase inhibitor that inhibits the enzymatic degradation of starch or glycogen into maltose. The inhibition of such enzymatic degradation is beneficial in reducing amounts of bioavailable sugars, including glucose and maltose, and the concomitant deleterious conditions resulting therefrom.

A variety of glucosidase and amylase inhibitors are known to one of ordinary skill in the art. However, in the practice of the methods, pharmaceutical compositions and kits of the instant invention, generally preferred glucosidase inhibitors are those inhibitors that are selected from the group consisting of acarbose, adiposine, voglibose, miglitol, emiglitate, MDL-25637, camiglibose, tendamistate, AI-3688, trestatin, pradimicin-Q and salbostatin.

The glucosidase inhibitor acarbose, O-4,6-dideoxy-4-[[(1S,4R,5S,6S)-4,5,6-trihydroxy-3-(hydroxymethyl)-2-cyclohexen-1-yl]amino]-α-glucopyranosyl-(1→4)-O-α-D-glucopyranosyl-(1→4)-D-glucose, the various amino sugar derivatives related thereto and a process for the preparation thereof by the microbial cultivation of Actinoplanes strains SE 50 (CBS 961.70), SB 18 (CBS 957.70), SE 82 (CBS 615.71), SE 50/13 (614.71) and SE 50/110 (674.73) are disclosed in U.S. Pat. Nos. 4,062,950 and 4,174,439 respectively.

The glucosidase inhibitor adiposine, consisting of adiposine forms 1 and 2, is disclosed in U.S. Pat. No. 4,254,256. Additionally, a process for the preparation and purification of adiposine is disclosed in Namiki et al., *J. Antiobiotics*, 35, 1234–1236 (1982).

The glucosidase inhibitor voglibose, 3,4-dideoxy-4-[[2-hydroxy-1-(hydroxymethyl)ethyl]amino]-2-C-(hydroxymethyl)-D-epi-inositol, and the various N-substituted pseudo-aminosugars related thereto, are disclosed in U.S. Pat. No. 4,701,559.

The glucosidase inhibitor miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436.

The glucosidase inhibitor emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof, are disclosed in U.S. Pat. No. 5,192,772.

The glucosidase inhibitor MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765.

The glucosidase inhibitor camiglibose, methyl 6-deoxy-6-[(2R,3R,4R,5S)-3,4,5-trihydroxy-2-(hydroxymethyl)piperidino]-α-D-glucopyranoside sesquihydrate, the deoxynojirimycin derivatives related thereto, the various pharmaceutically acceptable salts thereof and synthetic methods for the preparation thereof, are disclosed in U.S. Pat. Nos. 5,157,116 and 5,504,078.

The amylase inhibitor tendamistat, the various cyclic peptides related thereto and processes for the preparation thereof by the microbial cultivation of *Streptomyces tendae* strains 4158 or HAG 1226, are disclosed in U.S. Pat. No. 4,451,455.

The amylase inhibitor AI-3688, the various cyclic polypeptides related thereto, and a process for the preparation thereof by the microbial cultivation of *Streptomyces aureofaciens* strain FH 1656, are disclosed in U.S. Pat. No. 4,623,714.

The amylase inhibitor trestatin, consisting of a mixture of trestatin A, trestatin B and trestatin C, the various trehalose-containing aminosugars related thereto and a process for the preparation thereof by the microbial cultivation of *Streptomyces dimorphogenes* strains NR-320-OM7HB and NR-320-OM7HBS, are disclosed in U.S. Pat. No. 4,273,765.

The glucosidase inhibitor pradimicin-Q and a process for the preparation thereof by the microbial cultivation of *Actinomadura verrucospora* strains R103-3 or A10102, are disclosed in U.S. Pat. Nos. 5,091,418 and 5,217,877 respectively.

The glycosidase inhibitor salbostatin, the various pseudosaccharides related thereto, the various pharmaceutically acceptable salts thereof and a process for the preparation thereof by the microbial cultivation of *Streptomyces albus* strain ATCC 21838, are disclosed in U.S. Pat. No. 5,091,524.

Preferred lipase inhibitors comprise compounds selected from the group consisting of lipstatin, tetrahydrolipstatin, FL-386, WAY-121898, Bay-n-3176, valilactone, esteracin, ebelactone A, ebelactone B, RHC 80267, stereoisomers thereof, and pharmaceutically acceptable salts of said compounds and stereoisomers. The compound tetrahydrolipstatin is especially preferred.

Preferred glucosidase inhibitors comprise compounds selected from the group consisting of acarbose, adiposine, voglibose, miglitol, emiglitate, MDL-25637, camiglibose, pradimicin-Q, and salbostatin. An especially preferred glucosidase inhibitor is acarbose. Especially preferred glucosidase inhibitors further comprise amylase inhibitors that are selected from the group consisting of tendamistate, AI-3688 and trestatin.

In another aspect of the present invention, the compounds of Formula I can be used in combination with an additional anti-obesity agent. The additional anti-obesity agent is preferably selected from the group consisting of a $\beta_3$-adrenergic receptor agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a melanocyte-stimulating hormone receptor analog, a cannabinoid receptor antagonist, a melanin concentrating hormone antagonist, leptin, a leptin analog, a leptin receptor agonist, a galanin antagonist, a lipase inhibitor, a bombesin agonist, a neuropeptide-Y antagonist, a thyromimetic agent, dehydroepiandrosterone or an analog thereof, a glucocorticoid receptor agonist or antagonist, an orexin receptor antagonist, a urocortin binding protein antagonist, a glucagon-like peptide-1 receptor agonist, and a ciliary neurotrophic factor.

Especially preferred anti-obesity agents comprise those compounds selected from the group consisting of sibutramine, fenfluramine, dexfenfluramine, bromocriptine, phentermine, ephedrine, leptin, phenylpropanolamine pseudoephedrine, {4-[2-(2-[6-aminopyridin-3-yl]-2(R)-hydroxyethylamino)ethoxy]phenyl}acetic acid, {4-[2-(2-[6-aminopyridin-3-yl]-2(R)-hydroxyethylamino)ethoxy]phenyl}benzoic acid, {4-[2-(2-[6-aminopyridin-3-yl]-2(R)-hydroxyethylamino)ethoxy]phenyl}propionic acid, and {4-[2-(2-[6-aminopyridin-3-yl]-2(R)-hydroxyethylamino)ethoxy]phenoxy}acetic acid.

The compounds of the present invention can also be used in combination with an antihypertensive agent. Examples of presently marketed products containing antihypertensive agents include calcium channel blockers, such as Cardizem®, Adalat®, Calan®, Cardene®, Covera®, Dilacor®, DynaCirc®, Procardia XL®, Sular®, Tiazac®, Vascor®, Verelan®, Isoptin®, Nimotop®, Norvasc®, and Plendil®; angiotensin converting enzyme (ACE) inhibitors, such as Accupril®, Altace®, Captopril®, Lotensin®, Mavik®, Monopril®, Prinivil®, Univasc®, Vasotec® and Zestril®. In addition, diuretics and combinations of the above antihypertensive agents have been employed and are contemplated to be used in combination with a compound of the present invention.

The compounds of the present invention can also be used in combination with an antidepressant. Examples of marketed antidepressants that can be used in combination with a compound of the present invention include monoamine oxidase inhibitors such as Nardil® and Parnate®; selective seratonin reuptake inhibitors, such as Paxil®, Prozac®, and Zoloft®; triclyclics, such as Asendin®, Elavil®, Etrafon®, Limbitrol®, Norpramin®, Pamelor®, Sinequan®, Surmontil®, Tofranil®, Triavil®, and Vivactil®. Additional compounds that are used to treat depression and that can be used in combination with a compound of the present invention include Desyrel®, Effexor®, Remeron®, Serzone®, and Wellbutrin®.

The compounds of the present invention can also be used in combination with a compound useful to treat osteoporosis. Examples of marketed products containing active agents that can be used in combination with a compound of the present invention include biphosphonates such as Fosamax® and hormonal agents such as calcitonin and estrogens. In addition, Evista® may be used in combination with a compound of the present invention.

The compounds of the present invention are administered to a patient in a therapeutically effective amount. The compounds can be administered alone or as part of a pharmaceutically acceptable composition. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially in any order. For example, in the case of tablets, the active compounds may be found in one tablet or in separate tablets, which can be administered at once or sequentially. In addition, it should be recognized that the compositions may be different forms. For example, one or more compounds may be delivered via a tablet, while another is administered via injection or orally as a syrup. All combinations, delivery methods and administration sequences are contemplated.

Since one aspect of the present invention contemplates the treatment of the disease/conditions with a combination of pharmaceutically active agents that may be administered separately, the invention further relates to combining separate pharmaceutical compositions in kit form. The kit comprises two separate pharmaceutical compositions: a compound of the present invention, a prodrug thereof, or a salt of such compound or prodrug; and an additional pharmaceutically active compound. The kit comprises a container for containing the separate compositions, such as a divided bottle or a divided foil packet. Additional examples of containers include syringes, boxes, bags, and the like. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet.

Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . . . Second Week, Monday, Tuesday, . . . " etc. Other variations of memory aids will be readily apparent. A "daily dose" can be a single tablet or capsule or several pills or capsules to be taken on a given day. Also, a daily dose of compounds of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active agents, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration are preferably suppositories, which can be prepared by mixing a compound of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.7 to about 7,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is well within the ordinary skill in the art in view of this disclosure. It is also noted that the compounds of the present invention can be used in sustained release, controlled release, and delayed release formulations, which are well known in the art.

The following paragraphs describe exemplary formulations, dosages, etc. useful for non-human animals. The administration of a compound of the present invention can be effected orally or non-orally, for example by injection. An amount of a compound of the present invention is administered such that an effective dose is received, generally a daily dose which, when administered orally to an animal is usually between 0.01 and 100 mg/kg of body weight, preferably between 0.1 and 50 mg/kg of body weight. Conveniently, the compound can be carried in the drinking water so that a therapeutic dosage of the compound is ingested with the daily water supply. The compound can be directly metered into drinking water, preferably in the form of a liquid, water-soluble concentrate (such as an aqueous solution of a water soluble salt). Conveniently, the compound can also be added directly to the feed, as such, or in the form of an animal feed supplement, also referred to as a premix or concentrate. A premix or concentrate of the compound in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the compound in the finished feed with which the premix is blended. It is important that the compound be thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of active compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Preferred medicated swine, cattle, sheep and goat feeds generally contain from about 1 to about 400 grams of a compound of the present invention per ton of feed, the optimum amount for these animals usually being about 50 to about 300 grams per ton of feed.

Preferred poultry and domestic pet feeds usually contain about 1 to about 400 grams and preferably about 10 to about 400 grams of a compound of the present invention per ton of feed.

For parenteral administration in animals, the compounds of the present invention may be prepared in the form of a paste or a pellet and administered as an implant, usually under the skin of the head or ear of the animal.

In general, parenteral administration involves injection of a sufficient amount of a compound of the present invention to provide the animal with about 0.01 to about 100 mg/kg of body weight per day of the active ingredient. The preferred dosage for poultry, swine, cattle, sheep, goats and domestic pets is in the range of from about 0.1 to about 50 mg/kg/day.

Paste formulations can be prepared by dispersing a compound of the present invention in pharmaceutically acceptable oil such as peanut oil, sesame oil, corn oil or the like.

Pellets containing an effective amount of a compound of the present invention can be prepared by admixing a compound of the present invention with a diluent such as carbowax, carnauba wax, and the like, and a lubricant, such as magnesium or calcium stearate, can be added to improve the pelleting process.

It is, of course, recognized that more than one pellet may be administered to an animal to achieve the desired dose level. Moreover, it has been found that implants may also be made periodically during the animal treatment period in order to maintain the proper active agent level in the animal's body.

The terms pharmaceutically acceptable salts, esters, amides, or prodrugs means the carboxylate salts, amino acid addition salts, esters, amides, and prodrugs of a compound that are, within the scope of sound medical judgment, suitable for use with patients without undue toxicity, irritation, allergic response, and the like, commensurate with a reasonable benefit/risk ratio, and effective for their intended use, as well as the zwitterionic forms, where possible.

The term "salts" refers to inorganic and organic salts of a compound of the present invention. These salts can be prepared in situ during the final isolation and purification of a compound, or by separately reacting a compound with a suitable organic or inorganic acid and isolating the salt thus formed. Representative salts include the hydrobromide, hydrochloride, sulfate, bisulfate, nitrate, acetate, oxalate, besylate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," *J Pharm Sci,* 66:1–19 (1977).

Examples of pharmaceutically acceptable, non-toxic esters of a compound of the present invention, if applicable, include $C_1$–$C_8$ alkyl esters. Acceptable esters also include $C_5$–$C_7$ cycloalkyl esters, as well as arylalkyl esters such as benzyl. $C_1$–$C_4$ alkyl esters are preferred. Esters of a compound of the present invention may be prepared according to methods that are well known in the art.

Examples of pharmaceutically acceptable non-toxic amides of a compound of the present invention include amides derived from ammonia, primary $C_1$–$C_8$ alkyl amines, and secondary $C_1$–$C_8$ dialkyl amines. In the case of secondary amines, the amine may also be in the form of a 5 or 6 membered heterocycloalkyl group containing at least one nitrogen atom. Amides derived from ammonia, $C_1$–$C_3$ primary alkyl amines, and $C_1$–$C_2$ dialkyl secondary amines are preferred. Amides of a compound of the present invention may be prepared according to methods well known to those skilled in the art.

The term "prodrug" means a compound that is transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A. C. S. *Symposium Series,* and in *Bioreversible Carriers in Drug Design,* ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as ($C_1$–$C_8$) alkyl, ($C_2$-$C_{12}$)alkanoyloxymethyl, 1-(alkanoyloxy)ethyl having from 4 to 9 carbon atoms, 1-methyl-1-(alkanoyloxy)- ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-($C_1$–$C_2$)alkylamino($C_2$–$C_3$)alkyl (such as β-dimethylaminoethyl), carbamoyl-($C_1$–$C_2$)alkyl, N,N-di($C_1$–$C_2$)alkylcarbamoyl-($C_1$–$C_2$)alkyl and piperidino-, pyrrolidino- or morpholino($C_2$–$C_3$)alkyl.

Similarly, if a compound of the present invention comprises an alcohol functional group, a prodrug can be formed by the replacement of the hydrogen atom of the alcohol group with a group such as ($C_1$–$C_6$)alkanoyloxymethyl, 1-(($C_1$-$C_6$)alkanoyloxy)ethyl, 1-methyl-1-(($C_1$–$C_6$) alkanoyloxy)ethyl, ($C_1$-$C_6$)alkoxycarbonyloxymethyl, N-($C_1$–$C_6$)alkoxycarbonylaminomethyl, succinoyl, ($C_1$-$C_6$) alkanoyl, α-amino($C_1$–$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O ($C_1$–$C_6$)alkyl)$_2$ or glycosyl (the radical resulting from the removal of a hydroxyl group of the hemiacetal form of a carbohydrate).

If a compound of the present invention comprises an amine functional group, a prodrug can be formed by the replacement of a hydrogen atom in the amine group with a group such as R-carbonyl, RO-carbonyl, NRR'-carbonyl where R and R' are each independently (($C_1$–$C_{10}$)alkyl, ($C_3$–$C_7$)cycloalkyl, benzyl, or R-carbonyl is a natural α-aminoacyl or natural α-aminoacyl-natural α-aminoacyl, —C(OH)C(O)OY wherein (Y is H, ($C_1$–$C_6$)alkyl or benzyl), —C(OY$_0$)Y$_1$ wherein Y$_0$ is ($C_1$–$C_4$) alkyl and Y$_1$ is (($C_1$-$C_6$)alkyl, carboxy($C_1$–$C_6$)alkyl, amino($C_1$–$C_4$)alkyl or mono-N- or di-N,N-($C_1$-$C_6$)alkylaminoalkyl, —C(Y$_2$)Y$_3$ wherein Y$_2$ is H or methyl and Y$_3$ is mono-N- or di-N,N-($C_1$-$C_6$)alkylamino, morpholino, piperidin-1-yl or pyrrolidin-1-yl.

A compound of the present invention may contain asymmetric or chiral centers, and therefore, exist in different stereoisomeric forms. It is contemplated that all stereoisomeric forms of a compound as well as mixtures thereof, including racemic mixtures, form part of the present invention. In addition, the present invention contemplates all geometric and positional isomers. For example, if a compound contains a double bond, both the cis and trans forms, as well as mixtures, are contemplated.

Diasteromeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, some of the compounds of this invention may be atropisomers (e.g., substituted biaryls) and are considered as part of this invention.

A compound of the present invention may exist in unsolvated as well as solvated forms with pharmaceutically acceptable solvents such as water, ethanol, and the like. The present invention contemplates and encompasses both the solvated and unsolvated forms.

It is also possible that a compound of the present invention may exits in different tautomeric forms. All tautomers of a compound of the present invention are contemplated. For example, all of the tautomeric forms of the imidazole moiety are included in this invention. Also, for example, all keto-enol or imine-enamine forms of the compounds are included in this invention.

Those skilled in the art will recognize that the compound names contained herein may be based on a particular tautomer of a compound. While the name for only a particular tautomer may be used, it is intended that all tautomers are encompassed by the name of the particular tautomer and all tautomers are considered part of the present invention.

It is also intended that the invention disclosed herein encompass compounds that are synthesized in vitro using laboratory techniques, such as those well known to synthetic chemists; or synthesized using in vivo techniques, such as through metabolism, fermentation, digestion, and the like. It is also contemplated that a compound of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature.

Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}O$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in compound and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, may afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples below, by substituting a readily available isotopically labelled reagent for a non-isotopically labelled reagent.

The compounds of the present invention can be generally prepared as follows:

Preparation of the 3'-substituted or unsubstituted tetrazoles 1-3 is illustrated in Scheme 1. The intermediate 1 for preparation of the tetrazoles of the present invention can be synthesized by coupling a 4-cyanophenol 1b with a bis-aryl iodonium tetrafluoroborate 1c at room temperature in an organic solvent such as dichloromethane, in the presence of a copper catalyst such as copper bronze and a base such as triethylamine (TEA). The 4-cyanophenol 1b is prepared by reacting a 4-bromophenol 1a, which are known in the art, with copper cyanide in dimethylformamide (DMF) at reflux temperature. Preparation of the bis-aryl iodonium tetrafluoroborate 1c can be carried out from a known anisole according to the procedure described in the *J. Med. Chem,* 38, 695–707, (1995). The tetrazole 1–2 is prepared by reacting the cyano compound 1 with sodium azide and ammonium chloride in DMF at reflux temperature followed by HCl work up. The tetrazole 1-2 is demethylated using a suitable boron trihalide such as boron trichloride or boron tribromide, in an organic solvent such as chloroform, to afford the hydroxy tetrazole 1-3.

The 3'-sulfonamides are prepared as shown in Scheme 2. Treatment of the compound 1 with neat chlorosulfonic acid at about 0° C. to about room temperature gives the 3'-chlorosulfonylated compound 2-1. The compound 2-1 is reacted with a primary amine in a solvent such as dichloromethane, tetrahydrofuran (THF), methanol (MeOH), ethanol (EtOH) or acetonitrile, in the presence of a base such as TEA or diisopropylethylamine, to afford the compound 2-2. Likewise, the compound 2-3 can be prepared by reacting 2-1 with a secondary amine under similar conditions. Alternatively, the compound 2-3 may be prepared by alkylation of the compound 2-2. A preferred alkylation method uses a suitable alkylating agent such as an alkyl halide, in the presence of a base such as sodium hydride, in an organic solvent such as THF. The compound 2-2 is demethylated using boron tribromide in chloroform. The demethylated compound is then converted to the tetrazole 2-4 by reacting with sodium azide and ammonium chloride in DMF at elevated temperature. Likewise, the tetrazole 2-5 can be prepared from the compound 2-3 via demethylation and tetrazole formation under similar conditions.

Formation of the 3'-carboxamides is carried out as described in Scheme 3. Treatment of 1 with hexamethylenetetramine at 65° C. in trifluoroacetic acid (TFA) gives the 3'-aldehyde 3-1. Oxidation of 3-1 provides the carboxylic acid 3-2. Preferred oxidation methods include Jones oxidation (chromic acid/aqueous sulfuric acid) and those employing sodium hypochlorite (buffered aqueous NaClO, and 2-methyl-2-butene in t-butanol/THF). The carboxylic acid 3-2 can be converted to the carboxamide 3-3 or 3-4 according to methods analogous to those known in the art. For example, employment of an acid chloride activated ester, or mixed anhydride of 3-2 with a primary or secondary amine in a dried aprotic solvent such as dichloromethane, THF, dimethylether (DME) or diethylether (DEE), in the presence of a base such as TEA, dimethylaminopyridine or pyridine. Also, the carboxylic acid 3-2 can be reacted with N-hydroxysuccinimide, dicyclohexylcarbodimmide, and an amine in the presence of a base such as TEA in 1,2-dimethoxyethane. Alternatively, the compound 3-3 can be converted to the compound 3-4 by alkylation. A preferred alkylation method uses an alkylating agent such as an alkyl halide, in the presence of a base such as sodium hydride, in an organic solvent such as THF. The compound 3-3 is converted to the tetrazole 3-5 via demethylation and tetrazole formation by procedures analogous to those described in Scheme 2. Likewise, the compound 3-6 is prepared from the compound 3-4 via demethylation and tetrazole formation. It is noted that the tetrazole can be formed first followed by demethylation.

The aminotetrazoles 4-4 are prepared as shown in Scheme 4. The intermediate 4 can be synthesized according to methods analogous to those known in the art. For example, by coupling 4-nitrophenol with bis-aryl iodonium tetrafluoroborate at room temperature in the presence of a copper catalyst and TEA in dichloromethane (*J. Med. Chem,* 38, 695–707, (1995). An alternative method for preparing 4 is by coupling a 4-halonitrobenzene such as 4-iodonitrobenzene, 4-bromonitrobenzene or 4-chloronitrobenzene with an appropriate 4-methoxyphenol at 120° C. in the presence of a suitable base such as potassium carbonate or potassium t-butoxide, in a polar solvent such as dimethylsulfoxide (DMSO) or N-methylpyrrolidone. A third method for preparing 4 is by coupling a 4-methoxyphenylboronic acid with a 4-nitrophenol in the presence of copper (II) acetate and a base such as TEA, pyridine or a mixture of TEA and pyridine according to the procedure described in *Tetrahedron Lett.,* 39, 2933–2936, 2937–2940, (1998). Hydrogenation of 4 in the presence of 10% Pd/C gives the aniline 4-1. The aniline 4-1 is reacted with cyanogen bromide in the presence of sodium acetate in a mixture of acetic acid and water to give the cyanamide 4-2. Treatment of the cyanamide 4-2 with sodium azide in the presence of ammonium chloride in DMF at elevated temperature gives the aminotetrazole 4-3. Demethylation of 4-3 with boron tribromide affords the hydroxy tetrazole 4-4.

Preparation of aminotetrazoles containing 3'-sulfonamides is illustrated in Scheme 5. The compound 5 is reacted with neat chlorosulfonic acid at 0° C. to room temperature to give the 3'-chlorosulfonylated compound 5-1. The compound 5-1 is reacted with a primary amine in a solvent such as dichloromethane, THF or acetonitrile, in the presence of a base such as TEA or diisopropylethylamine, to afford the secondary sufonamide 5-2. Alternatively, the compound 5-1 can be converted to the tertiary sulfonamide 5-3 using a secondary amine under similar conditions. In addition, the compound 5-3 may be prepared by alkylation of the compound 5-2. A preferred alkylation method uses an alkylating agent such as an alkyl halide, in the presence of a base such as sodium hydride, in an organic solvent such as THF. The compound 5-2 is converted to the cyanamide 5-4 via demethylation, hydrogenation and cyanamide formation by procedures analogous to those described in and Scheme 4. The cyanamide 5-4 is reacted with sodium azide and ammonium chloride in DMF to give the aminotetrazole 5-6. Similarly, the compound 5-7 is prepared from the compound 5-3 via demethylation, hydrogenation, cyanamide formation and then tetrazole formation.

Preparation of aminotetrazoles containing 3'-carboxamides can be carried out as outlined in Scheme 6. The compound 5 can be converted to the aldehyde 6-1 according to methods known in the art. For example, the compound 5 can be reacted with hexamethylenetetramine at 65° C. in TFA to give the 3'-aldehyde 6-1. Oxidation of 6-1 provides the carboxylic acid 6-2. Preferred oxidation methods include Jones oxidation (chromic acid/aqueous sulfuric acid) and methods employing sodium hypochlorite (buffered aqueous NaClO, and 2-methyl-2-butene in t-butanol/THF). The carboxylic acid 6-2 can be converted to the carboxamide 6-3 or 6-4 according to methods analogous to those known in the art. For example, employment of an acid chloride, activated ester, or mixed anhydride of 6-2 with a primary or secondary amine in a dried aprotic solvent such as dichloromethane, THF, DME, in the presence of a base such as TEA, dimethylaminopyridine or pyridine can be used to make a carboxamide. Also, the carboxylic acid 6-2 can be reacted with N-hydroxysuccinimide, dicyclohexylcarbodiimide, and an amine in the presence of a base such as TEA in 1,2-dimethoxyethane. Alternatively, the compound 6-3 can be converted to the compound 6-4 by alkylation. A preferred alkylation method uses a suitable alkylating agent such as an alkyl halide, in the presence of a base such as sodium hydride, in an organic solvent such as THF. The compound 6-3 is converted to the aminotetrazole 6-5 via demethylation, hydrogenation, cyanamide formation and tetrazole formation by standard procedures analogous to those described in Scheme 4. Likewise, the compound 6-6 can be prepared from the compound 6-4 via demethylation, hydrogenation, cyanamide formation and tetrazole formation.

Preparation of the alkylsulfones 7-3 is illustrated in Scheme 7. The compound 5 is reacted with chlorosulfonic acid followed by reduction with sodium sulfite in $H_2O$ in the presence of a base such as sodium bicarbonate, or NaOH to afford the sulfinic acid 7-1. Alkylation of the sulfinic acid 7-1 with alkyl halide in the presence of a base such as sodium bicarbonate, NaOH, sodium hydride, sodium methoxide, and potassium t-butoxide gives the alkyl sulfone 7-2. The compound 7-2 can be converted to the aminotetrazole 7-3 via demethylation, hydrogenation, cyanamide formation and tetrazole formation.

Preparation of the 3'-aryl sulfones is outlined in Scheme 8. Treatment of 5 with arylsulfonic acid in the presence of a dehydrating agent, preferably $P_2O_5$ in methanesulfonic acid [Eaton's reagent] or polyphosphoric acid at elevated temperature gives the sulfone 8-1. The compound 8-1 can be converted to the aminotetrazole 8-2 via demethylation, hydrogenation, cyanamide formation and tetrazole formation.

The benzyltetrazoles 9-6 are prepared as shown in Scheme 9. The diaryl ether 9-2 is obtained by coupling of bis-aryl iodonium tetrafluoroborate 1c with the phenol 9-1 in the presence of copper bronze and triethyl amine in dichloromethane. Reduction of 9-2 with diisobutylaluminum hydride (DIBAL) in dichloromethane affords the benzyl alcohol 9-3. Treatment of 9-3 with dibromotriphenylphosphorane in acetonitrile gives the benzyl bromide 9-4. Reaction of the bromide 9-4 with copper cyanide in DMF at 140° C. yields the benzyl cyanide 9-5. The benzyltetrazole 9-6 can be obtained from 9-5 via demethylation and tetrazole formation.

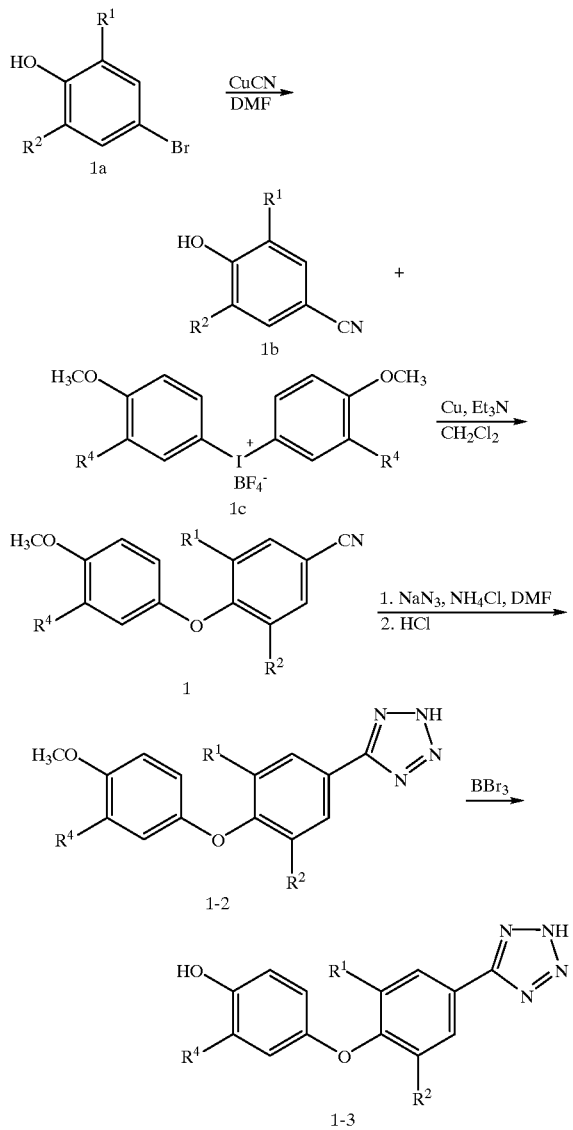

Scheme 1

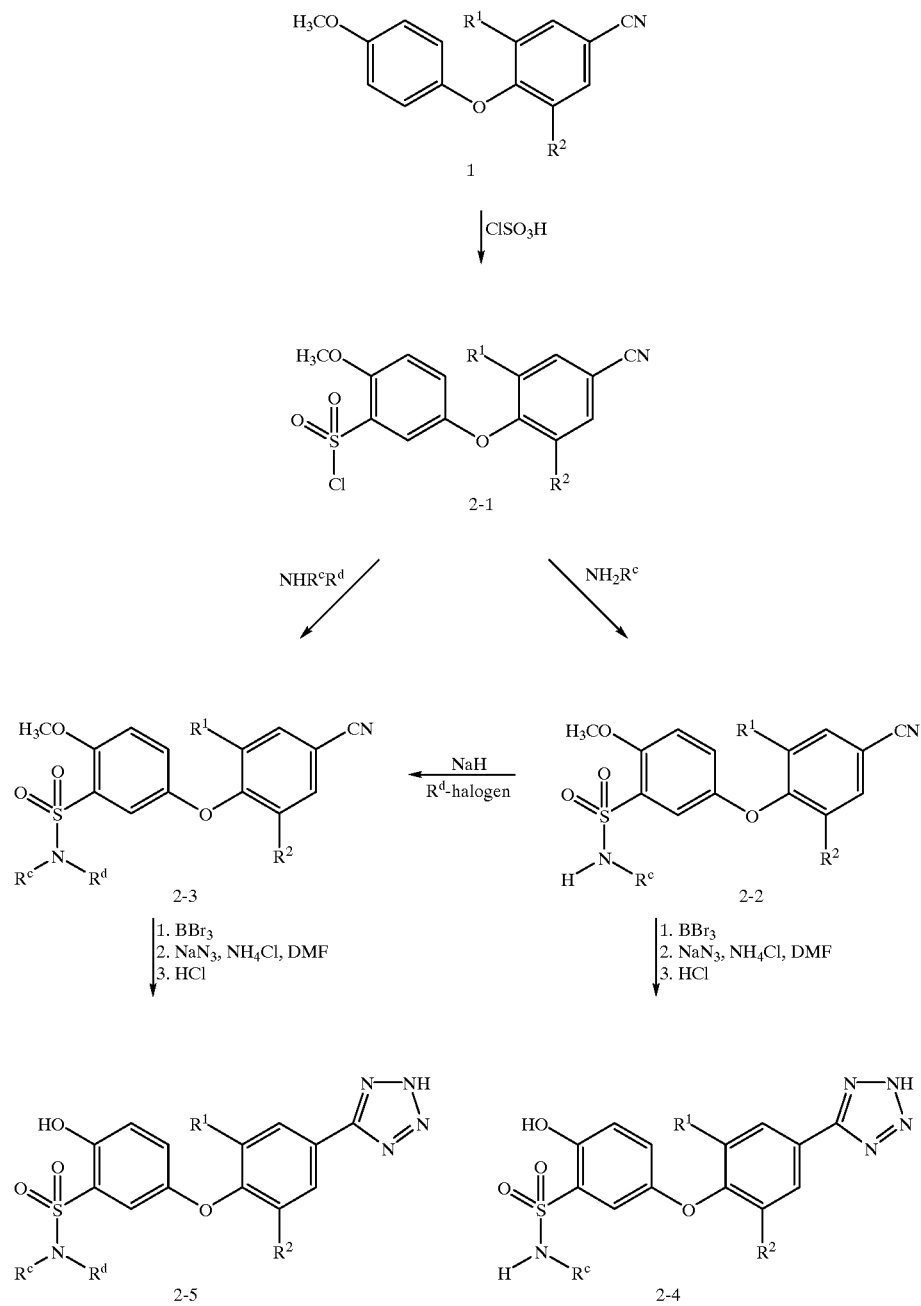

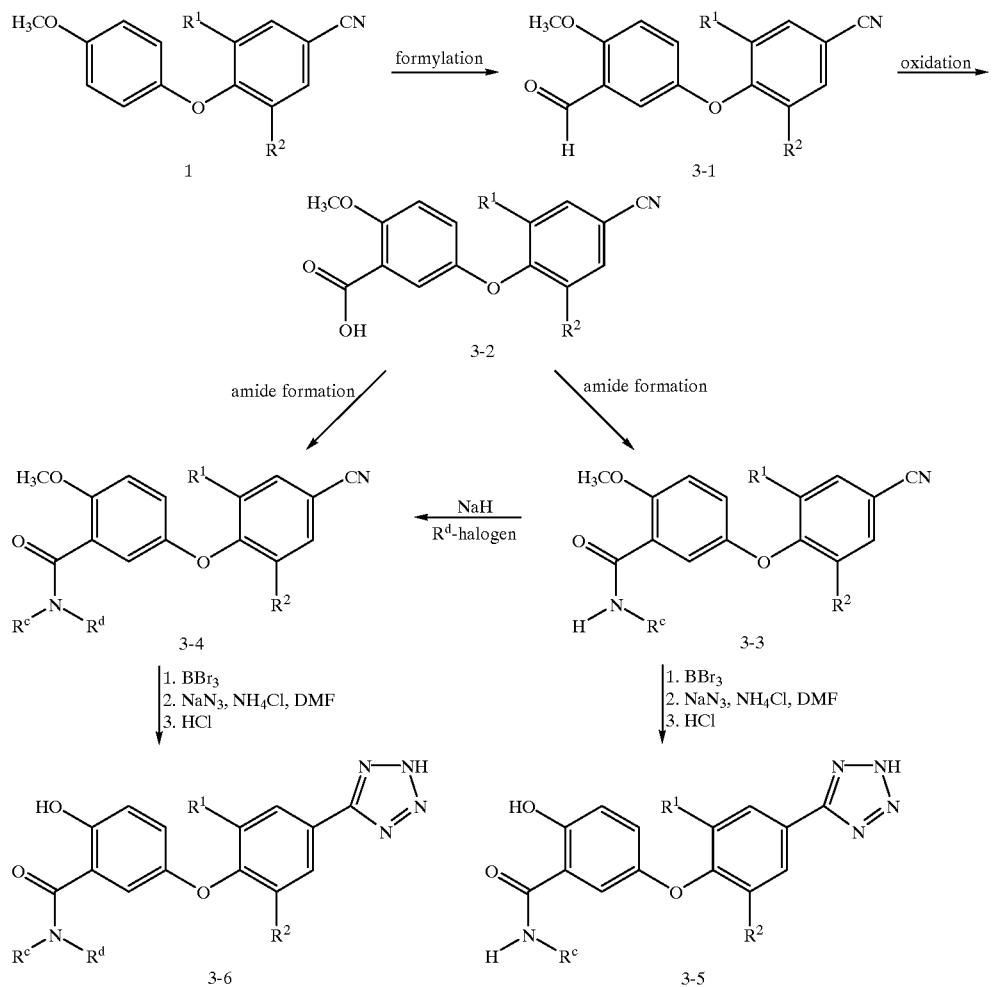
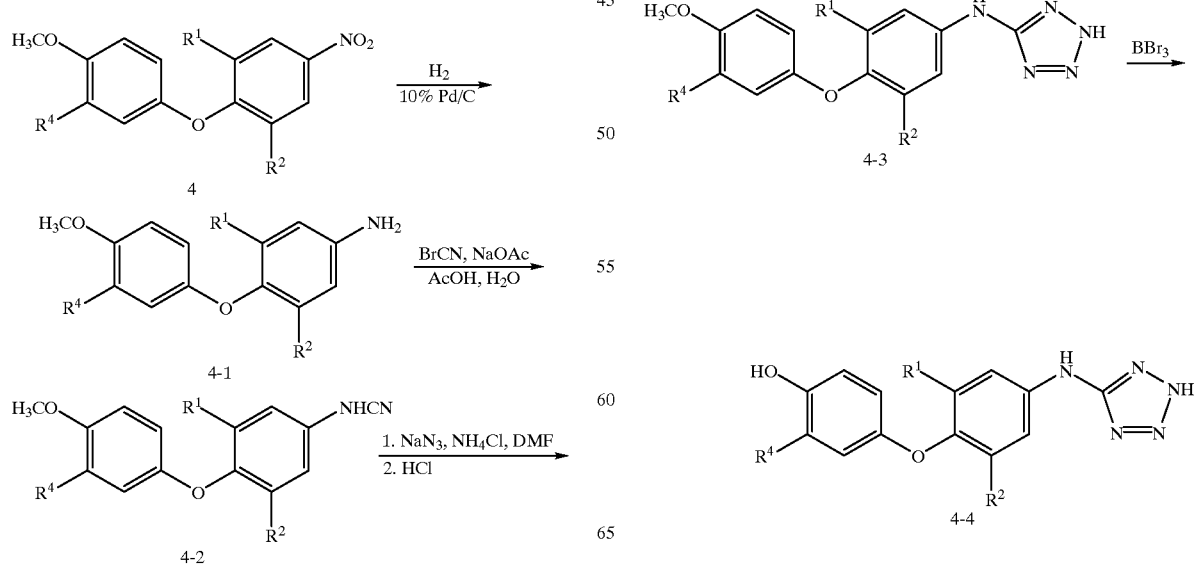

Scheme 5
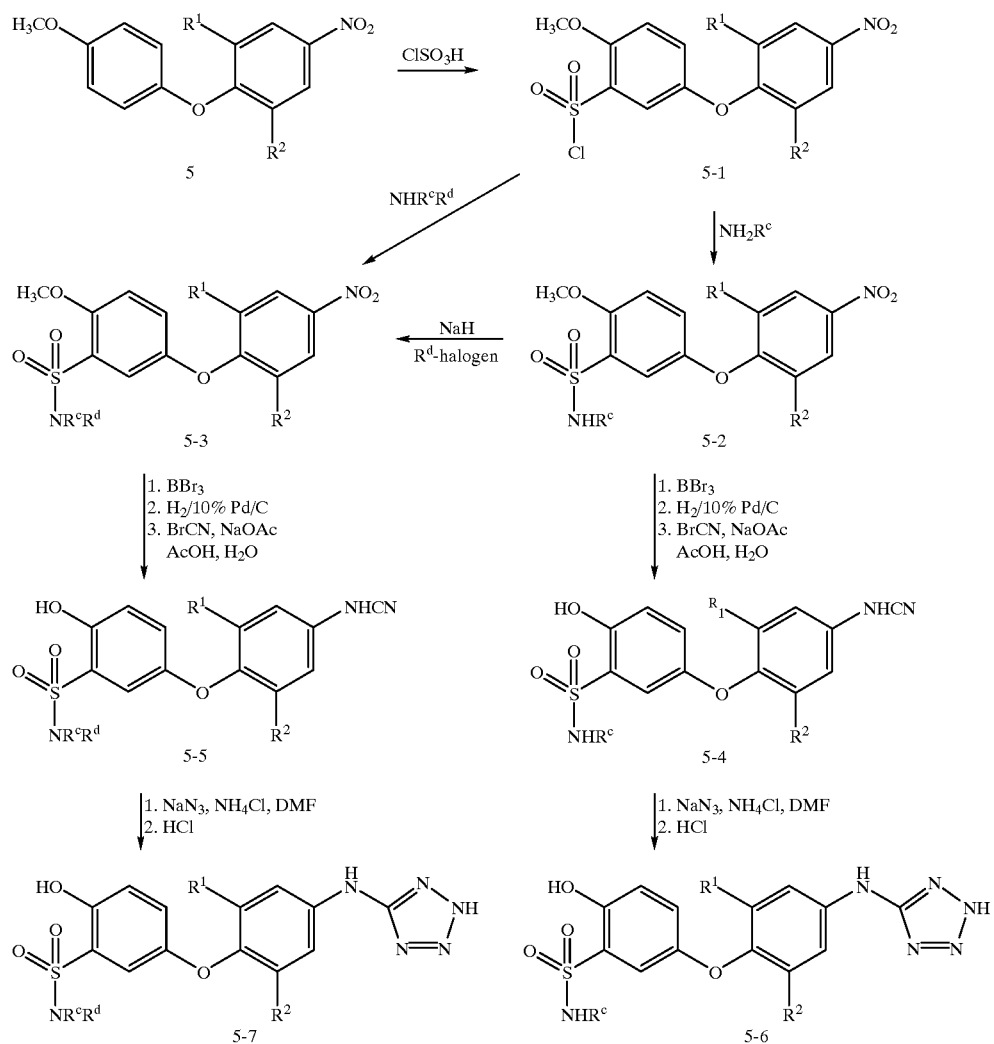
Scheme 6
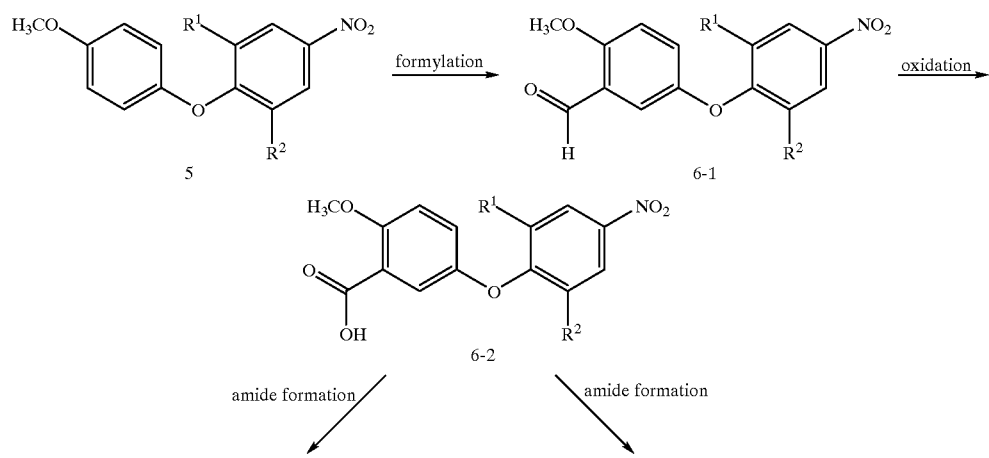

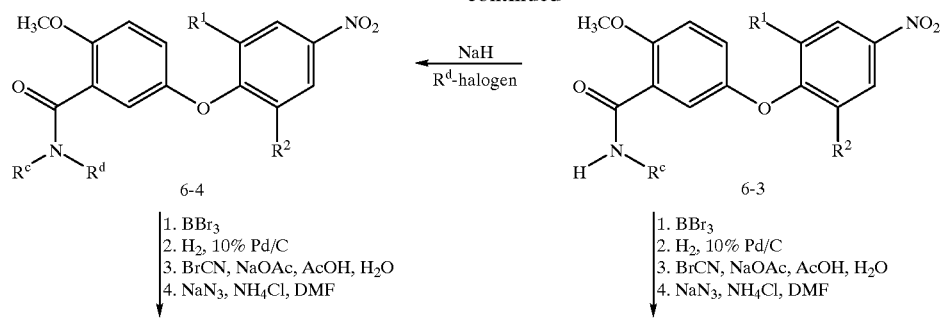
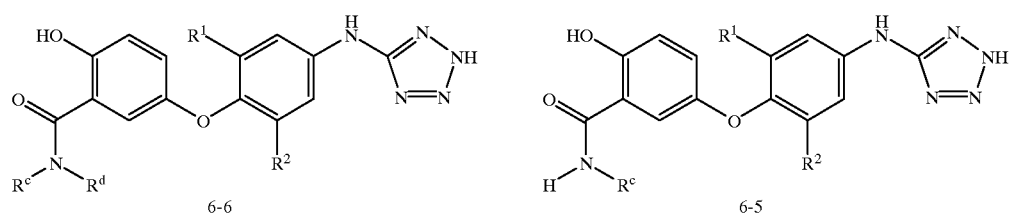
Scheme 7
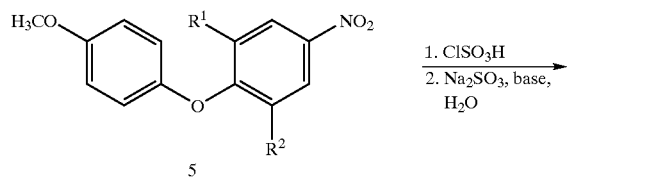
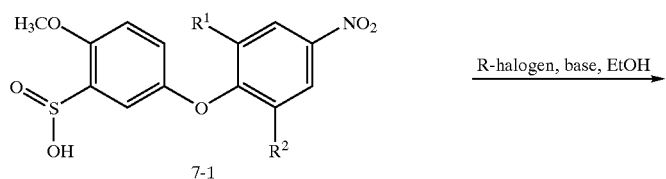
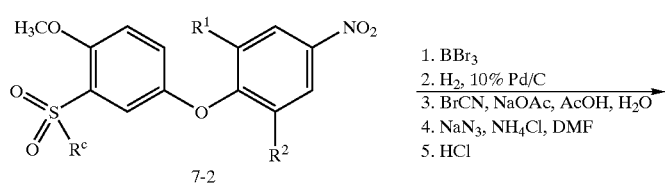
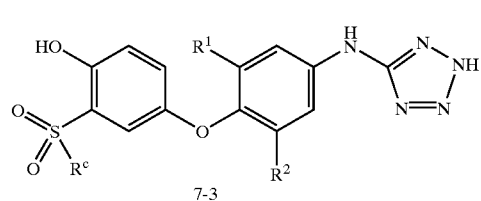

Scheme 8

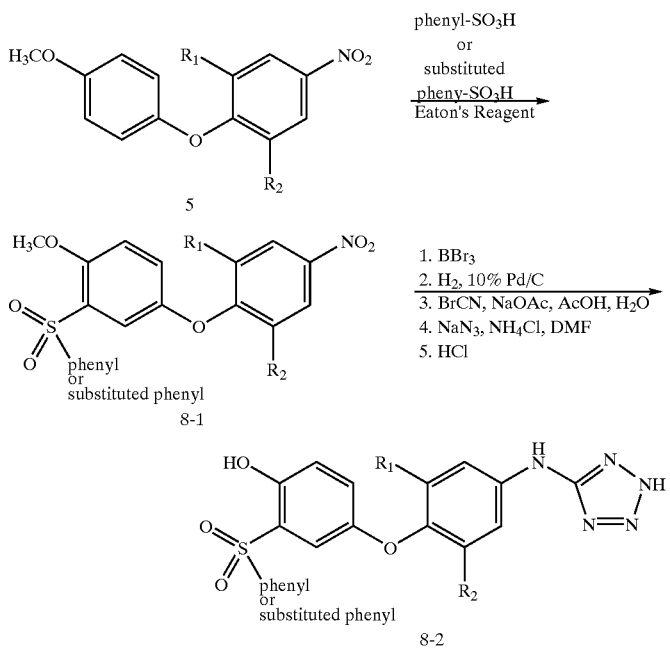

Scheme 9

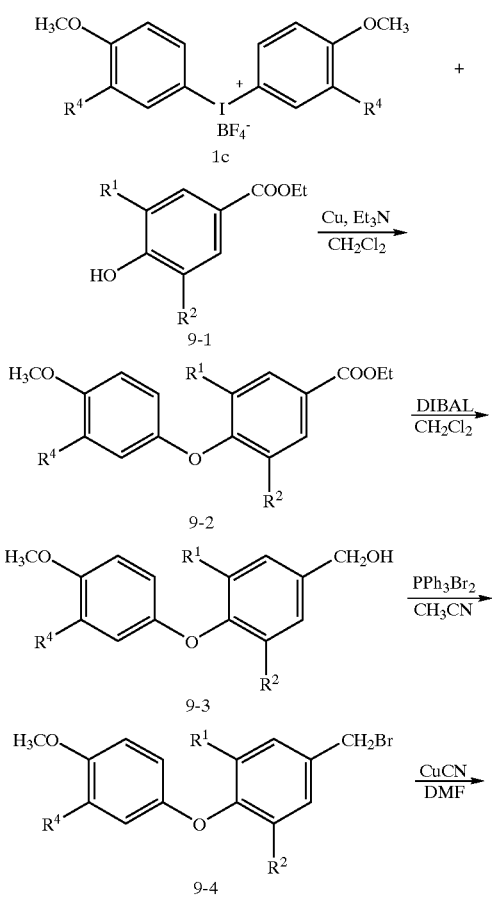

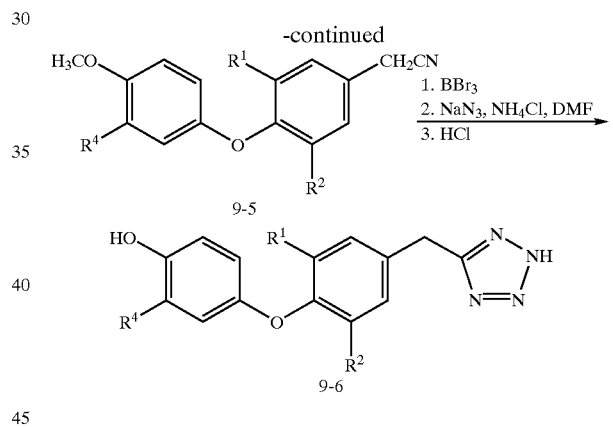

EXAMPLES

The examples presented below are intended to illustrate particular embodiments of the invention and are not intended to limit the scope of the specification, including the claims, in any manner.

The following abbreviations or acronyms may be used in this application

| | |
|---|---|
| RT | room temperature |
| NMR | nuclear magnetic resonance |
| TLC | thin layer chromatography |
| MS | mass spectrometry |
| APCI– | atmospheric pressure chemical ionization, negative ion mode |
| Calc | Calculated |
| Equiv | equivalent(s) |
| MeOH | methanol |
| APCI+ | atmospheric pressure chemical ionization, positive ion mode |
| THF | tetrahydrofuran |
| EtOAc | ethyl acetate |

| | |
|---|---|
| Et | ethyl |
| Me | methyl |

Example 1

4-[2,6-Dimethyl-4-(2H-tetrazol-5-yl)-phenoxy]-2-isopropyl-phenol

Step A—Preparation of 4-hydroxy-3,5-dimethyl-benzonitrile

To a solution of 4-bromo-2,6-dimethyl-phenol (1.0 g, 5.0 mmol) (Aldrich Chemical Co., Milwaukee, Wis.) in 8 ml of N,N-dimethylformamide at room temperature (RT) was added copper (I) cyanide (0.67 g, 7.5 mmol), and the reaction mixture was refluxed for 7 hours. The mixture was then cooled to RT and filtered. The filtrate was poured into 50 ml of water and extracted with ethyl acetate (3×50 ml). The combined organic layers were washed with water (3×50 ml), dried, and concentrated. The residue was purified by preparative TLC (dichloromethane) to afford the title product of Step A. NMR (400 MHz, $CDCl_3$) δ 7.28 (s, 2H), 5.26 (br s, 1H), 2.27 (s, 6H).

Step B—Preparation of 4-(3-Isopropyl-4-methoxy-phenoxy)-3,5-dimethyl-benzonitrile To a solution of bis-(3-isopropyl-4-methoxy-phenyl)-iodonium tetrafluoroborate (3.03 g, 5.9 mmol) and copper bronze (0.5 g, 7.9 mmol) in 8 ml of dichloromethane cooled to 0° C. was added dropwise a solution of 4-hydroxy-3,5-dimethyl-benzonitrile (0.58 g, 3.9 mmol) and triethylamine (0.61 ml, 4.4 mmol) in 6 ml of dichloromethane. The reaction mixture was stirred for 6 days at RT, then filtered through Celite® and concentrated. The residue was purified by preparative TLC (hexanes:dichloromethane 1:4) to afford the title product of Step B. NMR (400 MHz, $CDCl_3$) δ 7.40 (s, 2H), 6.74 (d, 1H), 6.67 (d, 1H), 6.21 (dd, 1H), 3.77 (s, 3H), 3.27 (p, 1H), 2.15 (s, 6H), 1.17 (d, 3H).

Step C—Preparation of 5-[4-(3-Isopropyl-4-methoxy-phenoxy)-3,5-dimethyl-phenyl]-2H-tetrazole To a solution of 4-(3-isopropyl-4-methoxy-phenoxy)-3,5-dimethyl-benzonitrile (37 mg, 0.13 mmol ) in 0.5 ml of N,N-dimethylformamide at RT was added sodium azide (9.0 mg, 0.14 mmol) and ammonium chloride (7.4 mg, 0.14 mmol). The mixture was refluxed for 20 hours, then poured into ice/water and acidified with 2N HCl to pH 2. The white solid was collected by filtration and dried in vacuo. The title product of Step C was used in the next step without purification. MS (APCI⁻) Calc.: 338.4, Found: 337.3 (M−1).

Step D—Preparation of 4-[2,6-Dimethyl-4-(2H-tetrazol-5-yl)-phenoxy]-2-isopropyl-phenol To a solution of 5-[4-(3-isopropyl-4-methoxy-phenoxy)-3,5-dimethyl-phenyl]-2H-tetrazole (26 mg, 0.077 mmol) in 6 ml of chloroform at RT was added boron tribromide (1M in dichloromethane, 0.12 ml, 0.12 mmol). The reaction was stirred for 20 hours at RT, then additional boron tribromide (1M in dichloromethane, 0.3 ml) was added, and the reaction was stirred at RT for 6 hours. Water (10 ml) was added, and the reaction was stirred for 1 hour at RT, then extracted with ethyl acetate (3×15 ml), dried, and concentrated. The white solid residue was triturated with dichloromethane (2×0.3 ml) and dried in vacuo to afford the title product of Example 1. MS (APCI⁻) Calc.: 324.4, Found: 323.3 (M−1).

EXAMPLE 1-1 was prepared in an analogous manner to the sequence of reactions described for EXAMPLE 1 with the noted changes.

Example 1-1

4-[2,6-Dichloro-4-(1H-tetrazol-5-yl)-phenoxy]-2-isopropyl-phenol

MS (APCI⁻) Calc.: 364.0, Found: 363.2 (M−1).

3,5-dichloro-4-hydroyxbenzonitrile was used in place of 4-hydroxy-3,5-dimethylbenzonitrile in Step B.

Example 2

4-[2,6-Dichloro-4-(2H-tetrazol-5-yl)-phenoxy]-2-(pyrrolidine-1-sulfonyl)-phenol

Step A—Preparation of 3,5-Dichloro-4-[4-methoxy-3-(pyrrolidine-1-sulfonyl)-phenoxy]-benzonitrile To 3,5-dichloro-4-(4-methoxy-phenoxy)-benzonitrile (70 mg, 0.238 mmol) was added chlorosulfonic acid (0.6 ml, 9.0 mmol) dropwise at RT. The resulting solution was stirred for 1 hour at RT, then added dropwise to ice. The mixture was extracted with dichloromethane (3×10 ml), and the combined organic phases were dried and concentrated. The residue was dissolved in dichloromethane (2 ml) and pyrrolidine (40 μl, 0.48 mmol) and triethylamine (80 μl, 0.57 mmol) were added. The solution was stirred at RT for 1 hour, then concentrated. The residue was purified by preparative TLC (ethyl acetate:hexanes 1:1) to afford the title product of Step A. MS (APCI+) Calc.: 426.0, Found: 427.0 (M+1).

Step B—Preparation of 3,5-Dichloro-4-[4-hydroxy-3-(pyrrolidine-1-sulfonyl)-phenoxy]-benzonitrile To a solution of 3,5-dichloro-4-[4-methoxy-3-(pyrrolidine-1-sulfonyl)-phenoxy]-benzonitrile (30 mg, 0.070 mmol) in 2 ml of dichloromethane at RT was added boron tribromide (1M in dichloromethane, 0.386 ml, 0.39 mmol). The reaction mixture was stirred for 1 hour at RT. Water (10 ml) was added, and the reaction was stirred for 20 minutes at RT, then extracted with ethyl acetate (2×10 ml) and dichloromethane (1×10 ml). The combined organic phases were dried, and concentrated. The title product of Step B was used in the next step without purification. MS (APCI+) Calc.: 412.0, Found: 413.1 (M+1).

Step C—Preparation of 4-[2,6-Dichloro-4-(2H-tetrazol-5-yl)-phenoxy]-2-(pyrrolidine-1-sulfonyl)-phenol 4-[2,6-Dichloro-4-(2H-tetrazol-5-yl)-phenoxy]-2-(pyrrolidine-1-sulfonyl)-phenol was prepared from 3,5-dichloro-4-[4-hydroxy-3-(pyrrolidine-1-sulfonyl)-phenoxy]-benzonitrile according to a procedure analogous to that described in EXAMPLE 1, Step C. Sodium azide (4.0 equiv) and ammonium chloride (4.0 equiv) were used, and the reaction was heated to 143° C. for 40 hours. After the reaction had been acidified and the crude product collected by filtration, the solid was dissolved in MeOH, filtered, and the filtrate was concentrated. The residue was purified by preparative TLC (methanol:water:chloroform=19:1:47) to afford the title product of Example 2. MS (APCI⁻) Calc.: 455.0, Found: 454.2 (M−1).

EXAMPLES 2-1 to 2-4 were prepared in an analogous manner to the sequence of reactions described for EXAMPLE 2 with the noted changes.

Example 2-1

4-[2,6-Dichloro-4-(2H-tetrazol-5-yl)-phenoxy]-2-(piperidine-1-sulfonyl)-phenol

MS (APCI⁻) Calc.: 469.1 Found: 468.1 (M−1).

Piperidine (2.0 equiv) was substituted for pyrrolidine in Step A.

Example 2-2

4-[2,6-Dichloro-4-(2H-tetrazol-5-yl)-phenoxy]-2-(3,3-dimethyl-piperidine-1-sulfonyl)-phenol MS (APCI⁻) Calc.: 497.1, Found: 496.2 (M−1).

3,3-Dimethylpiperidine (2.0 equiv) was substitued for pyrrolidine in Step A.

Example 2-3

N-Cyclopropyl-5-[2,6-dichloro-4-(2H-tetrazol-5-yl)-phenoxy]-2-hydroxy-benzenesulfonamide MS (APCI⁻) Calc.: 441.0 Found: 440.0 (M−1).

Cyclopropylamine (1.5 equiv) was substituted for pyrrolidine in Step A.

Example 2-4

5-[2,6-Dichloro-4-(2H-tetrazol-5-yl)-phenoxy]-2-hydroxy-N,N-dimethyl-benzenesulfonamide MS (APCI⁻) Calc.: 429.0 Found: 428.1 (M−1).

Dimethylamine (2.0M in THF [3.5 equiv]) was substituted for pyrrolidine in Step A.

Example 3

{5-[2,6-Dichloro-4-(1H-tetrazol-5-yl)-phenoxy]-2-hydroxy-phenyl}-piperidin-1-yl-methanone Step A—Preparation of 3,5-Dichloro-4-(3-formyl-4-methoxy-phenoxy)-benzonitrile A solution of 3,5-dichloro-4-(4-methoxy-phenoxy)-benzonitrile (500 mg, 1.7 mmol) and hexamethylenetetramine (357 mg, 2.5 mmol) in trifluoroacetic acid (5 ml) was stirred for 4 hours at 75° C. The mixture was cooled to RT, and the excess trifluoroacetic acid was removed in vacuo. The oily residue was diluted with 10 ml water, and the resulting suspension was stirred for 1 hour, then neutralized with saturated aqueous NaHCO₃. The mixture was then extracted with ethyl acetate (2×20 ml), and the combined organic phases were washed with saturated aqueous NaHCO₃ (1×25 ml), brine (1×25 ml), dried over anhydrous Na₂SO₄, filtered, and concentrated in vacuo to give a brown foam. The residue was triturated in ethyl ether with a minimal amount of dichloromethane to produce a precipitate, which was removed by filtration and washed with ether. The filtrate (with the ether washings) was concentrated to give the desired title product of Step A, which was used in the next step without purification. MS (APCI+) Calc.: 320.9, Found: 322.1 (M+1).

Step B—Preparation of 5-(2,6-Dichloro-4-cyano-phenoxy)-2-methoxy-benzoic acid

To a solution of 3,5-dichloro-4-(4-methoxy-phenoxy)-benzonitrile (100 mg, 0.31 mmol) in acetone (1.5 ml) at RT was added Jones reagent (30 drops) with stirring until a red color persisted. The solution was stirred 1 hour, then quenched with isopropanol (1 ml). The reaction was filtered through Celite®, and the filtrate was basified with an aqueous solution of 1N NaOH and the organic solvent was removed in vacuo. The aqueous mixture was washed with diethyl ether (2×15 ml), and the combined organic phases were then back-extracted with 1N NaOH (1×15 ml). All of the aqueous layers were combined and acidified with concentrated HCl to give a turbid solution. This aqueous mixture was extracted with ethyl acetate (3×20 ml), and the combined organic phases were dried over anhydrous Na₂SO₄, filtered, and concentrated. The title product of Step B was used in the next step without purification. MS (APCI⁻) Calc.: 337.2, Found: 336.1 (M−1).

Step C—Preparation of 3,5-Dichloro-4-[4-methoxy-3-(piperidine-1-carbonyl)-phenoxy]-benzonitrile A solution of 3,5-dichloro-4-(3-formyl-4-methoxy-phenoxy)-benzonitrile (85 mg, 0.25 mmol) and thionyl chloride (92 µl, 1.26 mmol) in tetrahydrofuran (2.5 ml) was refluxed for 1 hour. THF and excess thionyl chloride was then removed under reduced pressure, and the residue was dissolved in dichloromethane (2.5 ml) and piperidine (30 µl, 0.30 mmol) and N,N-diisopropylethylamine (88 µl, 0.50 mmol) were added. The solution was stirred at RT for 1 hour, then concentrated. The product was purified by preparative TLC (diethyl ether:dichloromethane 1:9) to afford the title product of Step C. MS (APCI+) Calc.: 404.0, Found: 405.1 (M+1).

Step D—Preparation of 3,5-Dichloro-4-[4-hydroxy-3-(piperidine-1-carbonyl)-phenoxy]-benzonitrile 3,5-Dichloro-4-[4-hydroxy-3-(piperidine-1-carbonyl)-phenoxy]-benzonitrile was prepared from 3,5-dichloro-4-[4-methoxy-3-(piperidine-1-carbonyl)-phenoxy]-benzonitrile according to a procedure analogous to that described in EXAMPLE 2, Step B. Boron tribromide (1M in dichloromethane, 2.0 equiv) was used. After water addition, the mixture was stirred for 30 minutes at RT, then basified with aqueous saturated sodium bicarbonate solution, and extracted with dichloromethane (3×10 ml). The combined organic phases were dried over anhydrous Na₂SO₄, filtered, and concentrated. The title product of Step E was used in the next step without purification.) MS (APCI+) Calc.: 390.0, Found: 391.1 (M+1).

Step E—Preparation of {5-[2,6-Dichloro-4-(1H-tetrazol-5-yl)-phenoxy]-2-hydroxy-phenyl}-piperidin-1-yl-methanone {5-[2,6-Dichloro-4-(1H-tetrazol-5-yl)-phenoxy]-2-hydroxy-phenyl}-piperidin-1-yl-methanone was prepared from 3,5-dichloro-4-[4-hydroxy-3-(piperidine-1-carbonyl)-phenoxy]-benzonitrile according to a procedure analogous to that described in EXAMPLE 1, Step C. Sodium azide (2.0 equiv) and ammonium chloride (2.0 equiv) were used initially, and the reaction mixture was heated to reflux for 2 hours, after which additional sodium azide (2.0 equiv) was added, and the reaction was heated to reflux for 20 hours. After the reaction had been acidified and the crude product collected by filtration, then purified by preparative TLC (methanol:water:dichloromethane 20:3:77) to afford the title product of Example 3. MS (APCI+) Calc.: 433.0, Found: 434.1 (M+1).

EXAMPLES 3-1 to 3-4 were prepared in an analogous manner to the sequence of reactions described for EXAMPLE 3 with the noted changes.

Example 3-1

N-Cyclobutyl-5-[2,6-dichloro-4-(1H-tetrazol-5-yl)-phenoxy]-2-hydroxy-benzamide

MS (APCI⁻) Calc.: 419.0, Found: 418.1 (M−1).

Cyclobutylamine (1.0 equiv) was substituted for piperidine in Step C.

Example 3-2

N-Cyclohexyl-5-[2,6-dichloro-4-(1H-tetrazol-5-yl)-phenoxy]-2-hydroxy-benzamide

MS (APCI⁻) Calc.: 447.0, Found: 446.2 (M−1).

Cyclohexylamine (1.0 equiv) was substituted for piperidine in Step C.

Example 3-3

{5-[2,6-Dichloro-4-(1H-tetrazol-5-yl)-phenoxy]-2-hydroxy-phenyl}-pyrrolidin-1-yl-methanone MS (APCI⁻) Calc.: 419.0, Found: 418.0 (M−1).

Pyrrolidine (1.0 equiv) was substituted for piperidine in Step C.

Example 3-4

N-Bicyclo[2.2.1]hept-2-yl-5-[2,6-dichloro-4-(1H-tetrazol-5-yl)-phenoxy]-2-hydroxy-benzamide MS (APCI⁻) Calc.: 459.0, Found: 458.1 (M−1).

Exo-2-aminonorbornane (1.0 equiv) was substituted for piperidine in Step C.

Example 4

4-[2,6-Dimethyl-4-(1H-tetrazol-5-ylamino)-phenoxy]-2-isopropyl-phenol

Step A—Preparation of 4-(3-isopropyl-4-methoxy-phenoxy)-3,5-dimethyl-phenylamine To 4-(3-isopropyl-4-methoxy-phenoxy)-3,5-dimethyl-nitrobenzene (3.2 g, 10.1 mmol) in a mixture of ethyl acetate (10 ml) and ethanol (50 ml) was added catalyst 10% Pd/C (0.32 g). The mixture was hydrogenated under 40 psi at RT for 16 hours. The mixture was filtered through Celite® and concentrated. The title product of Step A was obtained by recrystallization from dichloromethane/hexanes. MS (APCI+) Calc.: 285.4, Found: 286.2 (M+1).

Step B—Preparation of 4-(3-Isopropyl-4-methoxy-phenoxy)-3,5-dimethyl-phenyl-cyanamide To a solution of 4-(3-isopropyl-4-methoxy-phenoxy)-3,5-dimethyl-phenylamine (100 mg, 0.35 mmol), acetic acid (1 ml), and water (1 ml) cooled to 0° C. was added sodium acetate (43 mg, 0.53 mmol), and the mixture was stirred for 10 minutes until dissolved. Cyanogen bromide (45 mg, 0.42 mmol) was added, and the reaction mixture was allowed to slowly warm to RT and stirred for 18 hours. The mixture was then diluted with water (15 ml) and extracted with ethyl acetate (3×10 ml). The combined organic phases were washed with aqueous saturated sodium bicarbonate solution (3×20 ml), brine (20 ml), then dried over anhydrous Na₂SO₄, filtered, and concentrated. The residue was purified by preparative TLC (ethyl acetate:hexanes 2:3) to afford the title product of Step B. MS (APCI⁻) Calc.: 310.4, Found: 309.2 (M−1).

Step C—Preparation of [4-(3-Isopropyl-4-methoxy-phenoxy)-3,5-dimethyl-phenyl]-(1H-tetrazol-5-yl)-amine

[4-(3-Isopropyl-4-methoxy-phenoxy)-3,5-dimethyl-phenyl]-(1H-tetrazol-5-yl)-amine was prepared from 4-(3-isopropyl-4-methoxy-phenoxy)-3,5-dimethyl-phenyl-cyanamide according to a procedure analogous to that described in EXAMPLE 1, Step C. Sodium azide (1.2 equiv) and ammonium chloride (10.0 equiv) were used, and the reaction was heated to 165° C. for 5 hours. After the reaction had been acidified, the mixture was extracted with ethyl acetate (3×10 ml). The combined organic extracts were washed with 1N HCl (3×50 ml) and brine (1×50 ml). The organic phase was dried over anhydrous Na₂SO₄, filtered, and concentrated. The residue was purified by preparative TLC (methanol:water:dichloromethane 10:0.5:89.5) to afford the title product of Step C. MS (APCI+) Calc.: 353.4, Found: 354.1 (M+1).

Step D—Preparation of 4-[2,6-Dimethyl-4-(1H-tetrazol-5-ylamino)-phenoxy]-2-isopropyl-phenol 4-[2,6-Dimethyl-4-(1H-tetrazol-5-ylamino)-phenoxy]-2-isopropyl-phenol was prepared from [4-(3-isopropyl-4-methoxy-phenoxy)-3,5-dimethyl-phenyl]-(1H-tetrazol-5-yl)-amine according to a procedure analogous to that described in EXAMPLE 2, Step B. Boron tribromide (1M in dichloromethane, 8.0 equiv) was used. After water addition, the mixture was extracted with ethyl acetate (3×10 ml). The combined organic phases were dried over anhydrous Na₂SO₄, filtered, and concentrated. The residue was purified by preparative TLC (methanol:water:dichloromethane 25:3:72) to afford the title product of Example 4. MS (APCI+) Calc.: 339.4, Found: 340.1 (M+1).

Example 5

5-[2-Chloro-6-methyl-4-(1H-tetrazol-5-ylamino)-phenoxy]-N-cyclopropyl-2-hydroxy-benzenesulfonamide Step A—Preparation of 5-(2-Chloro-6-methyl-4-nitro-phenoxy)-2-methoxy-benzenesulfonyl chloride To a stirred solution of chlorosulfonic acid (17.3 g, 148 mmol, 8.7 equiv) cooled to 0° C. was slowly added 4-(4-methoxy-phenoxy)-3-chloro-5-methyl-nitrobenzene (5.0 g, 17 mmol). The solution was warmed to RT and stirred for 1 hour, then quenched by the dropwise addition into ice water (about 500 ml). The mixture was then extracted with ethyl acetate (4×100 ml), and the combined organic extracts were washed with saturated aqueous NaHCO3(2×100 ml) and brine (1×100 ml). The aqueous phases were combined and back-extracted twice with ethyl acetate. All of the organic phases were combined and dried over anhydrous Na₂SO₄, filtered, and concentrated. The title product of Step A was used in the next step without purification. MS (APCI⁻) Calc.: 392.2, Found: 372.1 (M-sulfonic acid−1).

Step B—Preparation of 5-(2-Chloro-6-methyl-4-nitro-phenoxy)-N-cyclopropyl-2-methoxy-benzenesulfonamide To a solution of 5-(2-chloro-6-methyl-4-nitro-phenoxy)-2-methoxy-benzenesulfonyl chloride (5.61 g, 14.3 mmol) in dichloromethane (100 ml) at RT was added dropwise a solution of cyclopropylamine (1.22 g, 21.4 mmol) and N,N-diisopropylethylamine (5.55 g, 42.9 mmol) in dichloromethane (30 ml) over 15 minutes. The reaction mixture was stirred for 1 hour at RT, then quenched with aqueous 1N HCl (100 ml). The organic phase was separated, and the aqueous phase was extracted with dichloromethane (2×100 ml). All of the organic phases were combined and extracted twice with aqueous 1N HCl, then three times with saturated aqueous NaHCO₃. The aqueous acidic washes and the aqueous basic washes were combined, respectively, and back-extracted with ethyl acetate (2×50 ml). All of these organic phases were combined with the previously combined organic phases and dried over anhydrous Na₂SO₄, filtered, and concentrated. The residue was purified by silica gel column chromatography (ethyl ether:dichloromethane 0.5:99.5) to afford the title product of Step B. MS (APCI⁻) Calc.: 412.3, Found: 411.1 (M−1).

Step C—Preparation of 5-(2-Chloro-6-methyl-4-nitro-phenoxy)-N-cyclopropyl-2-hydroxy-benzenesulfonamide 5-(2-Chloro-6-methyl-4-nitro-phenoxy)-N-cyclopropyl-2-hydroxy-benzenesulfonamide was prepared from 5-(2-chloro-6-methyl-4-nitro-phenoxy)-2-methoxy-benzenesulfonamide according to a procedure analogous to that described in EXAMPLE 2, Step B. Boron tribromide (1M in dichloromethane, 2.0 equiv) was used. After water addition, the mixture was extracted with dichloromethane (3×50 ml). The combined organic phases were dried over anhydrous Na₂SO₄, filtered, and concentrated. The title product of Step C was used in the next step without purification. MS (APCI⁻) Calc.: 398.3, Found: 397.2 (M−1).

Step D—Preparation of 5-(4-Amino-2-chloro-6-methyl-phenoxy)-N-cyclopropyl-2-hydroxy-benzenesulfonamide 5-(4-Amino-2-chloro-6-methyl-phenoxy)-N-cyclopropyl-2-hydroxy-benzenesulfonamide was prepared from 5-(2-chloro-6-methyl-4-nitro-phenoxy)-N-cyclopropyl-2-hydroxy-benzenesulfonamide according to the procedure described in EXAMPLE 4, Step A. The reaction mixture was hydrogenated for 2.5 hours. Then, the mixture was filtered through Celite® and concentrated, and the title product of Step D was used in the next step without purification.) MS (APCI⁻) Calc.: 368.3, Found: 367.2 (M−1).

Step E—Preparation of 5-(2-Chloro-4-cyanoamino-6-methyl-phenoxy)-N-cyclopropyl-2-hydroxy-benzenesulfonamide 5-(2-Chloro-4-cyanoamino-6-methyl-phenoxy)-N-cyclopropyl-2-hydroxy-benzenesulfonamide was prepared from 5-(4-amino-2-chloro-6-methyl-phenoxy)-N-cyclopropyl-2-hydroxy-benzenesulfonamide according to the procedure described in EXAMPLE 4, Step B. The crude residue was purified by preparative TLC (methanol:dichloromethane 4:96) to afford the title product of Step E. MS (APCI⁻) Calc.: 393.2, Found: 392.0 (M−1).

Step F—Preparation of 5-[2-Chloro-6-methyl-4-(1H-tetrazol-5-ylamino)-phenoxy]-N-cyclopropyl-2-hydroxy-benzenesulfonamide 5-[2-Chloro-6-methyl-4-(1H-tetrazol-5-ylamino)-phenoxy]-N-cyclopropyl-2-hydroxy-benzenesulfon-amide was prepared from 5-[2-chloro-4-cyanoamino-6-methyl-phenoxy]-N-cyclopropyl-2-hydroxy-benzenesulfonamide according to a procedure analogous to that described in EXAMPLE 1, Step C. Sodium azide (1.2 equiv) and ammonium chloride (10 equiv) were used, and the reaction was heated to 165° C. for 3 hours. After the reaction had been acidified, the aqueous mixture was washed with ethyl acetate (3×10 ml). The combined organic extracts were extracted with aqueous 1N HCl (3×50 ml), and brine (50 ml). The organic phase was dried over anhydrous $Na_2SO_4$, filtered, and concentrated. The residue was purified by preparative TLC (methanol:water:dichloromethane 25:3:72) to afford the title product of Example 5. MS (APCI⁺) Calc.: 436.1, Found: 436.9 (M+1).

EXAMPLE 5-1 was prepared in an analogous manner to the sequence of reactions described for EXAMPLE 5 with the noted changes.

Example 5-1

N-Cyclopropyl-5-[2,6-dichloro-4-(1H-tetrazol-5-ylamino)-phenoxy]-2-hydroxy-benzenesulfonamide MS (APCI⁺) Calc.: 456.0, Found: 457.3 (M+1).

4-(4-methoxy-phenoxy)-3,5-dichloronitrobenzene was substituted for 4-(4-methoxy-phenoxy)-3-chloro-5-methylnitrobenzene in Step A.

Example 6

N-Cyclobutyl-5-[2,6-dimethyl-4-(1H-tetrazol-5-ylamino)-phenoxy]-2-hydroxy-N-methyl-benzamide Step A—Preparation of 5-(2,6-Dimethyl-4-nitro-phenoxy)-2-methoxy-benzaldehyde To a solution of 4-(4-methoxy-phenoxy)-3,5-dimethyl-nitrobenzene (7.0 g, 25.6 mmol) dissolved in trifluoroacetic acid (60 ml) at RT was added hexamethylenetetramine (5.75 g, 41.0 mmol), and the solution was heated to 75° C. and stirred for 6 hours. The reaction mixture was then concentrated to dryness, and the residue was taken up in water (150 ml) and stirred at RT for 20 hours. The mixture was then extracted with a 10% solution of methanol/dichloromethane (4×50 ml) and ethyl acetate (1×75 ml). All of the organic phases were combined, dried over anhydrous $Na_2SO_4$, filtered, and concentrated. The residue was then triturated with ethyl ether, cooled to 0° C., and the title product of Step A was collected by filtration. MS (APCI⁻) Calc.: 301.3, Found: 300 (M−1).

Step B—Preparation of 5-(2,6-Dimethyl-4-nitro-phenoxy)-2-methoxy-benzoic acid

To a solution of 5-(2,6-dimethyl-4-nitro-phenoxy)-2-methoxy-benzaldehyde (6.56 g, 21.8 mmol) in tetrahydrofuran (31 ml) was added t-butyl alcohol (215 ml), then 2-methyl-2-butene (27.5 ml, 327 mmol). To this mixture was added dropwise a solution of $NaClO_2$ (17.8 g, 196 mmol) dissolved in aqueous $KH_2PO_4$ buffer (254 ml of a 0.6M solution, 153 mmol), and the reaction mixture was stirred at RT for 16 hours. An aqueous saturated solution of $Na_2S_2O_3$ (100 ml) was then added, the mixture was stirred for 30 minutes at room temperature, then extracted with ethyl acetate (3×300 ml). The combined organic phases were dried over anhydrous $Na_2SO_4$, filtered, and concentrated. The remaining t-butyl alcohol was azeotroped with hexanes. The title product of Step B was used in the next step without purification. MS (APCI⁻) Calc.: 317.3, Found: 316.3 (M−1).

Step C—Preparation of N-Cyclobutyl-5-(2,6-dimethyl-4-nitro-phenoxy)-2-methoxy-benzamide To a cooled solution of 5-(2,6-Dimethyl-4-nitro-phenoxy)-2-methoxy-benzoic acid (2.6 g, 8.2 mmol) in THF (80 ml) at 0° C. was added N-methylmorpholine (1.7 g, 16.5 mmol) and isobutylchloroformate (1.7 g, 12.3 mmol). After stirring at 0° C. for 45 minutes, cyclobutyl amine (1.2 g, 16.5 mmol) was added. The resulting mixture was stirred at 0° C. for 15 minutes, then at room temperature for 2 hours. The solution was concentrated in vacuo, and the residue was partitioned between ethyl acetate (75 ml) and 1 N HCl (75 ml). The EtOAc extract was washed with 1N HCl (2×75 ml). The combined aqueous washings were extracted with EtOAc (2×50 ml). The combined organic extracts were dried over sodium sulfate and concentrated. The title product of Step C was purified by chromatography to give an off-white solid. MS (APCI⁻) Calc.: 370.4, Found: 369.1 (M−1).

Step D—Preparation of N-Cyclobutyl-5-(2,6-dimethyl-4-nitro-phenoxy)-2-methoxy-N-methyl-benzamide To a solution of N-cyclobutyl-5-(2,6-dimethyl-4-nitro-phenoxy)-2-methoxy-benzamide (125 mg, 0.34 mmol) in N,N-dimethylformamide (4.0 ml) cooled to 0° C. was added NaH (20 mg, 0.84 mmol), and the reaction was stirred for 15 minutes at 0° C. Methyl iodide (0.10 ml, 1.7 mmol) was added, and the reaction mixture was stirred for 18 hours at room temperature. An aqueous solution of 1N HCl (50 ml) was added, and the mixture was extracted with ethyl acetate (3×15 ml). The combined organic phases were dried over anhydrous $Na_2SO_4$, filtered, and concentrated. The residue was purified by preparative TLC (ethyl acetate:hexanes=3:2) to afford the title product of Step D. MS (APCI⁺) Calc.: 384.4, Found: 385.2 (M+1).

Step E—Preparation of N-Cyclobutyl-5-(2,6-dimethyl-4-nitro-phenoxy)-2-hydroxy-N-methyl-benzamide N-Cyclobutyl-5-(2,6-dimethyl-4-nitro-phenoxy)-2-hydroxy-N-methyl-benzamide was prepared from N-cyclobutyl-5-(2,6-dimethyl-4-nitro-phenoxy)-2-methoxy-N-methyl-benzamide according to a procedure analogous to that described in EXAMPLE 2, Step B. Boron tribromide (1M in dichloromethane, 2.0 equiv) was used. After water addition, the mixture was extracted with dichloromethane (3×10 ml). The combined organic phases were dried over anhydrous $Na_2SO_4$, filtered, and concentrated. The title product of Step E was used in the next step without purification. MS (APCI⁺) Calc.: 370.4, Found: 371.1 (M+1).

Step F—Preparation of 5-(4-Amino-2,6-dimethyl-phenoxy)-N-cyclobutyl-2-hydroxy-N-methyl-benzamide 5-(4-Amino-2,6-dimethyl-phenoxy)-N-cyclobutyl-2-hydroxy-N-methyl-benzamide was prepared from N-cyclobutyl-5-(2,6-dimethyl-4-nitro-phenoxy)-2-hydroxy- N-methyl-benzamide according to a procedure analogous to that described in EXAMPLE 4, Step A. Methanol was used instead of ethanol as a co-solvent. The reaction mixture was hydrogenated for 2 hours. Then, the mixture was filtered through Celite® and concentrated, and the title product of Step F was used in the next step without purification. MS (APCI$^+$) Calc.: 340.4, Found: 341.1 (M+1).

Step G—Preparation of 5-(4-Cyanoamino-2,6-dimethyl-phenoxy)-N-cyclobutyl-2-hydroxy-N-methyl-benzamide 5-(4-Cyanoamino-2,6-dimethyl-phenoxy)-N-cyclobutyl-2-hydroxy-N-methyl-benzamide was prepared from 5-(4-amino-2,6-dimethyl-phenoxy)-N-cyclobutyl-2-hydroxy-N-methyl-benzamide according to a procedure analogous to that described in EXAMPLE 4, Step B. Upon work-up, the reaction mixture was diluted with 1N HCl (10 ml) and extracted with ethyl acetate (3×10 ml). The combined organic phases were washed with 1N HCl (3×40 ml), brine (40 ml), then dried over anhydrous Na$_2$SO$_4$, filtered, and concentrated. The residue was purified by preparative TLC (ethyl acetate:hexanes 4:1) to afford the title product of Step G. MS (APCI$^+$) Calc.: 365.4, Found: 366.1 (M+1).

Step H—Preparation of N-Cyclobutyl-5-[2,6-dimethyl-4-(1H-tetrazol-5-ylamino)-phenoxy]-2-hydroxy-N-methyl-benzamide N-Cyclobutyl-5-[2,6-dimethyl-4-(1H-tetrazol-5-ylamino)-phenoxy]-2-hydroxy-N-methyl-benzamide was prepared from 5-(4-cyanoamino-2,6-dimethyl-phenoxy)-N-cyclobutyl-2-hydroxy-N-methyl-benzamide according to a procedure analogous to that described in EXAMPLE 1, Step C. Sodium azide (1.2 equiv) and ammonium chloride (10 equiv) were used, and the reaction was heated to 165° C. for 5 hours. After the reaction had been acidified, the aqueous mixture was washed with ethyl acetate (3×10 ml). The combined organic extracts were extracted with aqueous 1N HCl (3×50 ml), and brine (50 ml). The organic phase was dried over anhydrous Na$_2$SO$_4$, filtered, and concentrated. The residue was purified by preparative TLC (methanol:water:dichloromethane 15:1.5:83.5) to afford the title product of Example 6. MS (APCI$^+$) Calc.: 408.5, Found: 409.2 (M+1).

Example 7

2-Cyclopropylmethanesulfonyl-4-[2,6-dimethyl-4-(1H-tetrazol-5-ylamino)-phenoxy]-phenol Step A—Preparation of 5-(2,6-Dimethyl-4-nitro-phenoxy)-2-methoxy-benzenesulfinic acid To a solution of chlorosulfonic acid (2.4 ml, 36.6 mmol) cooled to 0° C. was slowly added 4-(4-methoxy-phenoxy)-3,5-dimethyl-nitrobenzene (2.00 g, 7.3 mmol). The reaction was stirred at RT for 3 hours, then the mixture was added dropwise to ice-water (150 ml). The mixture was extracted with ethyl acetate (3×100 ml), and the combined organic phases were extracted with brine, dried over anhydrous Na$_2$SO$_4$, filtered, and concentrated. To the residue was added NaHCO$_3$ (3.69 g, 43.9 mmol), Na$_2$SO$_3$ (2.78 g, 22.0 mmol), and water (25 ml). The mixture was heated to reflux for 3 hours, then cooled to RT. The mixture was acidified carefully with concentrated HCl, and then extracted with ethyl acetate (3×50 ml). The combined organic phases were washed with brine, dried over anhydrous Na$_2$SO$_4$, filtered, and concentrated. The title product of Step A was used in the next step without further purification. MS (APCI$^-$) Calc.: 337.4, Found: 336.1 (M-1).

Step B—Preparation of 5-(2,6-Dimethyl-4-nitro-phenoxy)-2-methoxy-cyclopropylmethanesulfonylbenzene 5-(2,6-Dimethyl-4-nitro-phenoxy)-2-methoxy-benzenesulfinic acid (1.88 g, 5.57 mmol) was dissolved in a solution of NaOH (0.22 g, 5.57 mmol, 1.0 equiv) in ethanol (25 ml). Bromomethyl-cyclopropane (3.76 g, 27.9 mmol, 5.0 equiv) was added, and the solution was heated to reflux for 6 h, with periodic addition of aqueous 32% NaOH solution to maintain basicity. The mixture was then cooled to RT and acidified with aqueous 1N HCl solution. The mixture was then diluted with water (100 ml) and extracted with ethyl acetate (3×50 ml). The combined organic phases were washed with brine, dried over anhydrous Na$_2$SO$_4$, filtered, and concentrated. The residue was purified by silica gel chromatography (ethyl acetate:hexanes grading to 40:60) to afford the title product of Step B. MS (APCI$^-$) Calc.: 391.4, Found: 390.2 (M-1).

Step C—Preparation of 2-Cyclopropylmethanesulfonyl-4-(2,6-dimethyl-4-nitro-phenoxy)-phenol 2-Cyclopropylmethanesulfonyl-4-(2,6-dimethyl-4-nitro-phenoxy)-phenol was prepared from 5-(2,6-dimethyl-4-nitro-phenoxy)-2-methoxy-cyclopropylmethanesulfonylbenzene according to a procedure analogous to that described in EXAMPLE 2, Step B. Boron tribromide (1M in dichloromethane, 2.0 equiv) was used. After 30 minutes, ice water (50 ml) was added to quench the reaction, and the mixture was extracted with dichloromethane (3×25 ml). The combined organic phases were dried over anhydrous Na$_2$SO$_4$, filtered, and concentrated. The residue was dissolved in ethyl acetate/methanol and stirred with activated carbon, then filtered through Celite® and concentrated. The title product of Step C was used in the next step without further purification. MS (APCI$^-$) Calc.: 377.4, Found: 376.1 (M-1).

Step D—Preparation of 4-(4-Amino-2,6-dimethyl-phenoxy)-2-cyclopropylmethanesulfonyl-phenol 4-(4-Amino-2,6-dimethyl-phenoxy)-2-cyclopropylmethanesulfonyl-phenol was prepared from 2-cyclopropylmethanesulfonyl-4-(2,6-dimethyl-4-nitro-phenoxy)-phenol according to a procedure analogous to that described in EXAMPLE 4, Step A. Methanol was used instead of ethanol as a co-solvent. Reaction mixture was hydrogenated for 3 hours. After the mixture was filtered through Celite® and concentrated, the title product of Step D was used in the next step without purification. MS (APCI$^-$) Calc.: 347.4, Found: 346.0 (M-1).

Step E—Preparation of 4-(3-Cyclopropylmethanesulfonyl-4-hydroxy-phenoxy)-3,5-dimethyl-phenyl-cyanamide 4-(3-Cyclopropylmethanesulfonyl-4-hydroxy-phenoxy)-3,5-dimethyl-phenyl-cyanamide was prepared from 4-(4-amino-2,6-dimethyl-phenoxy)-2-cyclopropylmethanesulfonyl-phenol according to a procedure analogous to that described in EXAMPLE 4, Step B. During work-up, the combined organic phases were washed with 1N HCl (2×50 ml) instead of aqueous saturated sodium bicarbonate solution. The residue was purified by preparative TLC (methanol:dichloromethane 4:96) to afford the title product of Step E. MS (APCI$^-$) Calc.: 372.4, Found: 371.4 (M-1).

Step F—Preparation of 2-Cyclopropylmethanesulfonyl-4-[2,6-dimethyl-4-(1H-tetrazol-5-ylamino)-phenoxy]-phenol 2-Cyclopropylmethanesulfonyl-4-[2,6-dimethyl-4-(1H-tetrazol-5-ylamino)-phenoxy]-phenol was prepared from 4-(3-cyclopropylmethanesulfonyl-4-hydroxy-phenoxy)-3,5-dimethyl-phenyl-cyanamide according to a procedure analogous to that described in EXAMPLE 1, Step C. Sodium azide (1.5 equiv) and ammonium chloride (10 equiv) were used, and the reaction was heated to 140° C. for 20 hours. After the reaction had been acidified, the aqueous mixture was extracted with ethyl acetate (3× 10 ml). The combined organic extracts were washed with aqueous 1N HCl (3×50 ml), and brine (50 ml). The organic phase was dried over anhydrous $Na_2SO_4$, filtered, and concentrated. The residue was purified by preparative TLC (methanol:water:dichloromethane=15:1.5:83.5) to afford the title product of Example 7. MS (APCI⁻) Calc.: 415.1, Found: 413.8 (M−1).

The following compounds can also be made procedures analogous to those set forth above:

2-cyclobutylmethanesulfonyl-4-[2,6-dimethyl-4-(2H-tetrazol-5-ylamino)-phenoxy]-phenol;

2-cyclobutylmethanesulfonyl-4-[2,6-dichlorol-4-(2H-tetrazol-5-ylamino)-phenoxy]-phenol;

4-[2-chloro-6-methyl-4-(2H-tetrazol-5-ylamino)-phenoxy]-2-cyclobutylmethanesulfonyl-phenol;

2-cyclopentylmethanesulfonyl-4-[2,6-dimethyl-4-(2H-tetrazol-5-ylamino)-phenoxy]-phenol;

2-cyclopentylmethanesulfonyl-4-[2,6-dichlorol-4-(2H-tetrazol-5-ylamino)-phenoxy]-phenol;

4-[2-chloro-6-methyl-4-(2H-tetrazol-5-ylamino)-phenoxy]-2-cyclopentylmethanesulfonyl-phenol;

2-cyclohexylmethanesulfonyl-4-[2,6-dimethyl-4-(2H-tetrazol-5-ylamino)-phenoxy]-phenol;

2-cyclohexylmethanesulfonyl-4-[2,6-dichlorol-4-(2H-tetrazol-5-ylamino)-phenoxy]-phenol;

4-[2-chloro-6-methyl-4-(2H-tetrazol-5-ylamino)-phenoxy]-2-cyclohexylmethanesulfonyl-phenol;

4-[2,6-dimethyl-4-(2H-tetrazol-5-ylamino)-phenoxy]-2-(4-fluoro-benzenesulfonyl)-phenol;

4-[2,6-dichloro-4-(2H-tetrazol-5-ylamino)-phenoxy]-2-(4-fluoro-benzenesulfonyl)-phenol; and 4-[2-chloro-6-methyl-4-(2H-tetrazol-5-ylamino)-phenoxy]-2-(4-fluoro-benzenesulfonyl)-phenol.

BIOLOGICAL ASSAYS

The utility of the compounds of the present invention can be evidenced by activity in at least one of the assays described below.

Assay 1
Oxygen Consumption

As would be appreciated by those skilled in the relevant art, during increased energy expenditure, animals generally consume more oxygen. In addition, metabolic fuels such as, for example, glucose and fatty acids, are oxidized to $CO_2$ and $H_2O$ with the concomitant evolution of heat, commonly referred to in the art as thermogenesis. Thus, the measurement of oxygen consumption in animals, including humans and companion animals, is an indirect measure of thermogenesis. Indirect calorimetry is commonly used in animals, e.g., humans, by those skilled in the relevant art to measure such energy expenditures.

Those skilled in the art understand that increased energy expenditure and the concomitant burning of metabolic fuels resulting in the production of heat may be efficacious with respect to the treatment of, e.g., obesity. As is well known by those skilled in the art, thyroid hormones affect cardiac functioning, for example, by causing an increase in the heart rate and, accordingly, an increase in oxygen consumption with concomitant heat production.

The ability of compounds of the present invention to generate a thermogenic response may be demonstrated according to the following protocol.

A. Experimental

This in vivo screen is designed to evaluate the efficacy and cardiac effects of compounds that are tissue-selective thyroid hormone agonists. The efficacy endpoints measured are whole body oxygen consumption and the activity of liver mitochondrial alpha-glycerophosphate dehydrogenase ("mGPDH"). The cardiac endpoints that are measured are heart weight and heart mGPDH activity. The protocol involves: (a) dosing fatty Zucker rats for about 6 days, (b) measuring oxygen consumption and (c) harvesting tissue for preparation of mitochondria and subsequent assaying of enzyme activity thereby.

B. Preparation of Rats

Male fatty Zucker rats having a body weight range of from about 400 g to about 500 g are housed for from about 3 to about 7 days in individual cages under standard laboratory conditions prior to the initiation of the study.

A compound of Formula I, or a pharmaceutically acceptable salt or prodrug or salt of the prodrug of a compound of Formula I, vehichle, or $T_3$ sodium salt, is administered by oral gavage as a single daily dose given between about 3 p.m. to about 6 p.m. for about 6 days. A compound of Formula I, or a pharmaceutically acceptable salt or prodrug or salt of the prodrug of a compound of Formula I, or $T_3$ sodium salt is dissolved in a suitably small volume of about 1N NaOH and then brought up to a suitable volume with about 0.01N NaOH containing about 0.25% of methyl cellulose (10:1, 0.01N NaOH/MC:1N NaOH). The dosing volume is about 1 ml.

C. Oxygen Consumption

About 1 day after the last dose of the compound is administered, oxygen consumption is measured using an open circuit, indirect calorimeter (Oxymax, Columbus Instruments, Columbus, Ohio 43204). The Oxymax gas sensors are calibrated with $N_2$ gas and a gas mixture (about 0.5% of $CO_2$, about 20.5% of $O_2$, about 79% of $N_2$) before each experiment.

The subject rats are removed from their home cages and their body weights recorded. The rats are placed into the sealed chambers (43×43×10 cm) of the Oxymax, the chambers are placed in the activity monitors, and the air flow rate through the chambers is then set at from about 1.6 l/min to about 1.7 l/min.

The Oxymax software then calculates the oxygen consumption (ml/kg/h) by the rats based on the flow rate of air through the chambers and the difference in oxygen content at the inlet and output ports. The activity monitors have 15 infrared light beams spaced about one inch apart on each axis, and ambulatory activity is recorded when two consecutive beams are broken, and the results are recorded as counts.

Oxygen consumption and ambulatory activity are measured about every 10 minutes for from about 5 hours to about 6.5 hours. Resting oxygen consumption is calculated on individual rats by averaging the values excluding the first 5 values and the values obtained during time periods where ambulatory activity exceeds about 100 counts.

Assay 2
Binding to Thyroid Hormone Receptors

The ability of a compounds of the present invention, ("the test thyromimetic compounds"), to bind to thyroid hormone receptors can be demonstrated in the following protocol.

A. Preparation of Insect Cell Nuclear Extracts

High Five cell pellets (BTI-TN-5B1-4, catalog number B855-02, Invitrogen®, Carlsbad, Calif.) obtained about 48 hours after infection with baculovirus (GibcoBRL®, Gaithersburg, Md.) expressing either human TRα or TRβ are suspended in ice cold Sample Buffer (10 mM Tris, pH 8.0; 1 mM $MgCl_2$; 1 mM DTT; 0.05% Tween 20; 1 mM 4-(2-aminoethyl)-benzenesulfonylfluoride; 25 μg/ml leupeptin). After about 10 minutes incubation on ice, the suspension is homogenized by 20 strokes with a Dounce homogenizer (VWR® Scientific Products, West Chester, Pa.) and centrifuged at 800×g for about 15 minutes at 4° C. The pellet (nuclei) is suspended in a hypertonic buffer (0.4 M KCl; 10 mM Tris, pH 8.0; 1 mM $MgCl_2$; 1 mM DTT; 0.05% Tween 20) and incubated for about 30 min on ice. The suspension is centrifuged at 100,000×g for about 30 minutes at 4° C. The supernatant (nuclear extract) is stored in 0.5 ml aliquots at −80° C.

B. Binding Assay

Competition binding assays to measure the interaction of the test thyromimetic compounds with thyroid hormone receptor α1 and β1 (TRα and TRβ) are carried out according to the following protocol.

Solutions of test thyromimetic compounds (final compound concentration of 20 mM) are prepared using 100% DMSO as a solvent. Each compound is serially diluted in an assay buffer (5 mM Tris-HCl, pH 8.0; 50 mM NaCl; 2 mM EDTA; 10% (v/v) glycerol; 1 mM DTT, "assay buffer") containing 0.4 nM $^{125}$I-T$_3$ (specific activity of about 2200 Ci/mmol) to yield solutions that vary in compound concentration from about 10 μM to about 0.1 nM.

High Five insect cell nuclear extract containing either TRα or TRβ is diluted to a total protein concentration of 0.0075 mg/ml using the assay buffer as diluent.

One volume (100 μl) of each thyromimetic compound dilution (containing 0.4 nM $^{125}$I-T3) is combined with an equal volume (100 μl) of diluted nuclear extract containing TRα1 or TRβ1, and incubated at RT for about 90 min. A one hundred and fifty μl sample of the binding reaction is removed and placed into a 96-well filter plate (Millipore®, Bedford, Mass.) that has been pre-washed with ice-cold assay buffer. The plate is subjected to vacuum filtration using a filtration manifold (Millipore®). Each well is washed five times by the addition of 200 μl of ice-cold assay buffer and subsequent vacuum filtration. The plate is removed from the vacuum filtration manifold, the bottom of the plate is briefly dried on paper towels, then 25 μl of Wallac® (EG&G Wallac®, Gaithersburg, Md.) Optiphase Supermix scintillation cocktail is added to each well and the top of the plate is covered with plastic sealing tape (Microplate Press-on Adhesive Sealing Film, Packard® Instrument Co., Inc., Downers Grove, Ill.) and the radioactivity is quantitated using a Wallac® Microbeta 96-Well plate scintillation counter.

What is claimed is:

1. A compound of Formula I

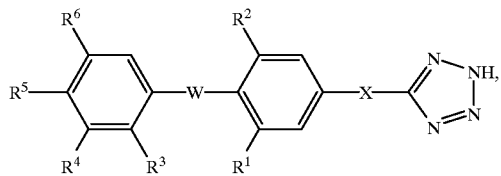

I or a stereoisomer, or a pharmaceutically acceptable salt thereof wherein:

W is O, S, SO, $SO_2$, $CH_2$, $CF_2$, CHF, C(=O), CH(OH), $NR^a$, or

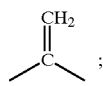

X is O, $CH_2$, $CH_2CH_2$, S, SO, $SO_2$, $CH_2NR^a$, $NR^a$ or a bond;

each $R^a$ is independently hydrogen, $C_1$–$C_6$alkyl, or $C_1$–$C_6$alkyl substituted with one substituent selected from $C_3$–$C_6$cycloalkyl or methoxy;

$R^1$, $R^2$, $R^3$ and $R^6$ are independently hydrogen, halogen, $C_1$–$C_8$alkyl, —$CF_3$, —$OCF_3$, —$OC_1$–$C_8$alkyl, or —CN;

$R^4$ is hydrogen, $C_1$–$C_{12}$alkyl, $C_1$–$C_{12}$alkyl that is substituted with from one to three substituents independently selected from Group V, $C_2$–$C_{12}$ alkenyl, $C_2$–$C_{12}$ alkynyl, halogen, —CN, —$OR^b$, —$SR^c$, —S(=O)$R^c$, —S(=O)$_2R^c$, aryl, heteroaryl, $C_3$–$C_{10}$ cycloalkyl, heterocycloalkyl, —S(=O)$_2NR^cR^d$, —C(=O)$NR^cR^d$, —C(=O)$OR^e$, —$NR^aC$(=O)$R^d$, —$NR^aC$(=O)$NR^cR^d$, —$NR^aS$(=O)$_2R^d$, —$NR^aR^d$, —C(=O)$R^c$, or $R^3$ and $R^4$ are taken together with the carbon atoms to which they are attached to form an unsubstituted or substituted carbocyclic ring of formula —$(CH_2)_i$— or an unsubstituted or substituted heterocyclic ring selected from the group consisting of —Q—$(CH_2)_j$— and —$(CH_2)_k$—Q—$(CH_2)_l$— wherein Q is O, S or $NR^a$; i is 3, 4, 5, 6 or 7; j is 2, 3, 4, 5, or 6; k and l are each independently 1, 2, 3, 4, or 5, and any substituents up to four are selected from $C_1$–$C_4$alkyl, —$OR^b$, oxo, —CN, phenyl, or —$NR^aR^g$;

$R^b$ is hydrogen, $C_1$–$C_{12}$alkyl, $C_1$–$C_{12}$alkyl substituted with one to three substituents independently selected from Group V, aryl, heteroaryl, $C_3$–$C_{10}$ cycloalkyl, heterocycloalkyl, —C(=O)$NR^cR^d$, or —C(=O)$R^f$;

$R^c$ and $R^d$ are each independently selected from hydrogen, $C_1$–$C_{12}$alkyl, $C_1$–$C_{12}$alkyl substituted with one to three substituents independently selected from Group VI, $C_2$–$C_{12}$alkenyl, $C_2$–$C_{12}$alkynyl, aryl, heteroaryl, $C_3$–$C_{10}$ cycloalkyl, heterocycloalkyl, or $R^c$ and $R^d$ may together along with the atom(s) to which they are attached form a 3–10 membered unsubstituted or substituted heterocyclic ring, which may contain a second heterogroup selected from O, $NR^e$, or S, wherein any substituents up to four are selected from $C_1$–$C_4$alkyl, —$OR^b$, oxo, —CN, phenyl, or —$NR^g$;

$R^5$ is —OH, —$OC_1$–$C_6$alkyl, —OC(=O)$R^f$, —F, —C(=O)$OR^c$, or $R^4$ and $R^5$ may together with the atom(s) to which they are attached form a heterocyclic ring selected from the group consisting of —$CR^c$=$CR^a$—NH—, —N=$CR^a$—NH—, —$CR^c$=$CR^a$—O—, —$CR^c$=$CR^a$—S—, —$CR^c$=N—NH—, or —$CR^a$=$CR^a$—$CR^a$=N—;

Group V is halogen; —$CF_3$; —$OCF_3$; hydroxy; oxo; $C_1$–$C_6$alkoxy; —CN; aryl; heteroaryl; $C_3$–$C_{10}$cycloalkyl; heterocycloalkyl; —$SR^5$; —S(=O)$R^f$; —S(=O)$_2R^f$; —S(=O)$_2NR^aR^f$, wherein $R^a$ and $R^f$ may together along with the atom(s) to which they are attached form a 3–8 membered heterocyclic ring, which may contain a second heterogroup selected from O, $NR^e$ or S; —$NR^aR^g$; or —C(=O)$NR^aR^f$, wherein $R^a$ and $R^f$ may together along with the atom(s) to which they are attached form a 3–8 membered heterocyclic ring, which may contain a second heterogroup selected from O, $NR^e$ or S;

Group VI is halogen, hydroxy, oxo, $C_1$–$C_6$alkoxy, aryl, heteroaryl, $C_3$–$C_8$cycloalkyl, heterocycloalkyl, —CN, or —$OCF_3$;

$R^e$ is hydrogen, —CN, $C_1$–$C_{10}$alkyl, $C_1$–$C_{10}$alkyl substituted with one to three substitutents independently selected from Group V, $C_2$–$C_{10}$alkenyl, $C_2$–$C_{10}$alkoxy, $C_3$–$C_{10}$cycloalkyl, aryl, heteroaryl, —C(=O)$R^f$, —C(=O)O$R^f$, —C(=O)N$R^aR^f$ —S(=O)$_2$N$R^aR^f$, or —S(=O)$_2R^f$;

$R^f$ is hydrogen, $C_1$–$C_{10}$alkyl, $C_1$–$C_{10}$alkyl substituted with from one to three substituents selected from Group VI, $C_2$–$C_{10}$alkenyl, $C_2$–$C_{10}$alkoxy, $C_3$–$C_{10}$cycloalkyl, heterocycloalkyl, aryl, or heteroaryl; and $R^g$ is hydrogen, $C_1$–$C_6$alkyl, $C_3$–$C_8$cycloalkyl, $C_2$–$C_6$ alkenyl, aryl, —C(=O)$R^f$, —C(=O)O$R^f$, —C(=O)N$R^aR^f$, or —S(=O)$_2R^f$, provided that $R^1$ and $R^2$ are not both hydrogen, further provided that when X is $CH_2$, W is $NR^a$, $R^3$ is hydrogen and $R^5$ is —OH, then $R^6$ and $R^4$ are not both —C(H$_3$)$_3$, further provided that when X is $CH_2$ or $CH_2CH_2$, W is O, and $R^3$ and $R^6$ are hydrogen, then $R^4$ is not halogen, —CF$_3$, $C_1$–$C_6$alkyl or $C_3$–$C_7$cycloalkyl, and further provided that when $R^3$ and $R^4$ are hydrogen and W is O then $R^6$ is not halogen, —CF$_3$, $C_1$–$C_6$alkyl or $C_3$–$C_7$cycloalkyl.

2. A compound of claim 1 wherein W is O.
3. A compound of claim 1 wherein X is a bond, NH, or $CH_2$.
4. A compound of claim 1 wherein $R^1$ and $R^2$ are independently $C_1$–$C_8$alkyl, halogen, or —CN.
5. A compound of claim 4 wherein the $C_1$–$C_8$alkyl groups are —CH$_3$ and the halogens are chlorine, bromine, or iodine.
6. A compound of claim 1 wherein $R^6$ is hydrogen.
7. A compound of claim 1 wherein $R^5$ is —OH, —OC(=O)$R^f$, or —F.
8. A compound of claim 1 wherein W is O;
X is a bond, NH, or $CH_2$;
$R^1$ and $R^2$ are independently —CH$_3$, Cl, Br, or I;
$R^6$ is hydrogen;
$R^5$ is —OH;
$R^3$ is hydrogen, halogen, $C_1$–$C_6$alkyl, —CF$_3$, —OCF$_3$, —OC$_1$–C$_6$alkyl, or —CN; and
$R^4$ is hydrogen, $C_1$–$C_{12}$alkyl, $C_1$–$C_{12}$alkyl that is substituted with from one to three substituents independently selected from Group V, $C_2$–$C_{12}$ alkenyl, $C_2$–$C_{12}$ alkynyl, halogen, —CN, —O$R^b$, —S$R^c$, —S(=O)$R^c$, —S(=O)$_2R^c$, aryl, heteroaryl, $C_3$–$C_{10}$ cycloalkyl, heterocycloalkyl, —S(=O)$_2$N$R^cR^d$, —C(=O)N$R^cR^d$, —C(=O)O$R^c$, —N$R^a$C(=O)$R^d$, —N$R^a$C(=O)N$R^cR^d$, —N$R^a$S(=O)$_2R^d$, —N$R^aR^d$, wherein aryl is phenyl or naphthyl either unsubstituted or substituted with from one to four substituents selected from halogen, $C_1$–$C_4$alkyl, $C_1$–$C_4$alkoxy, —OCF$_3$, —CN, —S$R^f$, —S(=O)$R^f$, —S(=O)$_2R^f$, $C_3$–$C_6$cycloalkyl, —S(=O)$_2$N$R^aR^f$, —N$R^aR^g$, —C(=O)N$R^aR^f$, —OH, or $C_1$–$C_4$perfluoroalkyl; wherein heteroaryl is an unsubstituted, monosubstituted or disubstituted five or six membered aromatic ring having from 1 to 3 heteroatoms independently selected from O, N, or S, and wherein any substituents are selected from halogen, $C_1$–$C_4$alkyl, $C_1$–$C_4$alkoxy, —CF$_3$, —OH, —N$R^aR^g$, —CO$_2R^f$, or form a fused benzo group; and heterocycloalkyl is either unsubstituted or substituted with from one to four substituents selected from $C_1$–$C_4$ alkyl, —OH, oxo, $C_1$–$C_4$alkoxy, —CN, phenyl, or —N$R^aR^e$, or $R^3$ and $R^4$ may be taken together with the carbon atoms to which they are attached to form a carbocyclic ring of formula —(CH$_2$)$_i$— or a heterocyclic ring selected from the group consisting of —Q—(CH$_2$)$_j$— and —(CH$_2$)$_k$—Q—(CH$_2$)$_l$— wherein Q is O, S or N$R^a$; i is 3, 4, 5, 6 or 7; j is 2, 3, 4, 5, or 6; and k and l are each independently 2, 3, 4, 5, or 6.

9. A compound of Formula I

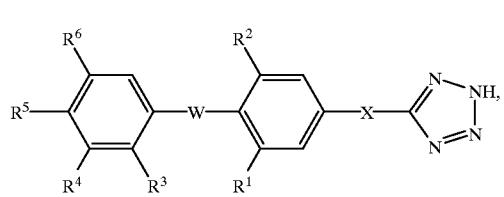

or a stereoisomer, pharmaceutically acceptable salt thereof wherein:

W is O;
X is a bond or NH;
$R^1$ and $R^2$ are independently halogen or $C_1$-$C_8$alkyl;
$R^3$ and $R^6$ are hydrogen;
$R^5$ is —OH;
$R^4$ is $C_1$-$C_8$ alkyl, —S(=O)$_2$N$R^cR^d$, —C(=O)N$R^cR^d$ or —S(=O)$_2R^c$, and
$R^c$ and $R^d$ are independently hydrogen, $C_1$-$C_{12}$alkyl, $C_3$-$C_{10}$cycloalkyl, aryl, heteroaryl, substituted cycloalkyl, heterocycloalkyl, aryl, heteroaryl, or $R^c$ and $R^d$ taken together with the nitrogen atom to which they are attached form a heterocycloalkyl ring or a substituted heterocycloalkyl ring.

10. The compound:
4-[2,6-dimethyl-4-(2H-tetrazol-5-yl)-phenoxy]-2-isopropyl-phenol;
4-[2,6-dichloro-4-(1H-tetrazol-5-yl)-phenoxy]-2-isopropyl-phenol;
4-[2,6-dichloro-4-(2H-tetrazol-5-yl)-phenoxy]-2-(pyrrolidine-1-sulfonyl)-phenol;
4-[2,6-dichloro-4-(2H-tetrazol-5-yl)-phenoxy]-2-(piperidine-1-sulfonyl)-phenol;
4-[2,6-dichloro-4-(2H-tetrazol-5-yl)-phenoxy]-2-(3,3-dimethyl-piperidine-1-sulfonyl)-phenol;
N-cyclopropyl-5-[2,6-dichloro-4-(2H-tetrazol-5-yl)-phenoxy]-2-hydroxy-benzenesulfonamide;
5-[2,6-dichloro-4-(2H-tetrazol-5-yl)-phenoxy]-2-hydroxy-N,N-dimethyl-benzenesulfonamide;
{5-[2,6-dichloro-4-(1H-tetrazol-5-yl)-phenoxy]-2-hydroxy-phenyl}-piperidin-1-yl-methanone;
N-cyclobutyl-5-[2,6-dichloro-4-(1H-tetrazol-5-yl)-phenoxy]-2-hydroxy-benzamide; and
N-cyclohexyl-5-[2,6-dichloro-4-(1H-tetrazol-5-yl)-phenoxy]-2-hydroxy-benzamide; or a stereoisomer, or a pharmaceutically acceptable salt thereof.

11. The compound:
{5-[2,6-dichloro-4-(1H-tetrazol-5-yl)-phenoxy]-2-hydroxy-phenyl}-pyrrolidin-1-yl-methanone;
N-bicyclo[2.2.1]hept-2-yl-5-[2,6-dichloro-4-(1H-tetrazol-5-yl)-phenoxy]-2-hydroxy-benzamide;
4-[2,6-dimethyl-4-(1H-tetrazol-5-ylamino)-phenoxy]-2-isopropyl-phenol;
5-[2-chloro-6-methyl-4-(1H-tetrazol-5-ylamino)-phenoxy]-N-cyclopropyl-2-hydroxy-benzenesulfonamide;
N-cyclopropyl-5-[2,6-dichloro-4-(1H-tetrazol-5-ylamino)-phenoxy]-2-hydroxy-benzenesulfonamide;
N-cyclobutyl-5-[2,6-dimethyl-4-(1H-tetrazol-5-ylamino)-phenoxy]-2-hydroxy-N-methyl-benzamide; and
2-cyclopropylmethanesulfonyl-4-[2,6-dimethyl-4-(1H-tetrazol-5-ylamino)-phenoxy]-phenol; or a stereoisomer, or a pharmaceutically acceptable salt thereof.

12. The compound:
2-cyclobutylmethanesulfonyl-4-[2,6-dimethyl-4-(2H-tetrazol-5-ylamino)-phenoxy]-phenol;
2-cyclobutylmethanesulfonyl-4-[2,6-dichlorol-4-(2H-tetrazol-5-ylamino)-phenoxy]-phenol;
4-[2-chloro-6-methyl-4-(2H-tetrazol-5-ylamino)-phenoxy]-2-cyclobutylmethanesulfonyl-phenol;
2-cyclopentylmethanesulfonyl-4-[2,6-dimethyl-4-(2H-tetrazol-5-ylamino)-phenoxy]-phenol;
2-cyclopentylmethanesulfonyl-4-[2,6-dichlorol-4-(2H-tetrazol-5-ylamino)-phenoxy]-phenol;
4-[2-chloro-6-methyl-4-(2H-tetrazol-5-ylamino)-phenoxy]-2-cyclopentylmethanesulfonyl-phenol;
2-cyclohexylmethanesulfonyl-4-[2,6-dimethyl-4-(2H-tetrazol-5-ylamino)-phenoxy]-phenol;
2-cyclohexylmethanesulfonyl-4-[2,6-dichlorol-4-(2H-tetrazol-5-ylamino)-phenoxy]-phenol;
4-[2-chloro-6-methyl-4-(2H-tetrazol-5-ylamino)-phenoxy]-2-cyclohexylmethanesulfonyl-phenol;
4-[2,6-dimethyl-4-(2H-tetrazol-5-ylamino)-phenoxy]-2-(4-fluoro-benzenesulfonyl)-phenol;
4-[2,6-dichloro-4-(2H-tetrazol-5-ylamino)-phenoxy]-2-(4-fluoro-benzenesulfonyl)-phenol;
4-[2-chloro-6-methyl-4-(2H-tetrazol-5-ylamino)-phenoxy]-2-(4-fluoro-benzenesulfonyl)-phenol,
5-[2,6-dichloro-4-(2H-tetrazol-5-ylamino)-phenoxyl]-2-hydroxy-N-methyl-benzamide;
N-butyl-5-[2,6-dichloro-4-(2H-tetrazol-5-ylamino)-phenoxy]-2-hydroxy-benzamide;
5-[2,6-dichloro-4-(2H-tetrazol-5-ylamino)-phenoxy]-2-hydroxy-N-isopropyl-benzamide;
5-[2,6-dichloro-4-(2H-tetrazol-5-ylamino)-phenoxy]-N-heptyl-2-hydroxy-benzamide;
5-[2,6-dichloro-4-(2H-tetrazol-5-ylamino)-phenoxy]-2-hydroxy-N-nonylbenzamide;
5-[2,6-dichloro-4-(2H-tetrazol-5-ylamino)-phenoxy]-N-(4-fluoro-phenyl)-2-hydroxy-benzamide;
N-cyclopentyl-5-[2,6-dichloro-4-(2H-tetrazol-5-ylamino)-phenoxy]-2-hydroxy-benzamide;
N-cyclohexyl-5-[2,6-dichloro-4-(2H-tetraol-5-ylamino)-phenoxy]-2-hydroxy-benzamide;
N-cycloheptyl-5-[2,6-dichloro-4-(2H-tetrazol-5-ylamino)-phenoxy]-2-hydroxy-benzamide;
N-cyclooctyl-5-[2,6-dichloro-4-(2H-tetrazol-5-ylamino)-phenoxy]-2-hydroxy-benzamide;
5-[2,6-dichloro-4-(2H-tetrazol-5-ylamino)-phenoxy]-2-hydroxy-N-(1-isopropyl-2-methyl-propyl)-benzamide;
N-cyclohexylmethyl-5-[2,6-dichloro-4-(2H-tetrazol-5-ylamino)-phenoxy]-2-hydroxy-benzamide;
N-(R-1-cyclohexyl-ethyl)-5-[2,6-dichloro-4-(2H-tetrazol-5-ylamino)-phenoxy]-2-hydroxy-benzamide;
N-(S-1-cyclohexyl-ethyl)-5-[2,6-dichloro-4-(1H-tetrazol-5-ylamino)-phenoxy]-2-hydroxy-benzamide;
N-cyclopentyl-5-[2,6-dichloro-4-(2H-tetrazol-5-ylamino)-phenoxy]-2-hydroxy-N-methyl-benzamide;
N-cyclohexyl-5-[2,6-dichloro-4-(2H-tetrazol-5-ylamino)-phenoxy-2-hydroxy-N-methyl-benzamide;
N-cycloheptyl-5-[2,6-dichloro-4-(2H-tetrazol-5-ylamino)-phenoxy]-2-hydroxy-N-methyl-benzamide;
N-cyclooctyl-5-[2,6-dichloro-4-(2H-tetrazol-5-ylamino)-phenoxy]-2-hydroxy-N-methyl-benzamide;
5-[2,6-dichloro-4-(2H-tetrazol-5-ylamino)-phenoxy]-2-hydroxy-N-(1-isopropyl-2-methyl-propyl)-N-methyl-benzamide;
N-cyclohexylmethyl-5-[2,6-dichloro-4-(2H-tetrazol-5-ylamino)-phenoxy]-2-hydroxy-N-methyl-benzamide;
N-(R-1-cyclohexyl-ethyl)-5-[2,6-dichloro-4-(2H-tetrazol-5-ylamino)-phenoxy]-2-hydroxy-N-methyl-benzamide; and
N-(S-1-cyclohexyl-ethyl)-5-[2,6-dichloro-4-(1H-tetrazol-5-ylamino)-phenoxy]-2-hydroxy-N-methyl-benzamide, or a stereoisomer, or a pharmaceutically acceptable salt thereof.

13. A method of treating diabetes, the method comprising the step of administering to a patient having diabetes, a therapeutically effective amount of a compound of claim 1, or a stereoisomer, pharmaceutically acceptable salt thereof.

14. The method of claim 13 wherein the diabetes is Type I diabetes.

15. The method of claim 13 wherein the diabetes is Type II diabetes.

16. A method of treating atherosclerosis, the method comprising the step of administering to a patient having atherosclerosis, a therapeutically effective amount of a compound of claim 1, or a stereoisomer, or a pharmaceutically acceptable salt thereof.

17. A method of treating hypertension, the method comprising the step of administering to a patient having hypertension, a therapeutically effective amount of a compound of claim 1, or a stereoisomer, or a pharmaceutically acceptable salt thereof.

18. A method of treating coronary heart disease the method comprising the step of administering to a patient having coronary heart disease, a therapeutically effective amount of a compound of claim 1, or a stereoisomer, or a pharmaceutically acceptable salt thereof.

19. A method of treating hypercholesterolemia, the method comprising the step of administering to a patient having hypercholesterolemia, a therapeutically effective amount of a compound of claim 1, or a stereoisomer, or a pharmaceutically acceptable salt thereof.

20. A method of treating hyperlipidemia, the method comprising the step of administering to a patient having or at risk of having hyperlipidemia, a therapeutically effective amount of a compound of claim 1, or a stereoisomer, or a pharmaceutically acceptable salt thereof.

21. A method of treating thyroid disease, the method comprising the step of administering to a patient having thyroid disease, a therapeutically effective amount of a compound of claim 1, or a stereoisomer, or a pharmaceutically acceptable salt thereof.

22. A method of treating hypothyroidism, the method comprising the step of administering to a patient having hypothyroidism, a therapeutically effective amount of a compound of claim 1, or a stereoisomer, pharmaceutically acceptable salt thereof.

23. A method of treating depression, the method comprising the step of administering to a patient having depression, a therapeutically effective amount of a compound of claim 1, or a stereoisomer, or a pharmaceutically acceptable salt thereof.

24. A method of treating obesity, the method comprising the step of administering to an obese patient a therapeutically effective amount of a compound of claim 1, or a stereoisomer, or a pharmaceutically acceptable salt thereof.

25. A method of treating osteoporosis, the method comprising the step of administering to a patient having osteoporosis, a therapeutically effective amount of a compound of claim 1, or a stereoisomer, or a pharmaceutically acceptable salt thereof.

26. A method of treating thyroid cancer, the method comprising the step of administering to a patient having thyroid cancer, a therapeutically effective amount of a compound of claim 1, or a stereoisomer, or a pharmaceutically acceptable salt thereof.

27. A method of treating glaucoma, the method comprising the step of administering to a patient having glaucoma, a therapeutically effective amount of a compound of claim 1, or a stereoisomer, or a pharmaceutically acceptable salt thereof.

28. A method of treating cardiac arrhythmias, the method comprising the step of administering to a patient having cardiac arrhythmia, a therapeutically effective amount of a compound of claim 1, or a stereoisomer, pharmaceutically acceptable salt thereof.

29. A method of treating congestive heart failure, the method comprising the step of administering to a patient having congestive heart failure, a therapeutically effective amount of a compound of claim 1, or a stereoisomer, or a pharmaceutically acceptable salt thereof.

30. A pharmaceutical composition comprising a compound of claim 1, or a stereoisomer, or a pharmaceutically acceptable salt thereof.

31. A pharmaceutical composition comprising a compound of claim 1, or a stereoisomer, or a pharmaceutically acceptable salt thereof, and an additional compound useful to treat obesity, diabetes, atherosclerosis, hypertension, coronary heart disease, hypercholesterolemia, hyperlipidemia, thyroid disease, thyroid cancer, hypothyroidism, depression, glaucoma, cardiac arrhythmias, congestive heart failure, or osteoporosis.

* * * * *